United States Patent
Pearson et al.

(10) Patent No.: US 11,685,726 B2
(45) Date of Patent: Jun. 27, 2023

(54) PHARMACEUTICAL COMPOSITIONS OF 6-(2-(2H-TETRAZOL-5-YL)ETHYL)-6-FLUORODECAHYDROISOQUINOLINE-3-CARBOXYLIC ACID AND ESTER DERIVATIVES THEREOF

(71) Applicant: Sea Pharmaceuticals LLC, Cambridge, MA (US)

(72) Inventors: James Philip Pearson, Cambridge, MA (US); Eduardo J. Martinez, Bryn Mawr, PA (US)

(73) Assignee: SEA PHARMACEUTICALS LLC, Cambridge, MA (US)

( * ) Notice: Subject to any disclaimer, the term of this patent is extended or adjusted under 35 U.S.C. 154(b) by 0 days.

(21) Appl. No.: 18/147,856

(22) Filed: Dec. 29, 2022

(65) Prior Publication Data
US 2023/0150971 A1 May 18, 2023

Related U.S. Application Data

(63) Continuation of application No. PCT/US2021/040339, filed on Jul. 2, 2021.

(60) Provisional application No. 63/047,359, filed on Jul. 2, 2020.

(51) Int. Cl.
| | | |
|---|---|---|
| *C07D 401/06* | (2006.01) | |
| *A61P 25/08* | (2006.01) | |
| *A61P 29/00* | (2006.01) | |

(52) U.S. Cl.
CPC ............ *C07D 401/06* (2013.01); *A61P 25/08* (2018.01); *A61P 29/00* (2018.01)

(58) Field of Classification Search
CPC ......... C07D 401/06; A61P 25/08; A61P 29/00
USPC ....................................................... 514/307
See application file for complete search history.

(56) References Cited

U.S. PATENT DOCUMENTS

| | | | |
|---|---|---|---|
| 5,071,589 A | 12/1991 | Knudsen et al. | |
| 5,284,957 A | 2/1994 | Huff | |
| 5,648,492 A | 7/1997 | Arnold et al. | |
| 5,670,516 A | 9/1997 | Arnold et al. | |
| 5,675,008 A | 10/1997 | Bertsch et al. | |
| 7,247,644 B2 | 7/2007 | Ornstein | |

FOREIGN PATENT DOCUMENTS

WO 0102367 A2 1/2001

OTHER PUBLICATIONS

White et al., "The National Institutes of Health Anticonvulsant Drug Development Program: Screening for Efficacy", Antiepileptic Drug Development, Advances in Neurology, vol. 76, pp. 29-39. 1998.
Toman et al., "The Search for New Drugs Against Epilepsy", Texas Reports on Biology and Medicine, vol. 10, pp. 96-104. 1952.
Litchfield et al., "A Simplified Method of Evaluating Dose-Effect Experiments", The Journal of Pharmacology and Experimental Therapeutics, pp. 99-113. 1949.
Barker et al., "Fe(III)/NaBH4-Mediated Free Radical Hydrofluorination of Unactivated Alkenes", J. Am. Chem. Soc., vol. 134, pp. 13588-13591. 2012.
Barton et al., "Comparison of the effect of glutamate receptor modulators in the 6 Hz and maximal electroshock seizure models", Epilepsy Research, vol. 56, pp. 17-26. 2003.
Barton et al., "Pharmacological characterization of the 6 Hz psychomotor seizure model of partial epilepsy", Epilepsy Research, vol. 47, pp. 217-227. 2001.
Brown et al., "Comparative Assay of Antiepileptic Drugs by 'Psychomotor' Seixure Test and Minimal Eletroshock Threshold Test", pp. 273-283. Sep. 22, 1952.
Chappell et al., "A crossover, add-on trial of talampanel in patients with refactory partial seizures", Neurology 58, pp. 1680-1682. 2002.
Clifford et al., "The Functional Anatomy and Pathology of Lithium-Pilocarpine and High-Does Pilocarpine Seizures", Neuroscience, vol. 23, No. 3, pp. 953-968. 1987.
During et al., "Extracellular Hippocampal Glutamate and Spontaneous Seizure in the Conscious Human Brain", The Lancet, vol. 341, No. 8861, 6 pages. Jun. 26, 1993.
Fox et al. "Cannabinoids and Novelty Investigation: Influence of Age and Duration of Exposure", Behav Brain Res., vol. 196(2), pp. 248-253. Jan. 23, 2009.
French et al., "Evaluation of Adjunctive Perampanel in Patients with Refractory Partial-onset Seizures: Results of Randomized Global Phase III Study 305", Epilepsia, vol. 54(1), pp. 117-125. 2013.
Greene, "Protective Groups in Organic Synthesis" Fifth Edition, 1399 pages. 2014.
Hanada et al., "Effect of Perampanel, a Novel AMPA Antagonist, on Benzodiazepine-Resistant Status Epilepticus in a Lithium-Pilocarpinen Rat Model", Pharmacology Research & Perspecitives, vol. 2(5), 8 pages. 2014.
Hanada et al., "Perampanel: A Novel, Orally Active, Noncompetitve AMPA-Receptor Antagonist that Reduces Seizure Activity in Rodent Models of Epilepsy", Epilepsia, vol. 52(7), pp. 1331-1340. 2011.

(Continued)

*Primary Examiner* — Yevgeny Valenrod
(74) *Attorney, Agent, or Firm* — Heslin Rothenberg Farley & Mesiti P.C.

(57) ABSTRACT

6-(2-(2H-tetrazol-5-yl)ethyl)-6-fluorodecahydroisoquinoline-3-carboxylic acid and 6-(2-(2H-tetrazol-5-yl)ethyl)-6-fluorodecahydroisoquinoline-3-carboxylic acid hydrocarbyl ester derivatives of formula

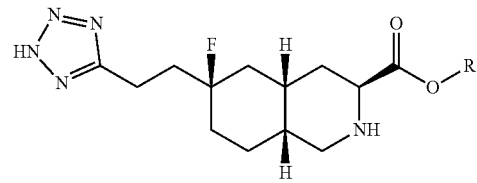

are disclosed, as are pharmaceutical compositions and methods for the treatment of pain, epilepsy, convulsions, and seizures employing those compositions.

20 Claims, 20 Drawing Sheets

(56) References Cited

OTHER PUBLICATIONS

Inami et al., "Synthesis and Pharmaceutical Evaluation of 3-[(4-Oxo-4H-pyrudi[3,2-e][1,3]thiazin-2-yl)(phenyl)amino] propanenitrile Derivatives as Orally Active AMPA Receptor Antagonists", Chem. Pharm. Bull, vol. 67, pp. 699-706. 2019.
International Search Report and Written Opinion in International Application No. PCT/US21/40339, 5 pages. dated Oct. 13, 2021.
Irwin, "Comprehensive Observational Assessment: la. A Systematic, Quantitative Procedure for Assessing the Behavioral and Physiologic State of the Mouse", Psychopharmacologia (Berl.), vol. 13, pp. 222-257. 1968.
Krauss et al., "Perampanel, A Selective, Noncompetitve a-amino-3-hydroxy-5-methyl-4-isoxazolepropionic Acid Receptor Antagonist, as Adjuctive Therapy for Refractory Partial-Onset Seizures: Interim Results from Phase III, extension study 307", Epilepsia, vol. 54(1), pp. 126-134. 2013.
Leander et al., "Anticonvulsant Effects of Phencyclidine-like Drugs: Relation to N-Methyl-D-Aspartic Acid Antagonism", Brain Research, pp. 368-372. 1988.
Leander, "Evaluation of Detromethorphan and Carbetapentane as Anticonvulsants and N-methyl-D-aspartic Acid Antagonists in Mice", Epilepsy Res , vol. 4, pp. 28-33. 1989.
Lu et al., "Widely Applicable Hydrofluorination of Alkenes via Bifunctional Activation of Hydrogen Fluoride", J. Am. Chem. Soc., vol. 139, pp. 18202-18205. 2017.
Malmberg et al., "Antinociceptive Actions of Spinal Nonsteroidal Anti-Inflammatory Agents on the Formalin Test in the Rat", The Journal of Pharmacology and Experimantal Therapeutics, vol. 263, No. 1, pp. 136-146. 1992.
Metcalf et al., "Development and Pharmacologic Characterization of the Rat 6 Hz Model of Partial Seizures", Epilepsia, vol. 58(6), pp. 1073-1084. 2017.
Metcalf et al., "Efficacy of mGlu2-positive Allosteric Modulators Alone and in Combination with Levetiracetam in the Mouse 6 Hz Model of Psychomotor Seizures", Epilepsia, vol. 58(3), pp. 484-493. 2017.
Metcalf et al., "Preclinical Evaluation of Intravenous NAX 810-2, a Novel GalR2-preferring Analog, for Anticonvulsant Efficacy and Pharmacokinetics", Epilepsia, vol. 58(2), pp. 239-246. 2017.
Metcalf et al., "Status Epilepticus Produces Chronic Alterations in Cardiac Sympathovagal Balance", Epilepsia, vol. 50(4), pp. 747-754. 2009.
Olah et al., "Fluorinations with Pyridinium Polyhydrogen Fluoride Reagent: 1-Fluoroadamantane", Organic Syntheses, Coll., 6 pages. 2014.
Ornstein et al., "(3SR,4aRS,6RS,8aRS)-6-(1H-Tetrazol-5-yl)ethyl]decahydroisoquinoline-3-carboxylic Acid: A Structurally Novel, Systemically Active, Competitive AMPA Receptor Antagonist", J. Med. Chem. viol. 36, pp. 2046-2048. 1993.
Ornstein et al., "Syntheses of 6-Oxodecahydroisoquinoline-3-carboxylates. Useful Intermediates for the Preparation of Conformationally Defined Excitatory Amino Acid Antagonists", J. Org. Chem., vol. 56, No. 14, pp. 4388-4392. Jan. 25, 1991.
Rogawski, "Revisiting AMPA Receptors as an Antiepileptic Drug Target", Epilepsy Currents, vol. 11, No. 2, pp. 56-63. 2011.
Scharfman, "The Neurobiology of Epilepsy", Curr Neurol Neurosci Rep. vol. 7(4), pp. 348-354. Jul. 2007.
Shigehisa et al., "Cobalt-Catalyzed Hydrofluorination of Unactivated Olefins: A Radical Approach of Fluorine Transfer", Organic Letters, vol. 15, No. 20, pp. 5158-5161. 2013.
Swinyard et al., "Comparative Assays of Antiepileptic Drugs in Mice and Rats", 12 pages. Jul. 24, 1952.
Thibaudeau et al., "A Novel, Facile Route to Beta-Fluoroamines by Hydrofluorination Using Superacid HF/SbF5", The Royal Society of Chemistry, 40 pages. 2007.
Toman, "Neuropharmacologic Considerations in Psychic Seizures", Neurology, 18 pages. 1951.
Wheeler-Aceto et al., "The Rat Paw Formalin Test: Comparison of Noxious Agent", Pain, vol. 40, pp. 229-238. 1990.
White et al., "General Principles Discovery and Preclinical Development of Antiepileptic Drugs", pp. 36-48. 2002.
White et al., "The Anticonvulsant Profile of Rufinamide (CGP 33101) in Rodent Seizure Models", Epilepsia, vol. 45(7), pp. 1213-1220. 2008.
White et al., "The Early Identification of Anticonvulsant Activity: Role of the Maximal Activity: Role of the Maximal Electroshock and Subsutaneous Pentylenetetrazol Seizure Models", Ital. J. Neurol. Sci., vol. 16, pp. 73-77. 1995.
Woodbury et al., "Design and Use of a New Electroshock Seizure Apparatus, and Analysis of Factors Altering Seizure Threshold and Pattern", Arch. Int. Pharmacodyn., XCII, No. 1, pp. 98-107. 1952.
Wu et al., "The neuroprotective effect of perampanel in lithium-pilocarpine rat seizure model", Epilepsy Research, vol. 137, pp. 152-158. 2017.
Yamaguchi et al., "Anticonvulsant Activity of AMPA/kainate antagonists: comparison of GYKI 52466 and NBQX in maximal electroshock and shemoconvulsant seizure models". Epilepsy Research, vol. 15, pp. 179-184. 1993.
Yamashita et al., "Effects of 2-[N-(4-Chlorophenyl)-N-methylamino]-4Hpyrido[ 3.2-e]-1,3-thiazin-4-one (YM928), an Orally Active α-Amino-3-hydroxy-5-methyl-4-isoxazolepropionic Acid Receptor Antagonist, in Models of Generalized Epileptic Seizure in Mice and Rats", The Journal of Pharmacology and Experimental Therapeutics, vol. 308, No. 1, pp. 127-133. 2004.

PLASMA

CSF

BRAIN

PHARMACEUTICAL COMPOSITIONS OF 6-(2-(2H-TETRAZOL-5-YL)ETHYL)-6-FLUORO-DECAHYDROISOQUINOLINE-3-CARBOXYLIC ACID AND ESTER DERIVATIVES THEREOF

CROSS REFERENCE TO RELATED APPLICATIONS

This application is a by-pass continuation of International Application PCT/US2021/040339, filed Jul. 2, 2021, and published as WO2022006537 on Jan. 6, 2022. PCT/US2021/040339 claims priority from U.S. application No. 63/047,359, filed Jul. 2, 2020. The entire contents of each of these prior applications are hereby incorporated herein by reference.

FIELD OF THE INVENTION

The present invention relates to pharmaceutical compositions of 6-(2-(2H-tetrazol-5-yl)ethyl)-6-fluorodecahydroisoquinoline-3-carboxylic acid and 6-(2-(2H-tetrazol-5-yl)ethyl)-6-fluorodecahydroisoquinoline-3-carboxylic acid hydrocarbyl ester derivatives for use in the treatment of pain and epilepsy.

BACKGROUND OF THE INVENTION

The α-amino-3-hydroxy-5-methyl-4-isoxazolepropionic acid receptor (also known as AMPA receptor, AMPAR, or quisqualate receptor) is an ionotropic transmembrane receptor that is known as a glutamate-gated ion channel that mediates fast synaptic transmission in the central nervous system (CNS). AMPAR has been traditionally classified as a non-NMDA-type receptor, along with the kainate receptor.

Glutamate is the major excitatory amino acid neurotransmitter in the central nervous system. AMPA receptors (AMPARs) are large multisubunit ion channels and are made of combinations of four AMPAR protein subunits GluA1, GluA2, GluA3, GluA4 (encoded by 4 separate genes). AMPARs are found in excitatory synapses of neurons and transduce fast excitatory neurontransmission. AMPARs transmit a glutamate signal into a depolarization of the postsynaptic neuron. Glutamate released from the excitatory neuron diffuses across the synapse and binds to AMPARs in the postsynaptic neurons. AMPARs physically span the neuronal cell membrane and contain an ion pore or ion channel that is selectively inwardly permeable to the flow of primarily sodium ions (but also potassium and rarely to calcium) into the cell from the outside. In the absence of glutamate the AMPAR ion pore is closed and ions thus cannot flow into the neuron. When glutamate binds the AMPAR it opens allowing mainly sodium ions to pass thru the pore thus crossing the post-synaptic neuronal cell membrane which results in depolarization. Thus sodium is carries the depolarizing current. AMPARs are critical to neuronal networks and to the physiological function of the brain and central nervous system. In summary AMPA receptors are neurotransmitter-gated (glutamate-gated) ion channels that open only in response to the chemical signal glutamate.

AMPA receptors play a key role in the generation and spread of epileptic seizures Scharfman H E. 2007. Curr Neurol Neurosci Rep. 7:348-354. "*The Neurobiology of Epilepsy*"; Rogawski M A. 2011. Epilepsy Currents 11:56-63. "*Revisiting AMPA receptors as an antiepileptic drug target*". Neurosurgeons and neurologists have observed in clinical samples collected from human epilepsy (n=6 patients) brain (hippocampus) microdialysates that glutamate levels were increased prior to and increased even further during seizures in these patients (During M J and Spencer D D 1993. The Lancet. 341(8861):1607-10 "*Extracellular Hippocampal Glutamate and Spontaneous Seizure in the Conscious Human Brain*").

Treatment with many different AMPAR antagonists in studies using animal models of seizures, convulsion and epilepsy have consistently demonstrated pre-clinical efficacy of this class of compounds regardless of noncompetitive action or competitive mechanism of the AMPAR antagonist molecule. In early clinical trials neurologists observed treatment with experimental therapeutic AMPAR antagonist talampanel showed reduction of seizures in epilepsy patients Chappell A S, Sander J W, Brodie M J, Chadwick D, Lledo A, Zhang D, Bjerke J, Kiesler G M, Arroyo S. 2002. Neurology 58:1680-1682. "*A Crossover, Add-On Trial of Talampanel in Patients With Refractory Partial Seizures*"). A decade later the AMPAR antagonist perampanel was approved in as the first FDA and EMEA approved AMPAR antagonist for the treatment of epilepsy (French J A, Krauss G L, Steinhoff B J, Squillacote D, Yang H, Kumar D, Laurenza A. 2013. Epilepsia 54:117-125. "*Evaluation of adjunctive perampanel in patients with refractory partial-onset seizures: Results of randomized global phase III study* 305"; and Krauss G L, Perucca E, Ben-Menachem E, Kwan P, Shih J J, Squillacote D, Yang H, Gee M, Zhu J, Laurenza A. 2013. Epilepsia 54:126-134. "*Perampanel, a selective, noncompetitive α-amino-3-hydroxy-5-methyl-4-isoxazolepropionic acid receptor antagonist, as adjunctive therapy for refractory partial-onset seizures: interim results from phase III, extension study* 307".

AMPAR's permeability to calcium and other cations, such as sodium and potassium, is governed by the GluA2 subunit. If an AMPAR lacks a GluA2 subunit, then it will be permeable to sodium, potassium, and calcium. The presence of a GluA2 subunit will almost always render the channel impermeable to calcium. This is determined by post-transcriptional modification (RNA editing) of the Q-to-R editing site of the GluA2 mRNA. Here, A→I (Adenosine to Inosine) editing (by Adenosine Deaminase Acting on RNA2) alters the GluA2 RNA coding for uncharged amino acid glutamine (Q) to instead code for the positively charged arginine (R) in the receptor's ion channel. The positively charged amino acid at the critical point makes it energetically unfavorable for calcium to enter the cell through the pore. Sodium is the major ion that the AMPAR glutamate-gated ion channel is permeable to.

Failure of the adenosine deaminase acting on RNA (ADAR) to edit GluA2 mRNA results in certain neurological disorders due to the permeability of the resulting altered AMPARs for calcium. Animals lacking ADAR2 die of seizures by day 21 after birth. However in epilepsy normal edited AMPAR receptors are present and they are permeable to sodium.

AMPAR antagonists represent a potential target for the treatment of epilepsy as they can reduce AMPAR mediated overactivation of neuronal networks in epilepsy. Reviewed in Rogawski M A. 2011. Epilepsy Currents 11:56-63. "*Revisiting AMPA receptors as an antiepileptic drug target*".

U.S. Pat. No. 5,670,516 discloses that certain decahydroisoquinoline derivatives are AMPA receptor antagonists, and as such are useful in the treatment of many different neurological conditions, including pain, migraine, convulsions, and seizures. In addition, WO 01/02367 A3, published Jan. 11, 2001, discloses diester prodrug forms of the selective GluR₅ antagonist 3S,4aR,6S,8aR-6-(((4-carboxy)phenyl)methyl)-1,2,3,4,4a,5,6,7,8,8a-decahydroisoquinoline-3-carboxylic acid.

U.S. Pat. No. 7,247,644 discloses that monoesters of the monoacid, (3S,4aR,6R,8aR)-6-[2-(1(2)H-tetrazole-5-yl)ethyl-1,2,3,4,4a,5,6,7,8,8a-decahydroisoquinoline-3-carboxylic acid provide significantly improved bioavailability of the monoacid as compared to that provided by administration of the monoacid itself.

However, the bioavailability of these previous methods is still not sufficiently high to be considered for oral applications.

BRIEF SUMMARY

In a first aspect, the present invention relates to a compound of formula I:

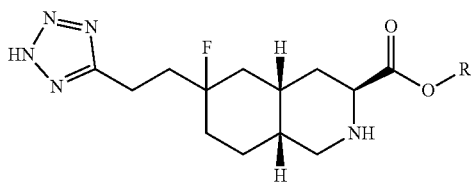

wherein:
R is selected from H and (C₁-C₂₀)hydrocarbyl.

In second aspect, the present invention relates to a compound of formula II:

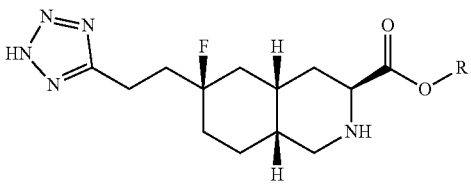

In a third aspect, the compound of formula II, wherein R=H, is shown to selectively inhibit (S)-α-amino-3-hydroxy-5-methyl-4-isoxazolepropionic acid (s-AMPA)-induced calcium permeability of AMPAR in vitro and prevent seizures in vivo in an animal model for epilepsy.

In a fourth aspect, the present invention relates to a method or medicament for treating epilepsy and/or pain via the administration of compounds of formula II as an orally bioavailable prodrug (R≠H) of the active pharmaceutical ingredient (R=H).

In a fourth aspect, the present invention relates to pharmaceutical compositions comprising a pharmaceutically acceptable carrier and a compound as described herein.

These and other objects, features, and advantages of the invention will become apparent from the following detailed description of the various aspects of the present invention.

BRIEF DESCRIPTION OF FIGURES AND TABLES

Figure 1:
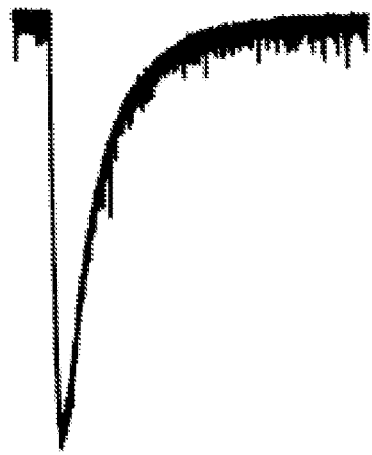
FIG. 1 illustrates the results of s-AMPA induced currents in vitro electrophysiology studies of pyramidal neurons in Sprague Dawley rat brain cortex slices with Compound #1 which is 6-(2-(2H-tetrazol-5-yl)ethyl)-6-fluorodecahydroisoquinoline-3-carboxylic acid (R=H)
Figure 2:
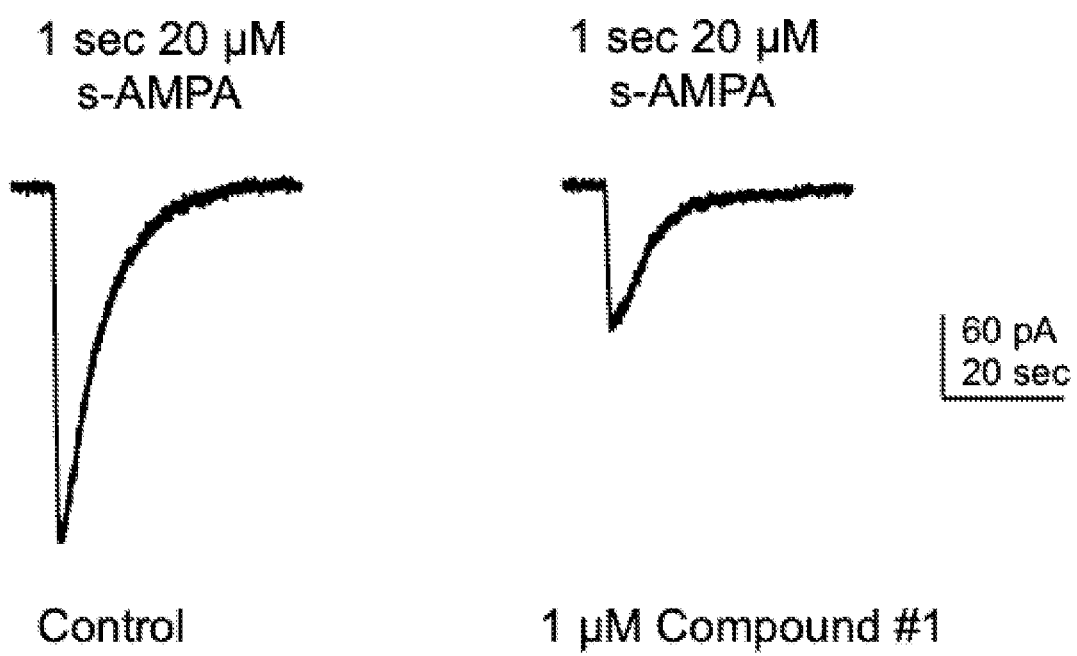
FIG. 2 illustrates the results of s-AMPA induced currents in vitro electrophysiology studies of pyramidal neurons in Sprague Dawley rat brain cortex slices with Compound #1.
Figure 3:
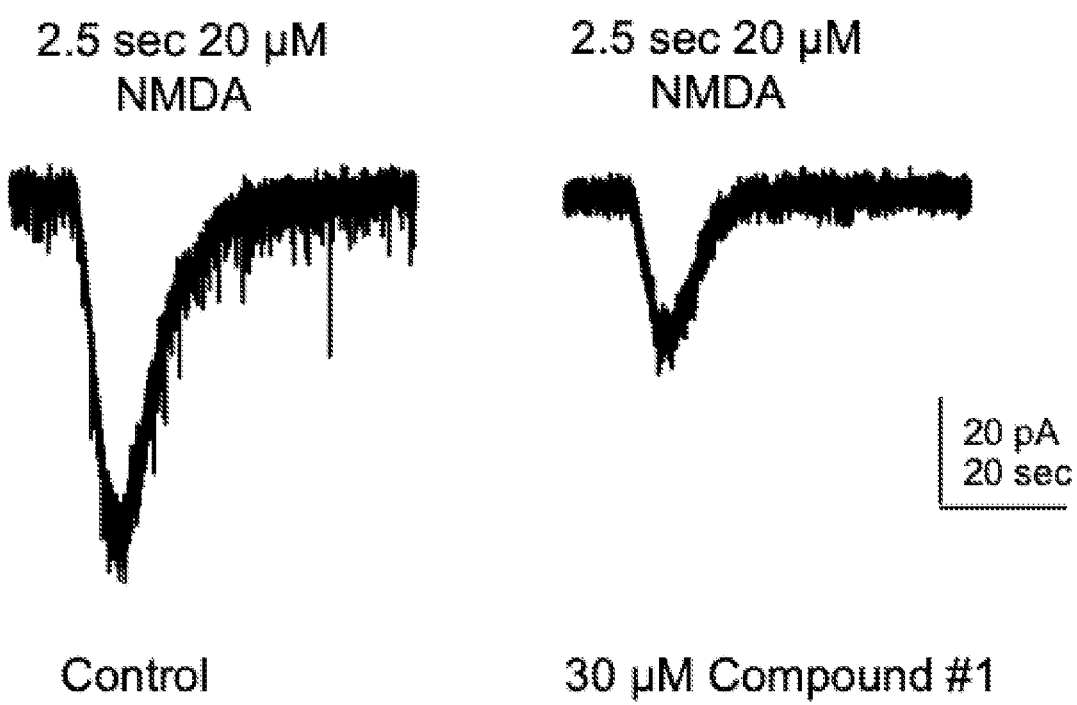
FIG. 3 illustrates the results of NMDA induced currents in vitro electrophysiology studies of pyramidal neurons in Sprague Dawley rat brain cortex slices with Compound #1.

TABLE 1 illustrates some compounds;

TABLE 2 illustrates the comparative results of s-AMPA vs. NMDA in in vitro electrophysiology studies of pyramidal neurons with 6-(2-(2H-tetrazol-5-yl)ethyl)-6-fluorodecahydroisoquinoline-3-carboxylic acid (R=H); and TABLE 3 presents the results of an in vivo efficacy study of 6-(2-(2H-tetrazol-5-yl)ethyl)-6-fluorodecahydroisoquinoline-3-carboxylic acid (R=H).

DETAILED DESCRIPTION

The present disclosure relates generally to 6-(2-(2H-tetrazol-5-yl)ethyl)-6-fluorodecahydroisoquinoline-3-carboxylic acid and 6-(2-(2H-tetrazol-5-yl)ethyl)-6-fluorodecahydroisoquinoline-3-carboxylic acid hydrocarbyl ester derivatives, and to pharmaceutical compositions thereof, as well as methods for treating certain disorders.

Throughout this specification the terms and substituents retain their definitions.

For convenience and clarity, certain terms employed in the specification, examples and claims are described herein.

The terms "hydrocarbyl," "aliphatic hydrocarbyl," "aromatic hydrocarbyl," and "alkyl," as used herein and described below, include all possible structural features that are possible for the defined group, e.g., linear, branched, cyclic, polycyclic, bridged, etc.

"Hydrocarbyl" (or "hydrocarbon") refers to any group comprised of hydrogen and carbon as the only elemental constituents.

A first subset of hydrocarbyl is "aliphatic hydrocarbyl," which refers to hydrocarbyl groups that are not aromatic. They include any variety of $sp^3$-, $sp^2$-, and sp-hybridized carbons that are not arranged to be aromatic as readily understood by a person with an ordinary knowledge of chemistry. Aliphatic hydrocarbyl groups encompass one or more alkane ($sp^3$), alkene ($sp^2$), alkyne (sp), and allene ($sp^2$ and sp) functional groups. Two or more alkene, alkyne, and/or allene functional groups may be conjugated in a hydrocarbyl group and the group is still defined as an aliphatic hydrocarbyl group as long as the conjugation does not constitute aromaticity.

Examples of aliphatic hydrocarbyl groups include methyl, ethyl, isopropyl, isobutyl, cyclopropyl, t-butyl, neopentyl, 3-methylbutyl, 3,3-dimethylbutyl, 2-propylpentyl, 2-butylhexyl, 2-pentylheptyl, 2-hexyloctyl, n-hexyl, n-octyl, 2-ethylbutyl, 1-methyl-2-ethylbutyl, decyl, dodecyl, tetradecyl, 9-hexadec-en-yl, 9-octadec-en-yl, 9,12-octadec-dien-yl, cyclohexyl, cyclohexylmethyl, 2-cyclohexylethyl, dicyclohexylmethyl, 2-butenyl, 2-butynyl, cyclopentyl, norbornyl, etc.

A second subset of hydrocarbyl is "aromatic hydrocarbyl" and "aryl," which refers to hydrocarbyl groups that are aromatic. Aromatic hydrocarbyl groups include, for example, phenyl ($C_6H_5$), naphthyl ($C_{10}H_7$), anthracene ($C_{14}H_9$), etc.

A third subset of hydrocarbyl is "alkyl" (or alkane) which refers to hydrocarbyl groups consisting exclusively of $sp^3$-hybridized carbon atoms. Alkyl groups are also a subset of aliphatic hydrocarbyl groups, except they are completely saturated hydrocarbyl groups that exclude the presence of $sp^2$- and sp-hybridized carbon atoms. Examples of alkyl groups from the examples described above for aliphatic hydrocarbyl groups include methyl, ethyl, isopropyl, isobutyl, cyclopropyl, t-butyl, neopentyl, 3-methylbutyl, 3,3-dimethylbutyl, 2-propylpentyl, 2-butylhexyl, 2-pentylheptyl, 2-hexyloctyl, n-hexyl, n-octyl, 2-ethylbutyl, 1-methyl-2-ethylbutyl, decyl, dodecyl, tetradecyl, cyclohexyl, cyclohexylmethyl, 2-cyclohexylethyl, dicyclohexylmethyl, cyclopentyl, norbornyl, etc. Alkyl groups do not include, e.g., 9-hexadec-en-yl, 9-octadec-en-yl, 9,12-octadec-dien-yl, 2-butenyl, 2-butynyl, etc., which are also examples of aliphatic hydrocarbyl groups described above.

Hydrocarbyl groups may be exclusively aliphatic hydrocarbyl, aromatic hydrocarbyl or alkyl in nature. Alternatively, the term hydrocarbyl encompasses combinations of one or more of these subset groups, typically as substituents. Thus, an aliphatic hydrocarbyl optionally substituted with, e.g., a phenyl group can be encompassed by the term "hydrocarbyl" or "aliphatic hydrocarbyl optionally substituted with phenyl." "Alkyl optionally substituted with phenyl" indicates that, besides the phenyl group, all other carbon atoms are $sp^3$-hybridized.

As defined above, aliphatic hydrocarbyl, aromatic hydrocarbyl (i.e., aryl), and alkyl, alone or in combinations, are proper limitations of hydrocarbyl provided carbon atom count is the same or less as the depended-upon hydrocarbyl carbon count. Likewise, alkyl is a further limitation of aliphatic hydrocarbyl provided carbon atom count is the same or less.

As used herein, the term "optionally substituted" may be used interchangeably with "unsubstituted or substituted". The term "substituted" refers to the replacement of one or more hydrogen atoms in a specified group with a specified radical. For example, substituted alkyl, aryl, cycloalkyl, etc. refer to alkyl, aryl, or cycloalkyl wherein one or more H atoms in each residue are replaced with the specified substituent.

As indicated above, definitions of R for hydrocarbyl, aliphatic hydrocarbyl, aromatic hydrocarbyl, and alkyl groups additionally include the number of carbons, designated as ($C_x$-$C_y$), where x is the minimum number of carbon atoms and y is the maximum number of carbon atoms. For example, "($C_1$-$C_{20}$)hydrocarbyl" indicates a hydrocarbyl group of one to twenty carbons and "aliphatic ($C_5$-$C_{14}$) hydrocarbyl" indicates an aliphatic hydrocarbyl group of five to fourteen carbons. The carbon count of optional substituents containing carbon, e.g., phenyl, are separate from the ($C_x$-$C_y$) designation.

Unless otherwise specified, the term "carbocycle" is intended to include ring systems in which the ring atoms are all carbon but of any oxidation state. Thus ($C_3$-$C_{10}$) carbocycle refers to both non-aromatic and aromatic systems, including such systems as cyclopropane, benzene and cyclohexene; ($C_8$-$C_{12}$) carbopolycycle refers to such systems as norbornane, decalin, indane and naphthalene. Carbocycle, if not otherwise limited, refers to monocycles, bicycles and polycycles.

The compounds described herein may contain, in a substituent R, double bonds and may also contain other centers of geometric asymmetry; unless specified otherwise, it is intended that the compounds include both E and Z geometric isomers. Likewise, all tautomeric forms are also intended to be included, for example tetrazole tautomers:

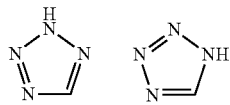

The compounds may also contain, in a substituent R, one or more asymmetric centers and may thus give rise to enantiomers, diastereomers, and other stereoisomeric forms that may be defined, in terms of absolute stereochemistry, as (R)- or (S)-. The present invention is meant to include all such possible isomers, as well as their racemic and optically pure forms. Optically active (R)- and (S)-isomers may be prepared using chiral synthons or chiral reagents or resolved using conventional techniques.

For clarity, the atom numbering convention for the decahydroisoquinoline ring system and its appendages is shown below:

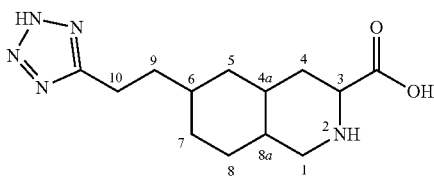 [SMILES: O=C(O)C1CC2CC(CCc3nn[nH]n3)CCC2CN1]

In various embodiments of the present invention, R is chosen from: $(C_1-C_{20})$hydrocarbyl, $(C_1-C_{19})$hydrocarbyl, $(C_1-C_{18})$hydrocarbyl, $(C_1-C_{17})$hydrocarbyl, $(C_1-C_{16})$hydrocarbyl, $(C_1-C_{15})$hydrocarbyl, $(C_1-C_{14})$hydrocarbyl, $(C_1-C_{13})$hydrocarbyl, $(C_1-C_{12})$hydrocarbyl, $(C_1-C_{11})$hydrocarbyl, $(C_1-C_{10})$hydrocarbyl, $(C_1-C_9)$hydrocarbyl, $(C_1-C_8)$hydrocarbyl, $(C_1-C_7)$hydrocarbyl, $(C_1-C_6)$hydrocarbyl, $(C_1-C_5)$hydrocarbyl, $(C_1-C_4)$hydrocarbyl, and $(C_1-C_3)$hydrocarbyl.

In various embodiments of the present invention, R is chosen from: $(C_2-C_{20})$hydrocarbyl, $(C_2-C_{19})$hydrocarbyl, $(C_2-C_{18})$hydrocarbyl, $(C_2-C_{17})$hydrocarbyl, $(C_2-C_{16})$hydrocarbyl, $(C_2-C_{15})$hydrocarbyl, $(C_2-C_{14})$hydrocarbyl, $(C_2-C_{13})$hydrocarbyl, $(C_2-C_{12})$hydrocarbyl, $(C_2-C_{11})$hydrocarbyl, $(C_2-C_{10})$hydrocarbyl, $(C_2-C_9)$hydrocarbyl, $(C_2-C_8)$hydrocarbyl, $(C_2-C_7)$hydrocarbyl, $(C_2-C_6)$hydrocarbyl, $(C_2-C_5)$hydrocarbyl, $(C_2-C_4)$hydrocarbyl, and $(C_2-C_3)$hydrocarbyl.

In various embodiments of the present invention, R is chosen from: $(C_3-C_{20})$hydrocarbyl, $(C_3-C_{19})$hydrocarbyl, $(C_3-C_{18})$hydrocarbyl, $(C_3-C_{17})$hydrocarbyl, $(C_3-C_{16})$hydrocarbyl, $(C_3-C_{15})$hydrocarbyl, $(C_3-C_{14})$hydrocarbyl, $(C_3-C_{13})$hydrocarbyl, $(C_3-C_{12})$hydrocarbyl, $(C_3-C_{11})$hydrocarbyl, $(C_3-C_{10})$hydrocarbyl, $(C_3-C_9)$hydrocarbyl, $(C_3-C_8)$hydrocarbyl, $(C_3-C_7)$hydrocarbyl, $(C_3-C_6)$hydrocarbyl, $(C_3-C_5)$hydrocarbyl, and $(C_3-C_4)$hydrocarbyl.

In various embodiments of the present invention, R is chosen from: $(C_4-C_{20})$hydrocarbyl, $(C_4-C_{19})$hydrocarbyl, $(C_4-C_{18})$hydrocarbyl, $(C_4-C_{17})$hydrocarbyl, $(C_4-C_{16})$hydrocarbyl, $(C_4-C_{15})$hydrocarbyl, $(C_4-C_{14})$hydrocarbyl, $(C_4-C_{13})$hydrocarbyl, $(C_4-C_{12})$hydrocarbyl, $(C_4-C_{11})$hydrocarbyl, $(C_4-C_{10})$hydrocarbyl, $(C_4-C_9)$hydrocarbyl, $(C_4-C_8)$hydrocarbyl, $(C_4-C_7)$hydrocarbyl, $(C_4-C_6)$hydrocarbyl, and $(C_4-C_5)$hydrocarbyl.

In various embodiments of the present invention, R is chosen from: $(C_5-C_{20})$hydrocarbyl, $(C_5-C_{19})$hydrocarbyl, $(C_5-C_{18})$hydrocarbyl, $(C_5-C_{17})$hydrocarbyl, $(C_5-C_{16})$hydrocarbyl, $(C_5-C_{15})$hydrocarbyl, $(C_5-C_{14})$hydrocarbyl, $(C_5-C_{13})$hydrocarbyl, $(C_5-C_{12})$hydrocarbyl, $(C_5-C_{11})$hydrocarbyl, $(C_5-C_{10})$hydrocarbyl, $(C_5-C_9)$hydrocarbyl, $(C_5-C_8)$hydrocarbyl, $(C_5-C_7)$hydrocarbyl, and $(C_5-C_6)$hydrocarbyl.

In various embodiments of the present invention, R is chosen from: $(C_6-C_{20})$hydrocarbyl, $(C_6-C_{19})$hydrocarbyl, $(C_6-C_{18})$hydrocarbyl, $(C_6-C_{17})$hydrocarbyl, $(C_6-C_{16})$hydrocarbyl, $(C_6-C_{15})$hydrocarbyl, $(C_6-C_{14})$hydrocarbyl, $(C_6-C_{13})$hydrocarbyl, $(C_6-C_{12})$hydrocarbyl, $(C_6-C_{11})$hydrocarbyl, $(C_6-C_{10})$hydrocarbyl, $(C_6-C_9)$hydrocarbyl, $(C_6-C_8)$hydrocarbyl, and $(C_6-C_7)$hydrocarbyl.

In various embodiments of the present invention, R is chosen from: $(C_7-C_{20})$hydrocarbyl, $(C_7-C_{19})$hydrocarbyl, $(C_7-C_{18})$hydrocarbyl, $(C_7-C_{17})$hydrocarbyl, $(C_7-C_{16})$hydrocarbyl, $(C_7-C_{15})$hydrocarbyl, $(C_7-C_{14})$hydrocarbyl, $(C_7-C_{13})$hydrocarbyl, $(C_7-C_{12})$hydrocarbyl, $(C_7-C_{11})$hydrocarbyl, $(C_7-C_{10})$hydrocarbyl, $(C_7-C_9)$hydrocarbyl, and $(C_7-C_8)$hydrocarbyl.

In various embodiments of the present invention, R is chosen from: $(C_8-C_{20})$hydrocarbyl, $(C_8-C_{19})$hydrocarbyl, $(C_8-C_{18})$hydrocarbyl, $(C_8-C_{17})$hydrocarbyl, $(C_8-C_{16})$hydrocarbyl, $(C_8-C_{15})$hydrocarbyl, $(C_8-C_{14})$hydrocarbyl, $(C_8-C_{13})$hydrocarbyl, $(C_8-C_{12})$hydrocarbyl, $(C_8-C_{11})$hydrocarbyl, $(C_8-C_{10})$hydrocarbyl, and $(C_8-C_9)$hydrocarbyl.

In various embodiments of the present invention, R is chosen from: $(C_9-C_{20})$hydrocarbyl, $(C_9-C_{19})$hydrocarbyl, $(C_9-C_{18})$hydrocarbyl, $(C_9-C_{17})$hydrocarbyl, $(C_9-C_{16})$hydrocarbyl, $(C_9-C_{15})$hydrocarbyl, $(C_9-C_{14})$hydrocarbyl, $(C_9-C_{13})$hydrocarbyl, $(C_9-C_{12})$hydrocarbyl, $(C_9-C_{11})$hydrocarbyl, and $(C_9-C_{10})$hydrocarbyl.

In various embodiments of the present invention, R is chosen from: $(C_{10}-C_{20})$hydrocarbyl, $(C_{10}-C_{19})$hydrocarbyl, $(C_{10}-C_{18})$hydrocarbyl, $(C_{10}-C_{17})$hydrocarbyl, $(C_{10}-C_{16})$hydrocarbyl, $(C_{10}-C_{15})$hydrocarbyl, $(C_{10}-C_{14})$hydrocarbyl, $(C_{10}-C_{13})$hydrocarbyl, $(C_{10}-C_{12})$hydrocarbyl, and $(C_{10}-C_{11})$hydrocarbyl.

In various embodiments of the present invention, R is chosen from: $(C_{11}-C_{20})$hydrocarbyl, $(C_{11}-C_{19})$hydrocarbyl, $(C_{11}-C_{18})$hydrocarbyl, $(C_{11}-C_{17})$hydrocarbyl, $(C_{11}-C_{16})$hydrocarbyl, $(C_{11}-C_{15})$hydrocarbyl, $(C_{11}-C_{14})$hydrocarbyl, $(C_{11}-C_{13})$hydrocarbyl, and $(C_{11}-C_{12})$hydrocarbyl.

In various embodiments of the present invention, R is chosen from: $(C_{12}-C_{20})$hydrocarbyl, $(C_{12}-C_{19})$hydrocarbyl, $(C_{12}-C_{18})$hydrocarbyl, $(C_{12}-C_{17})$hydrocarbyl, $(C_{12}-C_{16})$hydrocarbyl, $(C_{12}-C_{15})$hydrocarbyl, $(C_{12}-C_{14})$hydrocarbyl, and $(C_{12}-C_{13})$hydrocarbyl.

In various embodiments of the present invention, R is chosen from: $(C_{13}-C_{20})$hydrocarbyl, $(C_{13}-C_{19})$hydrocarbyl, $(C_{13}-C_{18})$hydrocarbyl, $(C_{13}-C_{17})$hydrocarbyl, $(C_{13}-C_{16})$hydrocarbyl, $(C_{13}-C_{15})$hydrocarbyl, and $(C_{13}-C_{14})$hydrocarbyl.

In various embodiments of the present invention, R is chosen from: $(C_{14}-C_{20})$hydrocarbyl, $(C_{14}-C_{19})$hydrocarbyl, $(C_{14}-C_{18})$hydrocarbyl, $(C_{14}-C_{17})$hydrocarbyl, $(C_{14}-C_{16})$hydrocarbyl, and $(C_{14}-C_{15})$hydrocarbyl.

In various embodiments of the present invention, R is chosen from: $(C_{15}-C_{20})$hydrocarbyl, $(C_{15}-C_{19})$hydrocarbyl, $(C_{15}-C_{18})$hydrocarbyl, $(C_{15}-C_{17})$hydrocarbyl, and $(C_{15}-C_{16})$hydrocarbyl.

In various embodiments of the present invention, R is chosen from: $(C_{16}-C_{20})$hydrocarbyl, $(C_{16}-C_{19})$hydrocarbyl, $(C_{16}-C_{18})$hydrocarbyl, and $(C_{16}-C_{17})$hydrocarbyl.

In various embodiments of the present invention, R is chosen from: $(C_{17}-C_{20})$hydrocarbyl, $(C_{17}-C_{19})$hydrocarbyl, and $(C_{17}-C_{18})$hydrocarbyl.

In various embodiments of the present invention, R is $(C_{18}-C_{20})$hydrocarbyl or $(C_{18}-C_{19})$hydrocarbyl.

In various embodiments of the present invention, R is $(C_{19}-C_{20})$hydrocarbyl.

In various embodiments of the present invention, R is chosen from: $(C_{20})$hydrocarbyl, $(C_{19})$hydrocarbyl, $(C_{18})$hydrocarbyl, $(C_{17})$hydrocarbyl, $(C_{16})$hydrocarbyl, $(C_{15})$hydrocarbyl, $(C_{14})$hydrocarbyl, $(C_{13})$hydrocarbyl, $(C_{12})$hydrocarbyl, $(C_{11})$hydrocarbyl, $(C_{10})$hydrocarbyl, $(C_9)$hydrocarbyl, ($C_8$)hydrocarbyl, ($C_7$)hydrocarbyl, ($C_6$)hydrocarbyl, ($C_5$)hydrocarbyl, ($C_4$)hydrocarbyl, and ($C_3$)hydrocarbyl.

In some embodiments of the present invention, R is chosen from: aliphatic ($C_1$-$C_{20}$)hydrocarbyl optionally substituted with one or two phenyl groups with the proviso that R contains twenty carbons or less, aliphatic ($C_1$-$C_{19}$)hydrocarbyl optionally substituted with one or two phenyl groups with the proviso that R contains twenty carbons or less, aliphatic ($C_1$-$C_{18}$)hydrocarbyl optionally substituted with one or two phenyl groups with the proviso that R contains twenty carbons or less, aliphatic ($C_1$-$C_{17}$)hydrocarbyl optionally substituted with one or two phenyl groups with the proviso that R contains twenty carbons or less, aliphatic ($C_1$-$C_{16}$)hydrocarbyl optionally substituted with one or two phenyl groups with the proviso that R contains twenty carbons or less, aliphatic ($C_1$-$C_{15}$)hydrocarbyl optionally substituted with one or two phenyl groups with the proviso that R contains twenty carbons or less, aliphatic ($C_1$-$C_{14}$) hydrocarbyl optionally substituted with one or two phenyl groups with the proviso that R contains twenty carbons or less, aliphatic ($C_1$-$C_{13}$)hydrocarbyl optionally substituted with one or two phenyl groups with the proviso that R contains twenty carbons or less, aliphatic ($C_1$-$C_{12}$)hydrocarbyl optionally substituted with one or two phenyl groups with the proviso that R contains twenty carbons or less, aliphatic ($C_1$-$C_{11}$)hydrocarbyl optionally substituted with one or two phenyl groups with the proviso that R contains twenty carbons or less, aliphatic ($C_1$-$C_{10}$)hydrocarbyl optionally substituted with one or two phenyl groups with the proviso that R contains twenty carbons or less, aliphatic ($C_1$-$C_9$)hydrocarbyl optionally substituted with one or two phenyl groups with the proviso that R contains twenty carbons or less, aliphatic ($C_1$-$C_8$)hydrocarbyl optionally substituted with one or two phenyl groups, aliphatic ($C_1$-$C_7$)hydrocarbyl optionally substituted with one or two phenyl groups, aliphatic ($C_1$-$C_6$)hydrocarbyl optionally substituted with one or two phenyl groups, aliphatic ($C_1$-$C_5$) hydrocarbyl optionally substituted with one or two phenyl groups, aliphatic ($C_1$-$C_4$)hydrocarbyl optionally substituted with one or two phenyl groups, and aliphatic ($C_1$-$C_3$) hydrocarbyl optionally substituted with one or two phenyl groups.

In various embodiments of the present invention, R is chosen from: aliphatic ($C_2$-$C_{20}$)hydrocarbyl optionally substituted with one or two phenyl groups with the proviso that R contains twenty carbons or less, aliphatic ($C_2$-$C_{19}$)hydrocarbyl optionally substituted with one or two phenyl groups with the proviso that R contains twenty carbons or less, aliphatic ($C_2$-$C_{18}$)hydrocarbyl optionally substituted with one or two phenyl groups with the proviso that R contains twenty carbons or less, aliphatic ($C_2$-$C_{17}$)hydrocarbyl optionally substituted with one or two phenyl groups with the proviso that R contains twenty carbons or less, aliphatic ($C_2$-$C_{16}$)hydrocarbyl optionally substituted with one or two phenyl groups with the proviso that R contains twenty carbons or less, aliphatic ($C_2$-$C_{15}$)hydrocarbyl optionally substituted with one or two phenyl groups with the proviso that R contains twenty carbons or less, aliphatic ($C_2$-$C_{14}$) hydrocarbyl optionally substituted with one or two phenyl groups with the proviso that R contains twenty carbons or less, aliphatic ($C_2$-$C_{13}$)hydrocarbyl optionally substituted with one or two phenyl groups with the proviso that R contains twenty carbons or less, aliphatic ($C_2$-$C_{12}$)hydrocarbyl optionally substituted with one or two phenyl groups with the proviso that R contains twenty carbons or less, aliphatic ($C_2$-$C_{11}$)hydrocarbyl optionally substituted with one or two phenyl groups with the proviso that R contains twenty carbons or less, aliphatic ($C_2$-$C_{10}$)hydrocarbyl optionally substituted with one or two phenyl groups with the proviso that R contains twenty carbons or less, aliphatic ($C_2$-$C_9$)hydrocarbyl optionally substituted with one or two phenyl groups with the proviso that R contains twenty carbons or less, aliphatic ($C_2$-$C_8$)hydrocarbyl optionally substituted with one or two phenyl groups, aliphatic ($C_2$-$C_7$)hydrocarbyl optionally substituted with one or two phenyl groups, aliphatic ($C_2$-$C_6$)hydrocarbyl optionally substituted with one or two phenyl groups, aliphatic ($C_2$-$C_5$) hydrocarbyl optionally substituted with one or two phenyl groups, aliphatic ($C_2$-$C_4$)hydrocarbyl optionally substituted with one or two phenyl groups, and aliphatic ($C_2$-$C_3$) hydrocarbyl optionally substituted with one or two phenyl groups.

In various embodiments of the present invention, R is chosen from: aliphatic ($C_3$-$C_{20}$)hydrocarbyl optionally substituted with one or two phenyl groups with the proviso that R contains twenty carbons or less, aliphatic ($C_3$-$C_{19}$)hydrocarbyl optionally substituted with one or two phenyl groups with the proviso that R contains twenty carbons or less, aliphatic ($C_3$-$C_{18}$)hydrocarbyl optionally substituted with one or two phenyl groups with the proviso that R contains twenty carbons or less, aliphatic ($C_3$-$C_{17}$)hydrocarbyl optionally substituted with one or two phenyl groups with the proviso that R contains twenty carbons or less, aliphatic ($C_3$-$C_{16}$)hydrocarbyl optionally substituted with one or two phenyl groups with the proviso that R contains twenty carbons or less, aliphatic ($C_3$-$C_{15}$)hydrocarbyl optionally substituted with one or two phenyl groups with the proviso that R contains twenty carbons or less, aliphatic ($C_3$-$C_{14}$) hydrocarbyl optionally substituted with one or two phenyl groups with the proviso that R contains twenty carbons or less, aliphatic ($C_3$-$C_{13}$)hydrocarbyl optionally substituted with one or two phenyl groups with the proviso that R contains twenty carbons or less, aliphatic ($C_3$-$C_{12}$)hydrocarbyl optionally substituted with one or two phenyl groups with the proviso that R contains twenty carbons or less, aliphatic ($C_3$-$C_{11}$)hydrocarbyl optionally substituted with one or two phenyl groups with the proviso that R contains twenty carbons or less, aliphatic ($C_3$-$C_{10}$)hydrocarbyl optionally substituted with one or two phenyl groups with the proviso that R contains twenty carbons or less, aliphatic ($C_3$-$C_9$)hydrocarbyl optionally substituted with one or two phenyl groups with the proviso that R contains twenty carbons or less, aliphatic ($C_3$-$C_8$)hydrocarbyl optionally substituted with one or two phenyl groups, aliphatic ($C_3$-$C_7$)hydrocarbyl optionally substituted with one or two phenyl groups, aliphatic ($C_3$-$C_6$)hydrocarbyl optionally substituted with one or two phenyl groups, aliphatic ($C_3$-$C_5$) hydrocarbyl optionally substituted with one or two phenyl groups, aliphatic ($C_3$-$C_4$)hydrocarbyl optionally substituted with one or two phenyl groups.

In various embodiments of the present invention, R is chosen from: aliphatic ($C_4$-$C_{20}$)hydrocarbyl optionally substituted with one or two phenyl groups with the proviso that R contains twenty carbons or less, aliphatic ($C_4$-$C_{19}$)hydrocarbyl optionally substituted with one or two phenyl groups with the proviso that R contains twenty carbons or less, aliphatic ($C_4$-$C_{18}$)hydrocarbyl optionally substituted with one or two phenyl groups with the proviso that R contains twenty carbons or less, aliphatic ($C_4$-$C_{17}$)hydrocarbyl optionally substituted with one or two phenyl groups with the proviso that R contains twenty carbons or less, aliphatic ($C_4$-$C_{16}$)hydrocarbyl optionally substituted with one or two phenyl groups with the proviso that R contains twenty carbons or less, aliphatic ($C_4$-$C_{15}$)hydrocarbyl optionally substituted with one or two phenyl groups with the proviso that R contains twenty carbons or less, aliphatic $(C_4-C_{14})$ hydrocarbyl optionally substituted with one or two phenyl groups with the proviso that R contains twenty carbons or less, aliphatic $(C_4-C_{13})$hydrocarbyl optionally substituted with one or two phenyl groups with the proviso that R contains twenty carbons or less, aliphatic $(C_4-C_{12})$hydrocarbyl optionally substituted with one or two phenyl groups with the proviso that R contains twenty carbons or less, aliphatic $(C_4-C_{11})$hydrocarbyl optionally substituted with one or two phenyl groups with the proviso that R contains twenty carbons or less, aliphatic $(C_4-C_{10})$hydrocarbyl optionally substituted with one or two phenyl groups with the proviso that R contains twenty carbons or less, aliphatic $(C_4-C_9)$hydrocarbyl optionally substituted with one or two phenyl groups with the proviso that R contains twenty carbons or less, aliphatic $(C_4-C_8)$hydrocarbyl optionally substituted with one or two phenyl groups, aliphatic $(C_4-C_7)$hydrocarbyl optionally substituted with one or two phenyl groups, aliphatic $(C_4-C_6)$hydrocarbyl optionally substituted with one or two phenyl groups, and aliphatic $(C_4-C_5)$ hydrocarbyl optionally substituted with one or two phenyl groups.

In various embodiments of the present invention, R is chosen from: aliphatic $(C_5-C_{20})$hydrocarbyl optionally substituted with one or two phenyl groups with the proviso that R contains twenty carbons or less, aliphatic $(C_5-C_{19})$hydrocarbyl optionally substituted with one or two phenyl groups with the proviso that R contains twenty carbons or less, aliphatic $(C_5-C_{18})$hydrocarbyl optionally substituted with one or two phenyl groups with the proviso that R contains twenty carbons or less, aliphatic $(C_5-C_{17})$hydrocarbyl optionally substituted with one or two phenyl groups with the proviso that R contains twenty carbons or less, aliphatic $(C_5-C_{16})$hydrocarbyl optionally substituted with one or two phenyl groups with the proviso that R contains twenty carbons or less, aliphatic $(C_5-C_{15})$hydrocarbyl optionally substituted with one or two phenyl groups with the proviso that R contains twenty carbons or less, aliphatic $(C_5-C_{14})$ hydrocarbyl optionally substituted with one or two phenyl groups with the proviso that R contains twenty carbons or less, aliphatic $(C_5-C_{13})$hydrocarbyl optionally substituted with one or two phenyl groups with the proviso that R contains twenty carbons or less, aliphatic $(C_5-C_{12})$hydrocarbyl optionally substituted with one or two phenyl groups with the proviso that R contains twenty carbons or less, aliphatic $(C_5-C_{11})$hydrocarbyl optionally substituted with one or two phenyl groups with the proviso that R contains twenty carbons or less, aliphatic $(C_5-C_{10})$hydrocarbyl optionally substituted with one or two phenyl groups with the proviso that R contains twenty carbons or less, aliphatic $(C_5-C_9)$hydrocarbyl optionally substituted with one or two phenyl groups with the proviso that R contains twenty carbons or less, aliphatic $(C_5-C_8)$hydrocarbyl optionally substituted with one or two phenyl groups, aliphatic $(C_5-C_7)$hydrocarbyl optionally substituted with one or two phenyl groups, and aliphatic $(C_5-C_6)$hydrocarbyl optionally substituted with one or two phenyl groups.

In various embodiments of the present invention, R is chosen from: aliphatic $(C_6-C_{20})$hydrocarbyl optionally substituted with one or two phenyl groups with the proviso that R contains twenty carbons or less, aliphatic $(C_6-C_{19})$hydrocarbyl optionally substituted with one or two phenyl groups with the proviso that R contains twenty carbons or less, aliphatic $(C_6-C_{18})$hydrocarbyl optionally substituted with one or two phenyl groups with the proviso that R contains twenty carbons or less, aliphatic $(C_6-C_{17})$hydrocarbyl optionally substituted with one or two phenyl groups with the proviso that R contains twenty carbons or less, aliphatic $(C_6-C_{16})$hydrocarbyl optionally substituted with one or two phenyl groups with the proviso that R contains twenty carbons or less, aliphatic $(C_6-C_{15})$hydrocarbyl optionally substituted with one or two phenyl groups with the proviso that R contains twenty carbons or less, aliphatic $(C_6-C_{14})$ hydrocarbyl optionally substituted with one or two phenyl groups with the proviso that R contains twenty carbons or less, aliphatic $(C_6-C_{13})$hydrocarbyl optionally substituted with one or two phenyl groups with the proviso that R contains twenty carbons or less, aliphatic $(C_6-C_{12})$hydrocarbyl optionally substituted with one or two phenyl groups with the proviso that R contains twenty carbons or less, aliphatic $(C_6-C_{11})$hydrocarbyl optionally substituted with one or two phenyl groups with the proviso that R contains twenty carbons or less, aliphatic $(C_6-C_{10})$hydrocarbyl optionally substituted with one or two phenyl groups with the proviso that R contains twenty carbons or less, aliphatic $(C_6-C_9)$hydrocarbyl optionally substituted with one or two phenyl groups with the proviso that R contains twenty carbons or less, aliphatic $(C_6-C_8)$hydrocarbyl optionally substituted with one or two phenyl groups, and aliphatic $(C_6-C_7)$hydrocarbyl optionally substituted with one or two phenyl groups.

In various embodiments of the present invention, R is chosen from: aliphatic $(C_7-C_{20})$hydrocarbyl optionally substituted with one or two phenyl groups with the proviso that R contains twenty carbons or less, aliphatic $(C_7-C_{19})$hydrocarbyl optionally substituted with one or two phenyl groups with the proviso that R contains twenty carbons or less, aliphatic $(C_7-C_{18})$hydrocarbyl optionally substituted with one or two phenyl groups with the proviso that R contains twenty carbons or less, aliphatic $(C_7-C_{17})$hydrocarbyl optionally substituted with one or two phenyl groups with the proviso that R contains twenty carbons or less, aliphatic $(C_7-C_{16})$hydrocarbyl optionally substituted with one or two phenyl groups with the proviso that R contains twenty carbons or less, aliphatic $(C_7-C_{15})$hydrocarbyl optionally substituted with one or two phenyl groups with the proviso that R contains twenty carbons or less, aliphatic $(C_7-C_{14})$ hydrocarbyl optionally substituted with one or two phenyl groups with the proviso that R contains twenty carbons or less, aliphatic $(C_7-C_{13})$hydrocarbyl optionally substituted with one or two phenyl groups with the proviso that R contains twenty carbons or less, aliphatic $(C_7-C_{12})$hydrocarbyl optionally substituted with one or two phenyl groups with the proviso that R contains twenty carbons or less, aliphatic $(C_7-C_{11})$hydrocarbyl optionally substituted with one or two phenyl groups with the proviso that R contains twenty carbons or less, aliphatic $(C_7-C_{10})$hydrocarbyl optionally substituted with one or two phenyl groups with the proviso that R contains twenty carbons or less, aliphatic $(C_7-C_9)$hydrocarbyl optionally substituted with one or two phenyl groups with the proviso that R contains twenty carbons or less, and aliphatic $(C_7-C_8)$hydrocarbyl optionally substituted with one or two phenyl groups.

In various embodiments of the present invention, R is chosen from: aliphatic $(C_8-C_{20})$hydrocarbyl optionally substituted with one or two phenyl groups with the proviso that R contains twenty carbons or less, aliphatic $(C_8-C_{19})$hydrocarbyl optionally substituted with one or two phenyl groups with the proviso that R contains twenty carbons or less, aliphatic $(C_8-C_{18})$hydrocarbyl optionally substituted with one or two phenyl groups with the proviso that R contains twenty carbons or less, aliphatic $(C_8-C_{17})$hydrocarbyl optionally substituted with one or two phenyl groups with the proviso that R contains twenty carbons or less, aliphatic ($C_8$-$C_{16}$)hydrocarbyl optionally substituted with one or two phenyl groups with the proviso that R contains twenty carbons or less, aliphatic ($C_8$-$C_{15}$)hydrocarbyl optionally substituted with one or two phenyl groups with the proviso that R contains twenty carbons or less, aliphatic ($C_8$-$C_{14}$) hydrocarbyl optionally substituted with one or two phenyl groups with the proviso that R contains twenty carbons or less, aliphatic ($C_8$-$C_{13}$)hydrocarbyl optionally substituted with one or two phenyl groups with the proviso that R contains twenty carbons or less, aliphatic ($C_8$-$C_{12}$)hydrocarbyl optionally substituted with one or two phenyl groups with the proviso that R contains twenty carbons or less, aliphatic ($C_8$-$C_{11}$)hydrocarbyl optionally substituted with one or two phenyl groups with the proviso that R contains twenty carbons or less, aliphatic ($C_8$-$C_{10}$)hydrocarbyl optionally substituted with one or two phenyl groups with the proviso that R contains twenty carbons or less, and aliphatic ($C_8$-$C_9$)hydrocarbyl optionally substituted with one or two phenyl groups with the proviso that R contains twenty carbons or less.

In various embodiments of the present invention, R is chosen from: aliphatic ($C_9$-$C_{20}$)hydrocarbyl optionally substituted with a phenyl group with the proviso that R contains twenty carbons or less, aliphatic ($C_9$-$C_{19}$)hydrocarbyl optionally substituted with a phenyl group with the proviso that R contains twenty carbons or less, aliphatic ($C_9$-$C_{18}$) hydrocarbyl optionally substituted with a phenyl group with the proviso that R contains twenty carbons or less, aliphatic ($C_9$-$C_{17}$)hydrocarbyl optionally substituted with a phenyl group with the proviso that R contains twenty carbons or less, aliphatic ($C_9$-$C_{16}$)hydrocarbyl optionally substituted with a phenyl group with the proviso that R contains twenty carbons or less, aliphatic ($C_9$-$C_{15}$)hydrocarbyl optionally substituted with a phenyl group with the proviso that R contains twenty carbons or less, aliphatic ($C_9$-$C_{14}$)hydrocarbyl optionally substituted with a phenyl group, aliphatic ($C_9$-$C_{13}$)hydrocarbyl optionally substituted with a phenyl group, aliphatic ($C_9$-$C_{12}$)hydrocarbyl optionally substituted with a phenyl group, aliphatic ($C_9$-$C_{11}$)hydrocarbyl optionally substituted with a phenyl group, and aliphatic ($C_9$-$C_{10}$) hydrocarbyl optionally substituted with a phenyl group.

In various embodiments of the present invention, R is chosen from: aliphatic ($C_{10}$-$C_{20}$)hydrocarbyl optionally substituted with a phenyl group with the proviso that R contains twenty carbons or less, aliphatic ($C_{10}$-$C_{19}$)hydrocarbyl optionally substituted with a phenyl group with the proviso that R contains twenty carbons or less, aliphatic ($C_{10}$-$C_{18}$) hydrocarbyl optionally substituted with a phenyl group with the proviso that R contains twenty carbons or less, aliphatic ($C_{10}$-$C_{17}$)hydrocarbyl optionally substituted with a phenyl group with the proviso that R contains twenty carbons or less, aliphatic ($C_{10}$-$C_{16}$)hydrocarbyl optionally substituted with a phenyl group with the proviso that R contains twenty carbons or less, aliphatic ($C_{10}$-$C_{15}$)hydrocarbyl optionally substituted with a phenyl group with the proviso that R contains twenty carbons or less, aliphatic ($C_{10}$-$C_{14}$)hydrocarbyl optionally substituted with a phenyl group, aliphatic ($C_{10}$-$C_{13}$)hydrocarbyl optionally substituted with a phenyl group, aliphatic ($C_{10}$-$C_{12}$)hydrocarbyl optionally substituted with a phenyl group, and aliphatic ($C_{10}$-$C_{11}$)hydrocarbyl optionally substituted with a phenyl group.

In various embodiments of the present invention, R is chosen from: aliphatic ($C_{11}$-$C_{20}$)hydrocarbyl optionally substituted with a phenyl group with the proviso that R contains twenty carbons or less, aliphatic ($C_{11}$-$C_{19}$)hydrocarbyl optionally substituted with a phenyl group with the proviso that R contains twenty carbons or less, aliphatic ($C_{11}$-$C_{18}$) hydrocarbyl optionally substituted with a phenyl group with the proviso that R contains twenty carbons or less, aliphatic ($C_{11}$-$C_{17}$)hydrocarbyl optionally substituted with a phenyl group with the proviso that R contains twenty carbons or less, aliphatic ($C_{11}$-$C_{16}$)hydrocarbyl optionally substituted with a phenyl group with the proviso that R contains twenty carbons or less, aliphatic ($C_{11}$-$C_{15}$)hydrocarbyl optionally substituted with a phenyl group with the proviso that R contains twenty carbons or less, aliphatic ($C_{11}$-$C_{14}$)hydrocarbyl optionally substituted with a phenyl group, aliphatic ($C_{11}$-$C_{13}$)hydrocarbyl optionally substituted with a phenyl group, and aliphatic ($C_{11}$-$C_{12}$)hydrocarbyl optionally substituted with a phenyl group.

In various embodiments of the present invention, R is chosen from: aliphatic ($C_{12}$-$C_{20}$)hydrocarbyl optionally substituted with a phenyl group with the proviso that R contains twenty carbons or less, aliphatic ($C_{12}$-$C_{19}$)hydrocarbyl optionally substituted with a phenyl group with the proviso that R contains twenty carbons or less, aliphatic ($C_{12}$-$C_{18}$) hydrocarbyl optionally substituted with a phenyl group with the proviso that R contains twenty carbons or less, aliphatic ($C_{12}$-$C_{17}$)hydrocarbyl optionally substituted with a phenyl group with the proviso that R contains twenty carbons or less, aliphatic ($C_{12}$-$C_{16}$)hydrocarbyl optionally substituted with a phenyl group with the proviso that R contains twenty carbons or less, aliphatic ($C_{12}$-$C_{15}$)hydrocarbyl optionally substituted with a phenyl group with the proviso that R contains twenty carbons or less, aliphatic ($C_{12}$-$C_{14}$)hydrocarbyl optionally substituted with a phenyl group, and aliphatic ($C_{12}$-$C_{13}$)hydrocarbyl optionally substituted with a phenyl group.

In various embodiments of the present invention, R is chosen from: aliphatic ($C_{13}$-$C_{20}$)hydrocarbyl optionally substituted with a phenyl group with the proviso that R contains twenty carbons or less, aliphatic ($C_{13}$-$C_{19}$)hydrocarbyl optionally substituted with a phenyl group with the proviso that R contains twenty carbons or less, aliphatic ($C_{13}$-$C_{18}$) hydrocarbyl optionally substituted with a phenyl group with the proviso that R contains twenty carbons or less, aliphatic ($C_{13}$-$C_{17}$)hydrocarbyl optionally substituted with a phenyl group with the proviso that R contains twenty carbons or less, aliphatic ($C_{13}$-$C_{16}$)hydrocarbyl optionally substituted with a phenyl group with the proviso that R contains twenty carbons or less, aliphatic ($C_{13}$-$C_{15}$)hydrocarbyl optionally substituted with a phenyl group with the proviso that R contains twenty carbons or less, and aliphatic ($C_{13}$-$C_{14}$) hydrocarbyl optionally substituted with a phenyl group.

In various embodiments of the present invention, R is chosen from: aliphatic ($C_{14}$-$C_{20}$)hydrocarbyl optionally substituted with a phenyl group with the proviso that R contains twenty carbons or less, aliphatic ($C_{14}$-$C_{19}$)hydrocarbyl optionally substituted with a phenyl group with the proviso that R contains twenty carbons or less, aliphatic ($C_{14}$-$C_{18}$) hydrocarbyl optionally substituted with a phenyl group with the proviso that R contains twenty carbons or less, aliphatic ($C_{14}$-$C_{17}$)hydrocarbyl optionally substituted with a phenyl group with the proviso that R contains twenty carbons or less, aliphatic ($C_{14}$-$C_{16}$)hydrocarbyl optionally substituted with a phenyl group with the proviso that R contains twenty carbons or less, and aliphatic ($C_{14}$-$C_{15}$)hydrocarbyl optionally substituted with a phenyl group with the proviso that R contains twenty carbons or less.

In various embodiments of the present invention, R is chosen from: aliphatic ($C_{15}$-$C_{20}$)hydrocarbyl, aliphatic ($C_{15}$-$C_{19}$)hydrocarbyl, aliphatic ($C_{15}$-$C_{18}$)hydrocarbyl, aliphatic ($C_{15}$-$C_{17}$)hydrocarbyl, and aliphatic ($C_{15}$-$C_{16}$)hydrocarbyl.

In various embodiments of the present invention, R is chosen from: aliphatic ($C_{16}$-$C_{20}$)hydrocarbyl, aliphatic ($C_{16}$-$C_{19}$)hydrocarbyl, aliphatic ($C_{16}$-$C_{18}$)hydrocarbyl, and aliphatic ($C_{16}$-$C_{17}$)hydrocarbyl.

In various embodiments of the present invention, R is chosen from: aliphatic ($C_{17}$-$C_{20}$)hydrocarbyl, aliphatic ($C_{17}$-$C_{19}$)hydrocarbyl, and aliphatic ($C_{17}$-$C_{18}$)hydrocarbyl.

In various embodiments of the present invention, R is aliphatic ($C_{18}$-$C_{20}$)hydrocarbyl or aliphatic ($C_{18}$-$C_{19}$)hydrocarbyl.

In various embodiments of the present invention, R is aliphatic ($C_{19}$-$C_{20}$)hydrocarbyl.

In various embodiments of the present invention, R is chosen from: aliphatic ($C_{20}$)hydrocarbyl, aliphatic ($C_{19}$)hydrocarbyl, aliphatic ($C_{18}$)hydrocarbyl, aliphatic ($C_{17}$)hydrocarbyl, aliphatic ($C_{16}$)hydrocarbyl, aliphatic ($C_{15}$)hydrocarbyl, aliphatic ($C_{14}$)hydrocarbyl optionally substituted with a phenyl group, aliphatic ($C_{13}$)hydrocarbyl optionally substituted with a phenyl group, aliphatic ($C_{12}$)hydrocarbyl optionally substituted with a phenyl group, aliphatic ($C_{11}$)hydrocarbyl optionally substituted with a phenyl group, aliphatic ($C_{10}$)hydrocarbyl optionally substituted with a phenyl group, aliphatic ($C_{9}$)hydrocarbyl optionally substituted with a phenyl group, aliphatic ($C_{8}$)hydrocarbyl optionally substituted with one or two phenyl groups, aliphatic ($C_{7}$)hydrocarbyl optionally substituted with one or two phenyl groups, aliphatic ($C_{6}$)hydrocarbyl optionally substituted with one or two phenyl groups, aliphatic ($C_{5}$)hydrocarbyl optionally substituted with one or two phenyl groups, aliphatic ($C_{4}$)hydrocarbyl optionally substituted with one or two phenyl groups, and aliphatic ($C_{3}$)hydrocarbyl optionally substituted with one or two phenyl groups.

In some embodiments of the present invention, R is chosen from: ($C_1$-$C_{20}$)alkyl optionally substituted with one or two phenyl groups with the proviso that R contains twenty carbons or less, ($C_1$-$C_{19}$)alkyl optionally substituted with one or two phenyl groups with the proviso that R contains twenty carbons or less, ($C_1$-$C_{18}$)alkyl optionally substituted with one or two phenyl groups with the proviso that R contains twenty carbons or less, ($C_1$-$C_{17}$)alkyl optionally substituted with one or two phenyl groups with the proviso that R contains twenty carbons or less, ($C_1$-$C_{16}$)alkyl optionally substituted with one or two phenyl groups with the proviso that R contains twenty carbons or less, ($C_1$-$C_{15}$)alkyl optionally substituted with one or two phenyl groups with the proviso that R contains twenty carbons or less, ($C_1$-$C_{14}$)alkyl optionally substituted with one or two phenyl groups with the proviso that R contains twenty carbons or less, ($C_1$-$C_{13}$)alkyl optionally substituted with one or two phenyl groups with the proviso that R contains twenty carbons or less, ($C_1$-$C_{12}$)alkyl optionally substituted with one or two phenyl groups with the proviso that R contains twenty carbons or less, ($C_1$-$C_{11}$)alkyl optionally substituted with one or two phenyl groups with the proviso that R contains twenty carbons or less, ($C_1$-$C_{10}$)alkyl optionally substituted with one or two phenyl groups with the proviso that R contains twenty carbons or less, ($C_1$-$C_{9}$)alkyl optionally substituted with one or two phenyl groups with the proviso that R contains twenty carbons or less, ($C_1$-$C_{8}$)alkyl optionally substituted with one or two phenyl groups, ($C_1$-$C_{7}$)alkyl optionally substituted with one or two phenyl groups, ($C_1$-$C_{6}$)alkyl optionally substituted with one or two phenyl groups, ($C_1$-$C_{5}$)alkyl optionally substituted with one or two phenyl groups, ($C_1$-$C_{4}$)alkyl optionally substituted with one or two phenyl groups, and ($C_1$-$C_{3}$)alkyl optionally substituted with one or two phenyl groups.

In various embodiments of the present invention, R is chosen from: ($C_2$-$C_{20}$)alkyl optionally substituted with one or two phenyl groups with the proviso that R contains twenty carbons or less, ($C_2$-$C_{19}$)alkyl optionally substituted with one or two phenyl groups with the proviso that R contains twenty carbons or less, ($C_2$-$C_{18}$)alkyl optionally substituted with one or two phenyl groups with the proviso that R contains twenty carbons or less, ($C_2$-$C_{17}$)alkyl optionally substituted with one or two phenyl groups with the proviso that R contains twenty carbons or less, ($C_2$-$C_{16}$)alkyl optionally substituted with one or two phenyl groups with the proviso that R contains twenty carbons or less, ($C_2$-$C_{15}$)alkyl optionally substituted with one or two phenyl groups with the proviso that R contains twenty carbons or less, ($C_2$-$C_{14}$)alkyl optionally substituted with one or two phenyl groups with the proviso that R contains twenty carbons or less, ($C_2$-$C_{13}$)alkyl optionally substituted with one or two phenyl groups with the proviso that R contains twenty carbons or less, ($C_2$-$C_{12}$)alkyl optionally substituted with one or two phenyl groups with the proviso that R contains twenty carbons or less, ($C_2$-$C_{11}$)alkyl optionally substituted with one or two phenyl groups with the proviso that R contains twenty carbons or less, ($C_2$-$C_{10}$)alkyl optionally substituted with one or two phenyl groups with the proviso that R contains twenty carbons or less, ($C_2$-$C_{9}$)alkyl optionally substituted with one or two phenyl groups with the proviso that R contains twenty carbons or less, ($C_2$-$C_{8}$)alkyl optionally substituted with one or two phenyl groups, ($C_2$-$C_{7}$)alkyl optionally substituted with one or two phenyl groups, ($C_2$-$C_{6}$)alkyl optionally substituted with one or two phenyl groups, ($C_2$-$C_{5}$)alkyl optionally substituted with one or two phenyl groups, ($C_2$-$C_{4}$)alkyl optionally substituted with one or two phenyl groups, and ($C_2$-$C_{3}$)alkyl optionally substituted with one or two phenyl groups.

In various embodiments of the present invention, R is chosen from: ($C_3$-$C_{20}$)alkyl optionally substituted with one or two phenyl groups with the proviso that R contains twenty carbons or less, ($C_3$-$C_{19}$)alkyl optionally substituted with one or two phenyl groups with the proviso that R contains twenty carbons or less, ($C_3$-$C_{18}$)alkyl optionally substituted with one or two phenyl groups with the proviso that R contains twenty carbons or less, ($C_3$-$C_{17}$)alkyl optionally substituted with one or two phenyl groups with the proviso that R contains twenty carbons or less, ($C_3$-$C_{16}$)alkyl optionally substituted with one or two phenyl groups with the proviso that R contains twenty carbons or less, ($C_3$-$C_{15}$)alkyl optionally substituted with one or two phenyl groups with the proviso that R contains twenty carbons or less, ($C_3$-$C_{14}$)alkyl optionally substituted with one or two phenyl groups with the proviso that R contains twenty carbons or less, ($C_3$-$C_{13}$)alkyl optionally substituted with one or two phenyl groups with the proviso that R contains twenty carbons or less, ($C_3$-$C_{12}$)alkyl optionally substituted with one or two phenyl groups with the proviso that R contains twenty carbons or less, ($C_3$-$C_{11}$)alkyl optionally substituted with one or two phenyl groups with the proviso that R contains twenty carbons or less, ($C_3$-$C_{10}$)alkyl optionally substituted with one or two phenyl groups with the proviso that R contains twenty carbons or less, ($C_3$-$C_{9}$)alkyl optionally substituted with one or two phenyl groups with the proviso that R contains twenty carbons or less, ($C_3$-$C_{8}$)alkyl optionally substituted with one or two phenyl groups, ($C_3$-$C_{7}$)alkyl optionally substituted with one or two phenyl groups, ($C_3$-$C_{6}$)alkyl optionally substituted with one or two phenyl groups, ($C_3$-$C_{5}$)alkyl optionally substituted with one or two phenyl groups, ($C_3$-$C_{4}$)alkyl optionally substituted with one or two phenyl groups.

In various embodiments of the present invention, R is chosen from: $(C_4-C_{20})$alkyl optionally substituted with one or two phenyl groups with the proviso that R contains twenty carbons or less, $(C_4-C_{19})$alkyl optionally substituted with one or two phenyl groups with the proviso that R contains twenty carbons or less, $(C_4-C_{18})$alkyl optionally substituted with one or two phenyl groups with the proviso that R contains twenty carbons or less, $(C_4-C_{17})$alkyl optionally substituted with one or two phenyl groups with the proviso that R contains twenty carbons or less, $(C_4-C_{16})$alkyl optionally substituted with one or two phenyl groups with the proviso that R contains twenty carbons or less, $(C_4-C_{15})$alkyl optionally substituted with one or two phenyl groups with the proviso that R contains twenty carbons or less, $(C_4-C_{14})$alkyl optionally substituted with one or two phenyl groups with the proviso that R contains twenty carbons or less, $(C_4-C_{13})$alkyl optionally substituted with one or two phenyl groups with the proviso that R contains twenty carbons or less, $(C_4-C_{12})$alkyl optionally substituted with one or two phenyl groups with the proviso that R contains twenty carbons or less, $(C_4-C_{11})$alkyl optionally substituted with one or two phenyl groups with the proviso that R contains twenty carbons or less, $(C_4-C_{10})$alkyl optionally substituted with one or two phenyl groups with the proviso that R contains twenty carbons or less, $(C_4-C_9)$alkyl optionally substituted with one or two phenyl groups with the proviso that R contains twenty carbons or less, $(C_4-C_8)$alkyl optionally substituted with one or two phenyl groups, $(C_4-C_7)$alkyl optionally substituted with one or two phenyl groups, $(C_4-C_6)$alkyl optionally substituted with one or two phenyl groups, and $(C_4-C_5)$alkyl optionally substituted with one or two phenyl groups.

In various embodiments of the present invention, R is chosen from: $(C_5-C_{20})$alkyl optionally substituted with one or two phenyl groups with the proviso that R contains twenty carbons or less, $(C_5-C_{19})$alkyl optionally substituted with one or two phenyl groups with the proviso that R contains twenty carbons or less, $(C_5-C_{18})$alkyl optionally substituted with one or two phenyl groups with the proviso that R contains twenty carbons or less, $(C_5-C_{17})$alkyl optionally substituted with one or two phenyl groups with the proviso that R contains twenty carbons or less, $(C_5-C_{16})$alkyl optionally substituted with one or two phenyl groups with the proviso that R contains twenty carbons or less, $(C_5-C_{15})$alkyl optionally substituted with one or two phenyl groups with the proviso that R contains twenty carbons or less, $(C_5-C_{14})$alkyl optionally substituted with one or two phenyl groups with the proviso that R contains twenty carbons or less, $(C_5-C_{13})$alkyl optionally substituted with one or two phenyl groups with the proviso that R contains twenty carbons or less, $(C_5-C_{12})$alkyl optionally substituted with one or two phenyl groups with the proviso that R contains twenty carbons or less, $(C_5-C_{11})$alkyl optionally substituted with one or two phenyl groups with the proviso that R contains twenty carbons or less, $(C_5-C_{10})$alkyl optionally substituted with one or two phenyl groups with the proviso that R contains twenty carbons or less, $(C_5-C_9)$alkyl optionally substituted with one or two phenyl groups with the proviso that R contains twenty carbons or less, $(C_5-C_8)$alkyl optionally substituted with one or two phenyl groups, $(C_5-C_7)$alkyl optionally substituted with one or two phenyl groups, and $(C_5-C_6)$alkyl optionally substituted with one or two phenyl groups.

In various embodiments of the present invention, R is chosen from: $(C_6-C_{20})$alkyl optionally substituted with one or two phenyl groups with the proviso that R contains twenty carbons or less, $(C_6-C_{19})$alkyl optionally substituted with one or two phenyl groups with the proviso that R contains twenty carbons or less, $(C_6-C_{18})$alkyl optionally substituted with one or two phenyl groups with the proviso that R contains twenty carbons or less, $(C_6-C_{17})$alkyl optionally substituted with one or two phenyl groups with the proviso that R contains twenty carbons or less, $(C_6-C_{16})$alkyl optionally substituted with one or two phenyl groups with the proviso that R contains twenty carbons or less, $(C_6-C_{15})$alkyl optionally substituted with one or two phenyl groups with the proviso that R contains twenty carbons or less, $(C_6-C_{14})$alkyl optionally substituted with one or two phenyl groups with the proviso that R contains twenty carbons or less, $(C_6-C_{13})$alkyl optionally substituted with one or two phenyl groups with the proviso that R contains twenty carbons or less, $(C_6-C_{12})$alkyl optionally substituted with one or two phenyl groups with the proviso that R contains twenty carbons or less, $(C_6-C_{11})$alkyl optionally substituted with one or two phenyl groups with the proviso that R contains twenty carbons or less, $(C_6-C_{10})$alkyl optionally substituted with one or two phenyl groups with the proviso that R contains twenty carbons or less, $(C_6-C_9)$alkyl optionally substituted with one or two phenyl groups with the proviso that R contains twenty carbons or less, $(C_6-C_8)$alkyl optionally substituted with one or two phenyl groups, and $(C_6-C_7)$alkyl optionally substituted with one or two phenyl groups.

In various embodiments of the present invention, R is chosen from: $(C_7-C_{20})$alkyl optionally substituted with one or two phenyl groups with the proviso that R contains twenty carbons or less, $(C_7-C_{19})$alkyl optionally substituted with one or two phenyl groups with the proviso that R contains twenty carbons or less, $(C_7-C_{18})$alkyl optionally substituted with one or two phenyl groups with the proviso that R contains twenty carbons or less, $(C_7-C_{17})$alkyl optionally substituted with one or two phenyl groups with the proviso that R contains twenty carbons or less, $(C_7-C_{16})$alkyl optionally substituted with one or two phenyl groups with the proviso that R contains twenty carbons or less, $(C_7-C_{15})$alkyl optionally substituted with one or two phenyl groups with the proviso that R contains twenty carbons or less, $(C_7-C_{14})$alkyl optionally substituted with one or two phenyl groups with the proviso that R contains twenty carbons or less, $(C_7-C_{13})$alkyl optionally substituted with one or two phenyl groups with the proviso that R contains twenty carbons or less, $(C_7-C_{12})$alkyl optionally substituted with one or two phenyl groups with the proviso that R contains twenty carbons or less, $(C_7-C_{11})$alkyl optionally substituted with one or two phenyl groups with the proviso that R contains twenty carbons or less, $(C_7-C_{10})$alkyl optionally substituted with one or two phenyl groups with the proviso that R contains twenty carbons or less, $(C_7-C_9)$alkyl optionally substituted with one or two phenyl groups with the proviso that R contains twenty carbons or less, and $(C_7-C_8)$alkyl optionally substituted with one or two phenyl groups.

In various embodiments of the present invention, R is chosen from: $(C_8-C_{20})$alkyl optionally substituted with one or two phenyl groups with the proviso that R contains twenty carbons or less, $(C_8-C_{19})$alkyl optionally substituted with one or two phenyl groups with the proviso that R contains twenty carbons or less, $(C_8-C_{18})$alkyl optionally substituted with one or two phenyl groups with the proviso that R contains twenty carbons or less, $(C_8-C_{17})$alkyl optionally substituted with one or two phenyl groups with the proviso that R contains twenty carbons or less, $(C_8-C_{16})$alkyl optionally substituted with one or two phenyl groups with the proviso that R contains twenty carbons or less, $(C_8-C_{15})$alkyl optionally substituted with one or two phenyl groups with the proviso that R contains twenty carbons or less, $(C_8-C_{14})$alkyl optionally substituted with one or two phenyl groups with the proviso that R contains twenty carbons or less, $(C_8-C_{13})$alkyl optionally substituted with one or two phenyl groups with the proviso that R contains twenty carbons or less, $(C_8-C_{12})$alkyl optionally substituted with one or two phenyl groups with the proviso that R contains twenty carbons or less, $(C_8-C_{11})$alkyl optionally substituted with one or two phenyl groups with the proviso that R contains twenty carbons or less, $(C_8-C_{10})$alkyl optionally substituted with one or two phenyl groups with the proviso that R contains twenty carbons or less, and $(C_8-C_9)$alkyl optionally substituted with one or two phenyl groups with the proviso that R contains twenty carbons or less.

In various embodiments of the present invention, R is chosen from: $(C_9-C_{20})$alkyl optionally substituted with a phenyl group with the proviso that R contains twenty carbons or less, $(C_9-C_{19})$alkyl optionally substituted with a phenyl group with the proviso that R contains twenty carbons or less, $(C_9-C_{18})$alkyl optionally substituted with a phenyl group with the proviso that R contains twenty carbons or less, $(C_9-C_{17})$alkyl optionally substituted with a phenyl group with the proviso that R contains twenty carbons or less, $(C_9-C_{16})$alkyl optionally substituted with a phenyl group with the proviso that R contains twenty carbons or less, $(C_9-C_{15})$alkyl optionally substituted with a phenyl group with the proviso that R contains twenty carbons or less, $(C_9-C_{14})$alkyl optionally substituted with a phenyl group, $(C_9-C_{13})$alkyl optionally substituted with a phenyl group, $(C_9-C_{12})$alkyl optionally substituted with a phenyl group, $(C_9-C_{11})$alkyl optionally substituted with a phenyl group, and $(C_9-C_{10})$alkyl optionally substituted with a phenyl group.

In various embodiments of the present invention, R is chosen from: $(C_{10}-C_{20})$alkyl optionally substituted with a phenyl group with the proviso that R contains twenty carbons or less, $(C_{10}-C_{19})$alkyl optionally substituted with a phenyl group with the proviso that R contains twenty carbons or less, $(C_{10}-C_{18})$alkyl optionally substituted with a phenyl group with the proviso that R contains twenty carbons or less, $(C_{10}-C_{17})$alkyl optionally substituted with a phenyl group with the proviso that R contains twenty carbons or less, $(C_{10}-C_{16})$alkyl optionally substituted with a phenyl group with the proviso that R contains twenty carbons or less, $(C_{10}-C_{15})$alkyl optionally substituted with a phenyl group with the proviso that R contains twenty carbons or less, $(C_{10}-C_{14})$alkyl optionally substituted with a phenyl group, $(C_{10}-C_{13})$alkyl optionally substituted with a phenyl group, $(C_{10}-C_{12})$alkyl optionally substituted with a phenyl group, and $(C_{10}-C_{11})$alkyl optionally substituted with a phenyl group.

In various embodiments of the present invention, R is chosen from: $(C_{11}-C_{20})$alkyl optionally substituted with a phenyl group with the proviso that R contains twenty carbons or less, $(C_{11}-C_{19})$alkyl optionally substituted with a phenyl group with the proviso that R contains twenty carbons or less, $(C_{11}-C_{18})$alkyl optionally substituted with a phenyl group with the proviso that R contains twenty carbons or less, $(C_{11}-C_{17})$alkyl optionally substituted with a phenyl group with the proviso that R contains twenty carbons or less, $(C_{11}-C_{16})$alkyl optionally substituted with a phenyl group with the proviso that R contains twenty carbons or less, $(C_{11}-C_{15})$alkyl optionally substituted with a phenyl group with the proviso that R contains twenty carbons or less, $(C_{11}-C_{14})$alkyl optionally substituted with a phenyl group, $(C_{11}-C_{13})$alkyl optionally substituted with a phenyl group, and $(C_{11}-C_{12})$alkyl optionally substituted with a phenyl group.

In various embodiments of the present invention, R is chosen from: $(C_{12}-C_{20})$alkyl optionally substituted with a phenyl group with the proviso that R contains twenty carbons or less, $(C_{12}-C_{19})$alkyl optionally substituted with a phenyl group with the proviso that R contains twenty carbons or less, $(C_{12}-C_{18})$alkyl optionally substituted with a phenyl group with the proviso that R contains twenty carbons or less, $(C_{12}-C_{17})$alkyl optionally substituted with a phenyl group with the proviso that R contains twenty carbons or less, $(C_{12}-C_{16})$alkyl optionally substituted with a phenyl group with the proviso that R contains twenty carbons or less, $(C_{12}-C_{15})$alkyl optionally substituted with a phenyl group with the proviso that R contains twenty carbons or less, $(C_{12}-C_{14})$alkyl optionally substituted with a phenyl group, and $(C_{12}-C_{13})$alkyl optionally substituted with a phenyl group.

In various embodiments of the present invention, R is chosen from: $(C_{13}-C_{20})$alkyl optionally substituted with a phenyl group with the proviso that R contains twenty carbons or less, $(C_{13}-C_{19})$alkyl optionally substituted with a phenyl group with the proviso that R contains twenty carbons or less, $(C_{13}-C_{18})$alkyl optionally substituted with a phenyl group with the proviso that R contains twenty carbons or less, $(C_{13}-C_{17})$alkyl optionally substituted with a phenyl group with the proviso that R contains twenty carbons or less, $(C_{13}-C_{16})$alkyl optionally substituted with a phenyl group with the proviso that R contains twenty carbons or less, $(C_{13}-C_{15})$alkyl optionally substituted with a phenyl group with the proviso that R contains twenty carbons or less, and $(C_{13}-C_{14})$alkyl optionally substituted with a phenyl group.

In various embodiments of the present invention, R is chosen from: $(C_{14}-C_{20})$alkyl optionally substituted with a phenyl group with the proviso that R contains twenty carbons or less, $(C_{14}-C_{19})$alkyl optionally substituted with a phenyl group with the proviso that R contains twenty carbons or less, $(C_{14}-C_{18})$alkyl optionally substituted with a phenyl group with the proviso that R contains twenty carbons or less, $(C_{14}-C_{17})$alkyl optionally substituted with a phenyl group with the proviso that R contains twenty carbons or less, $(C_{14}-C_{16})$alkyl optionally substituted with a phenyl group with the proviso that R contains twenty carbons or less, and $(C_{14}-C_{15})$alkyl optionally substituted with a phenyl group with the proviso that R contains twenty carbons or less.

In various embodiments of the present invention, R is chosen from: $(C_{15}-C_{20})$alkyl, $(C_{15}-C_{19})$alkyl, $(C_{15}-C_{18})$alkyl, $(C_{15}-C_{17})$alkyl, and $(C_{15}-C_{16})$alkyl.

In various embodiments of the present invention, R is chosen from: $(C_{16}-C_{20})$alkyl, $(C_{16}-C_{19})$alkyl, $(C_{16}-C_{18})$alkyl, and $(C_{16}-C_{17})$alkyl.

In various embodiments of the present invention, R is chosen from: $(C_{17}-C_{20})$alkyl, $(C_{17}-C_{19})$alkyl, and $(C_{17}-C_{18})$alkyl.

In various embodiments of the present invention, R is $(C_{18}-C_{20})$alkyl or $(C_{18}-C_{19})$alkyl.

In various embodiments of the present invention, R is $(C_{19}-C_{20})$alkyl.

In various embodiments of the present invention, R is chosen from: $(C_{20})$alkyl, $(C_{19})$alkyl, $(C_{18})$alkyl, $(C_{17})$alkyl, $(C_{16})$alkyl, $(C_{15})$alkyl, $(C_{14})$alkyl optionally substituted with a phenyl group, $(C_{13})$alkyl optionally substituted with a phenyl group, $(C_{12})$alkyl optionally substituted with a phenyl group, $(C_{11})$alkyl optionally substituted with a phenyl group, (C₁₀)alkyl optionally substituted with a phenyl group, (C₉)alkyl optionally substituted with a phenyl group, (C₈)alkyl optionally substituted with one or two phenyl groups, (C₇)alkyl optionally substituted with one or two phenyl groups, (C₆)alkyl optionally substituted with one or two phenyl groups, (C₅)alkyl optionally substituted with one or two phenyl groups, (C₄)alkyl optionally substituted with one or two phenyl groups, (C₃)alkyl optionally substituted with one or two phenyl groups, ethyl optionally substituted with one or two phenyl groups, and methyl optionally substituted with one or two phenyl groups.

In various embodiments of the present invention, R is $C_nH_m$. In some of these embodiments, n is 1 and m is 3, (i.e., methyl). In some of these embodiments, n is 2 and m is 5, (i.e., ethyl). In some of these embodiments, n is 3 and m is chosen from: 3, 5, and 7. In some of these embodiments, n is 4 and m is chosen from: 5, 7, and 9. In some of these embodiments, n is 5 and m is chosen from: 7, 9, and 11. In some of these embodiments, n is 6 and m is chosen from: 5, 7, 9, 11, and 13. In some of these embodiments, n is 7 and m is chosen from: 7, 9, 11, 13, and 15. In some of these embodiments, n is 8 and m is chosen from: 5, 7, 9, 11, 13, 15, and 17. In some of these embodiments, n is 9 and m is chosen from: 7, 9, 11, 13, 15, 17, and 19. In some of these embodiments, n is 10 and m is chosen from: 7, 9, 11, 13, 15, 17, 19, and 21. In some of these embodiments, n is 11 and m is chosen from: 9, 11, 13, 15, 17, 19, 21, and 23. In some of these embodiments, n is 12 and m is chosen from: 7, 9, 11, 13, 15, 17, 19, 21, 23, and 25. In some of these embodiments, n is 13 and m is chosen from: 9, 11, 13, 15, 17, 19, 21, 23, 25, and 27. In some of these embodiments, n is 14 and m is chosen from: 9, 11, 13, 15, 17, 19, 21, 23, 25, 27, and 29. In some of these embodiments, n is 15 and m is chosen from: 11, 13, 15, 17, 19, 21, 23, 25, 27, 29, and 31. In some of these embodiments, n is 16 and m is chosen from: 9, 11, 13, 15, 17, 19, 21, 23, 25, 27, 29, 31, and 33. In some of these embodiments, n is 17 and m is chosen from: 11, 15, 17, 19, 21, 23, 25, 27, 29, 31, 33, and 35. In some of these embodiments, n is 18 and m is chosen from: 11, 13, 15, 17, 19, 21, 23, 25, 27, 29, 31, 33, 35, and 37. In some of these embodiments, n is 19 and m is chosen from: 13, 15, 17, 19, 21, 23, 25, 27, 29, 31, 33, 35, 37, and 39. In some of these embodiments, n is 20 and m is chosen from: 11, 13, 15, 17, 19, 21, 23, 25, 27, 29, 31, 33, 35, 37, 39, and 41.

In some embodiments, R is chosen from: n-propyl, isopropyl, cyclopropyl, n-butyl, 1-methylpropyl, 2-ethylbutyl, 1-methyl-2-ethylbutyl, 2-methylpropyl, tert-butyl, 2-methylcyclopropyl, 1-methylcyclopropyl, cyclobutyl, cyclopropylmethyl (i.e.,

), n-pentyl, 1-methylbutyl, 2-methylbutyl, 3-methylbutyl, 1-ethylpropyl, 1,2-dimethylpropyl, 1,1-dimethylpropyl, 2,2-dimethylpropyl, cyclobutylmethyl (i.e.,

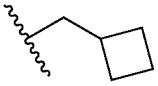 [SMILES: *CC1CCC1]

), 2-(cyclopropyl)ethyl (i.e.,

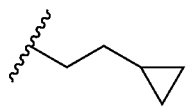 [SMILES: *CCC1CC1]

), cyclopentyl, n-hexyl, 1-methylpentyl, 2-methylpentyl, 3-methylpentyl, 4-methylpentyl, 1,1-dimethylbutyl, 1,2-dimethylbutyl, 1,3-dimethylbutyl, 2,3-dimethylbutyl, 2,2-dimethylbutyl, 3,3-dimethylbutyl, 1,1,2-trimethylpropyl, 1,2,2-trimethylpropyl, 3-(cyclopropyl)propyl (i.e.,

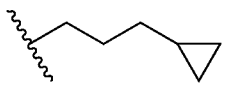 [SMILES: *CCCC1CC1]

), 2-(cyclobutyl)ethyl (i.e.,

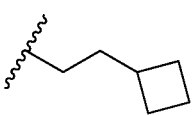 [SMILES: *CCC1CCC1]

), cyclopentylmethyl (i.e.,

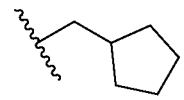

), cyclohexyl, cyclohexylmethyl, 2-cyclohexylethyl, dicyclohexylmethyl, n-octyl, benzyl, diphenylmethyl, decyl, dodecyl, tetradecyl, hexadecyl, hexadec-9-enyl, octadecyl, octadec-9-enyl, octadec-9,12-dienyl, 2-propylpentyl, 2-butylhexyl, 2-pentylheptyl, 2-hexyloctyl.

As used herein, and as would be understood by the person of skill in the art, the recitation of "a compound"—unless expressly further limited—is intended to include salts of that compound.

The term "pharmaceutically acceptable salt" refers to salts whose counter ion derives from pharmaceutically acceptable non-toxic acids and bases. Suitable pharmaceutically acceptable acids for salts of the amino-substituted compounds of the present invention include, for example, acetic, adipic, alginic, ascorbic, aspartic, benzenesulfonic (besylate), benzoic, boric, butyric, camphoric, camphorsulfonic, carbonic, citric, ethanedisulfonic, ethanesulfonic, ethylenediaminetetraacetic, formic, fumaric, glucoheptonic, gluconic, glutamic, hydrobromic, hydrochloric, hydroiodic, hydroxynaphthoic, isethionic, lactic, lactobionic, laurylsulfonic, maleic, malic, mandelic, methanesulfonic, mucic, naphthylenesulfonic, nitric, oleic, pamoic, pantothenic, phosphoric, pivalic, polygalacturonic, salicylic, stearic, succinic, sulfuric, tannic, tartaric acid, teoclatic, p-toluenesulfonic, and the like. Suitable pharmaceutically acceptable base addition salts for the carboxylate-substituted compounds of the present invention include, but are not limited to, metallic salts made from aluminum, calcium, lithium, magnesium, potassium, sodium and zinc or organic salts made from lysine, arginine, N,N-dibenzylethylenediamine, chloroprocaine, choline, diethanolamine, ethylenediamine, meglumine (N-methylglucamine), and procaine. Further pharmaceutically acceptable salts include, when appropriate, nontoxic ammonium cations and carboxylate, sulfonate and phosphonate anions attached to alkyl having from 1 to 20 carbon atoms.

It will be recognized that the compounds of this invention can exist in radiolabeled form, i.e., the compounds may contain one or more atoms containing an atomic mass or mass number different from the atomic mass or mass number usually found in nature. Alternatively, a plurality of molecules of a single structure may include at least one atom that occurs in an isotopic ratio that is different from the isotopic ratio found in nature. Radioisotopes of hydrogen, carbon, phosphorous, fluorine, chlorine and iodine include $^{2}H$, $^{3}H$, $^{11}C$, $^{13}C$, $^{14}C$, $^{15}N$, $^{35}S$, $^{18}F$, $^{36}Cl$, $^{125}I$, $^{124}I$ and $^{131}I$ respectively. Compounds that contain those radioisotopes and/or other radioisotopes of other atoms are within the scope of this invention. Persons skilled in the art recognize that deuterium has been used to improve metabolic stability of compounds, and that principle can be applied to these compounds. Tritiated, i.e. $^{3}H$, and carbon-14, i.e., $^{14}C$, radioisotopes are particularly preferred for their ease in preparation and detectability. Compounds that contain isotopes $^{11}C$, $^{13}N$, $^{15}O$, $^{124}I$, and $^{18}F$ are well suited for positron emission tomography. Radiolabeled compounds of formulae I and II of this invention and prodrugs thereof can generally be prepared by methods well known to those skilled in the art. Conveniently, such radiolabeled compounds can be prepared by carrying out the procedures disclosed in the Examples and Schemes by substituting a readily available radiolabeled reagent for a non-radiolabeled reagent.

Although this invention is susceptible to embodiment in many different forms, preferred embodiments of the invention are shown. It should be understood, however, that the present disclosure is to be considered as an exemplification of the principles of this invention and is not intended to limit the invention to the embodiments illustrated. It may be found upon examination that certain members of the claimed genus are not patentable to the inventors in this application. In this event, subsequent exclusions of species from the compass of applicants' claims are to be considered artifacts of patent prosecution and not reflective of the inventors' concept or description of their invention; the invention encompasses all of the members of the genus I that are not already in the possession of the public.

The terms "subject" or "subject in need thereof" are used interchangeably herein. These terms refer to a patient who has been diagnosed with the underlying disorder to be treated. The subject may currently be experiencing symptoms associated with the disorder or may have experienced symptoms in the past. Additionally, a "subject in need thereof" may be a patient at risk of developing a particular disease, or to a patient reporting one or more of the physiological systems of a disease, even though a diagnosis of this disease may not have been made. As a non-limiting example, a "subject in need thereof", for purposes of this application, may include a subject who is currently diagnosed with epilepsy or was diagnosed with epilepsy in the past, or who is at risk of seizures, regardless of current symptomatology.

As used herein, the terms "treatment" or "treating" are used interchangeably. These terms refer to an approach for obtaining beneficial or desired results including, but not limited to, therapeutic benefit. Therapeutic benefit includes eradication or amelioration of the underlying disorder being treated; it also includes the eradication or amelioration of one or more of the symptoms associated with the underlying disorder such that an improvement is observed in the patient, notwithstanding that the patient may still be afflicted with the underlying disorder.

The compounds described herein are useful for treating epilepsy, and pain. In the case of "treating epilepsy", the term encompasses amelioration of the symptom of seizures and convulsions. In the case of "treating pain", the term encompasses amelioration of neuropathic pain, chemotherapy induced pain, backache, bone pain, abdominal pain, postoperative pain, traumatic injury pain, menstrual pain, muscle pain, joint pain, headache, migraine, dental pain, evoked pain, and pain due to inflammation.

Chemical Synthesis of Compounds

In general, the compounds of the present invention may be prepared by the methods illustrated in the general reaction schemes as, for example, described below, or by modifications thereof, using readily available starting materials, reagents and conventional synthesis procedures. In these reactions, it is also possible to make use of variants that are in themselves known but are not mentioned here. The starting materials are either commercially available, synthesized as described in the examples or may be obtained by the methods well known to persons of skill in the art. Standard synthetic methods and procedures for the preparation of organic molecules and functional group transformations and manipulations can be readily obtained from the relevant scientific literature or from standard textbooks in the field. It will be appreciated that where typical or preferred process conditions (i.e., reaction temperatures, times, mole ratios of reactants, solvents, pressures, etc.) are given; other process conditions can also be used unless otherwise stated. Optimum reaction conditions can vary with the particular reactants or solvent used. Those skilled in the art will recognize that the nature and order of the synthetic steps presented can be varied for the purpose of optimizing the formation of the compounds described comprehensive list of abbreviations utilized by organic chemists appears in the first issue of each volume of the Journal of Organic Chemistry. The list, which is typically presented in a table entitled "Standard List of Abbreviations", provides definitions for abbreviations not found in the following list of abbreviations:

° C. degrees Celsius
ACN acetonitrile
Cl chloride
$Cs_2CO_3$ cesium carbonate
DCC N,N'-dicyclohexylcarbodiimide
DCM dichloromethane or methylene chloride
DIPEA diisopropylethylamine
DMAP 4-dimethylaminopyridine or N,N-dimethylaminopyridine
DMF N,N-dimethylformamide
EDC N-(3-dimethylaminopropyl)-N'-ethylcarbodiimide hydrochloride
eq. equivalent(s)
EtOAc ethyl acetate
EtOH ethanol
ESI electrospray ionization
g gram(s)
HATU 1-[bis(dimethylamino)methylene]-1H-1,2,3-triazolo[4,5-b]pyridinium 3-oxid hexafluorophosphate
HBTU 2-(1H-benzotriazole-1-yl)-1,1,3,3-tetramethyluronium hexafluorophosphate
HCl hydrochloric acid
HPLC high performance liquid chromatography
h hour(s)

I iodide
LC/MS liquid chromatography mass spectrometry
LDA lithium diisopropylamide
LiHMDS lithium bis(trimethylsilyl)amide
K$_2$CO$_3$ potassium carbonate
KHMDS potassium bis(trimethylsilyl)amide
KMnO$_4$ potassium permanganate
M molarity concentration
μm micron
MeOH methanol
mg milligram(s)
min minute(s)
mL milliliter(s)
mmol millimole(s)
N normal concentration
Na$_2$CO$_3$ sodium carbonate
NaH sodium hydride
NaHCO$_3$ sodium hydrogen carbonate
NaHMDS sodium bis(trimethylsilyl)amide
NaOH sodium hydroxide
NMR nuclear magnetic resonance
OMs mesylate
OTf triflate
OTs tosylate
Pd/C palladium on carbon
Ph phenyl
psi pounds per square inch
PyBOP (benzotriazol-1-yloxy)tripyrrolidinophosphonium hexafluorophosphate
Ru/C ruthenium on carbon
TBTU 2-(1H-benzotriazole-1-yl)-1,1,3,3-tetramethylaminium tetrafluoroborate
TEA triethylamine
TFA trifluoroacetic acid
THF tetrahydrofuran
TMS-I iodotrimethylsilane
TLC thin layer chromatography Terminology related to "protecting", "deprotecting" and "protected" functionalities occurs throughout this application. Such terminology is well understood by persons of skill in the art and is used in the context of processes that involve sequential treatment with a series of reagents. In that context, a protecting group refers to a group, which is used to mask a functionality during a process step in which it would otherwise react, but in which reaction is undesirable. The protecting group prevents reaction at that step but may be subsequently removed to expose the original functionality. The removal or "deprotection" occurs after the completion of the reaction or reactions in which the functionality would interfere. Thus, when a sequence of reagents is specified, as it is in the processes described herein, the person of ordinary skill can readily envision those groups that would be suitable as "protecting groups". Suitable groups for that purpose are discussed in standard textbooks in the field of chemistry, such as *Protective Groups in Organic Synthesis* by T. W. Greene and P. G. M. Wuts [John Wiley & Sons, New York, 1999].

LIST OF PROTECTING GROUPS AND THEIR ABBREVIATIONS

Acetyl (Ac)
Acylals
Carboallyloxy (Alloc)
Benzoyl (Bz)
Benzyl (Bn, Bnl)
Benzyl esters
Carbamate
Carbobenzyloxy (Cbz)
Dimethoxytrityl, [bis-(4-methoxyphenyl)phenylmethyl] (DMT)
Dithianes
Ethoxyethyl ethers (EE)
Fluorenylmethyloxycarbonyl (Fmoc)
Methoxymethyl ether (MOM)
Methoxytrityl [(4-methoxyphenyl)diphenylmethyl], MMT)
Methyl Ethers
Methyl (Me)
Methyl esters
Methylthiomethyl ether
Orthoesters
Oxazoline
Pivaloyl (Piv)
Phthalimido
p-Methoxybenzyl carbonyl (Moz or MeOZ)
p-Methoxybenzyl (PMB)
p-Methoxyphenyl (PMP)
Propargyl alcohols
Silyl groups (e.g., trimethylsilyl (TMS), tert-butyldimethylsilyl (TBDMS), tri-iso-propylsilyloxymethyl (TOM) and triisopropylsilyl (TIPS))
Silyl esters
tert-Butyl esters
tert-Butyloxycarbonyl (Boc or tBoc)
Tetrahydropyranyl (THP)
Tosyl (Ts or Tos)
Trichloroethyl chloroformate (Troc)
Trimethylsilylethoxymethyl (SEM)
Trityl (triphenylmethyl, Tr)
β-Methoxyethoxymethyl ether (MEM)
(4-Nitrophenyl)sulfonyl or (4-nitrophenyl)(dioxido)-lambda (6)-sulfanyl) (Nosyl)
2-Cyanoethyl
2-Nitrophenylsulfenyl (Nps)
3,4-Dimethoxybenzyl (DMPM)
2,2,4,6,7-Pentamethyldihydrobenzofuran-5-sulfonyl (Pbf)

I. Generic Chemical Synthesis Section

Compounds of the present invention are prepared using methods illustrated in the general synthetic schemes and experimental procedures detailed below. These general synthetic schemes and experimental procedures are presented for purposes of illustration and are not intended to be limiting. Starting materials used to prepare compounds of the present invention are commercially available or can be prepared using routine methods known in the art. Where present, names of compounds were generated using ChemAxon's Instant JChem v6.1 for Desktop and IUPAC Naming Plugin.

Intermediate compounds I, V, and VIII are made using protocols previously described in the literature (B. Huff "Excitatory amino acid receptor antagonists." U.S. Pat. No. 5,284,957, 1994; A. M. Brian Arnold, et al. "Process for preparing isoquinoline compounds." U.S. Pat. No. 5,648,492, 1997; Paul L. Ornstein, et al. "(3SR,4aRS,6RS,8aRS)-6-[2-(1H-tetrazol-5-yl)ethyl]decahydroisoquinoline-3-carboxylic Acid: A Structurally Novel, Systemically Active, Competitive AMPA Receptor Antagonist." *J. Med. Chem.*, 1993, 36, 2046-2048; Paul L. Ornstein, et al. "Syntheses of Oxodecahydroisoquinoline-3-carboxylates. Useful Intermediates for the Preparation of Conformationally Defined Excitatory Amino Acid Antagonists." *J. Org. Chem.*, 1991, 56, 4388-4392).

Scheme 1 illustrates a general synthetic scheme to make the desired compounds IV from ketone I. In step 1, methyl carbamate-protected carboxylic acid I is treated with iodotrimethylsilane at room temperature, or alternatively, with 6 N hydrochloric acid at 90° C., to remove the methyl carbamate-protecting group and afford ketone amino acid II. Compound II is reacted, under basic conditions (e.g. 2 N aqueous NaOH, triethylamine, diisopropylethylamine, etc.), with benzyl chloroformate (Cbz), di-tert-butyl dicarbonate (Boc), or similar reagent to afford carbamate-protected carboxylic acids III. Compounds III are esterified to make ketone carbamate esters IV. Several methods are possible: 1) compounds III are esterified with alcohols (HO—R1) using a coupling reagent (e.g. N,N'-dicyclohexylcarbodiimide (DCC), EDC, HBTU, HATU, PyBOP, etc.) under basic conditions (e.g. triethylamine, diisopropylethylamine, pyridine, N,N-4-dimethylaminopyridine, etc.), 2) compounds III are alkylated with an activated alkane (X—R1, where X=OTf, OTs, OMs, I, Br, and $C_1$) under basic conditions (e.g. NaOH, NaH, $NaCO_3$, $K_2CO_3$, $Cs_2CO_3$, $NaHCO_3$, etc.), and 3) compounds III are esterified with alcohols (HO—R1) using Mitsunobu conditions (e.g. diethyl azodicarboxylate and triphenylphosphine, or similar reagents).

N aqueous NaOH, triethylamine, diisopropylethylamine, etc.), with benzyl chloroformate (Cbz), di-tert-butyl dicarbonate (Boc), or similar protecting group that is stable to basic conditions but that can be removed more easily than methyl carbamate to afford carbamate-protected ethyl ester VII. Compounds VII are then hydrolyzed under standard aqueous basic conditions (e.g. 2 N aqueous NaOH in alcoholic solvent or similar aqueous miscible organic solvent) to afford carbamate-protected acids III. Compounds III are then esterified as described in Scheme 1 to make ketone carbamate esters IV.

Scheme 2. General Synthesis of Ketone Carbamate Acids III from Ketone Ester V

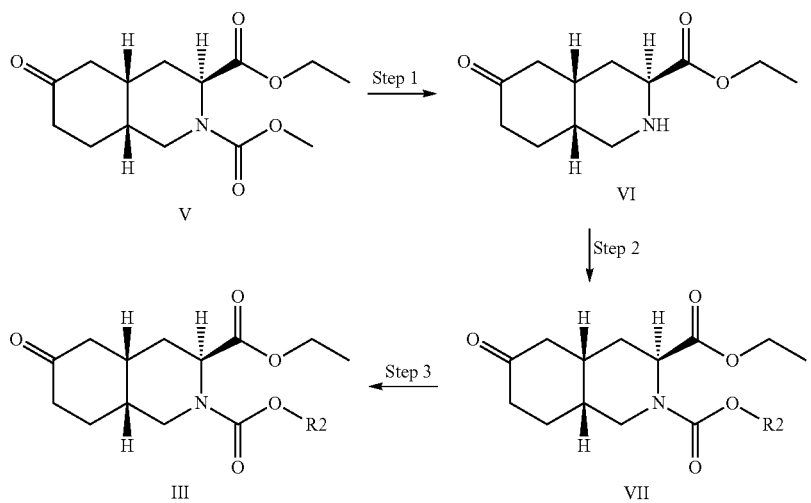

Scheme 2 illustrates a general synthetic scheme to make the desired compounds III from ketone ester V. In step 1, methyl carbamate-protected ethyl ester V is treated with iodotrimethylsilane at room temperature to remove the methyl carbamate-protecting group and afford amino ester VI. Ethyl ester VI is reacted, under basic conditions (e.g. 2

Scheme 3 illustrates a general synthetic scheme to make the desired compounds IX from protected ketone carbamate esters IV. The tetrazole Wittig reagent VIII (made as previously described in B. Huff U.S. Pat. No. 5,284,957) is deprotonated under strong basic conditions (e.g. LiHMDS, NaHMDS, LDA, etc.) and reacted with ketones IV to make olefin compounds IX.

Scheme 1. General Synthesis of Ketone Carbamate Esters IV from Ketone I

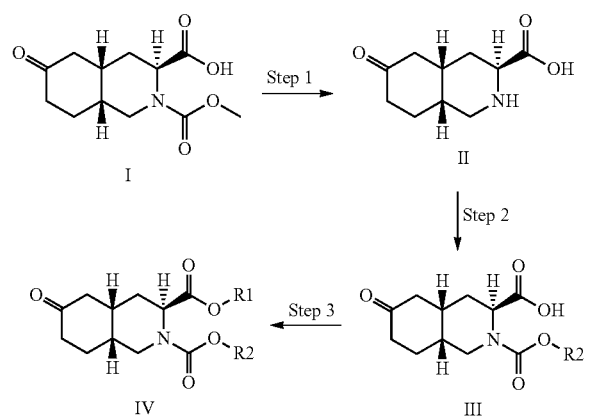

Scheme 3. General Synthesis of Olefin Compounds IX from Ketone Carbamate Esters IV

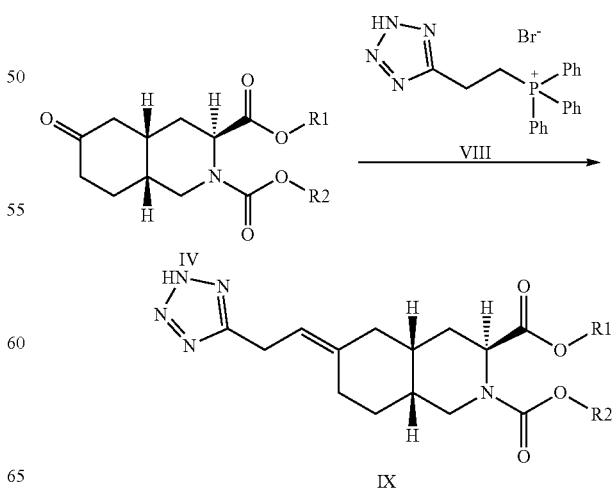

Scheme 4 illustrates a general synthetic scheme to make the desired compounds X from protected olefins IX. Free radical hydrofluorination of IX provides a mixture of fluorinated carbamate esters X (*J. Am. Chem. Soc.,* 2012, 134, 33, 13588-13591 "Fe(III)/NaBH4-Mediated Free Radical Hydrofluorination of Unactivated Alkenes." Timothy J. Barker and Dale L. Boger). Isomers may be separated by crystallization or chromatography to afford isomerically pure fluorinated carbamate esters X. In addition, alternative hydrofluorination conditions can be used, including but not limited to protocols using $KHSO_4$-13HF complex (*J. Am. Chem. Soc.,* 2017, 139, 18202-18205 "Widely Applicable Hydrofluorination of Alkenes via Bifunctional Activation of Hydrogen Fluoride." Zhichao Lu, Xiaojun Zeng, Gerald B. Hammond, and Bo Xu), fluorine cobalt complexes (*Org. Lett.,* 2013, 15, 20, 5158 "Cobalt-Catalyzed Hydrofluorination of Unactivated Olefins: A Radical Approach of Fluorine Transfer." Hiroki Shigehisa, Eriko Nishi, Mayu Fujisawa, and Kou Hiroya), Superacid HF/SbF5 (*Chem. Commun.,* 2007, 31, 98. "A novel, facile route to beta-fluoroamines by hydrofluorination using superacid HF/SbF5." Sebastien Thibaudeau, Agnes Martin-Mingot, Marie-Paule Jouannetaud, Omar Karamb, and Fabien Zuninob) and HF Pyridine (*Org. Synth.,* 1978, 58, 75 "Fluorinations With Pyridinium Polyhydrogen Fluoride." George A. Olah and Michael Watkins.

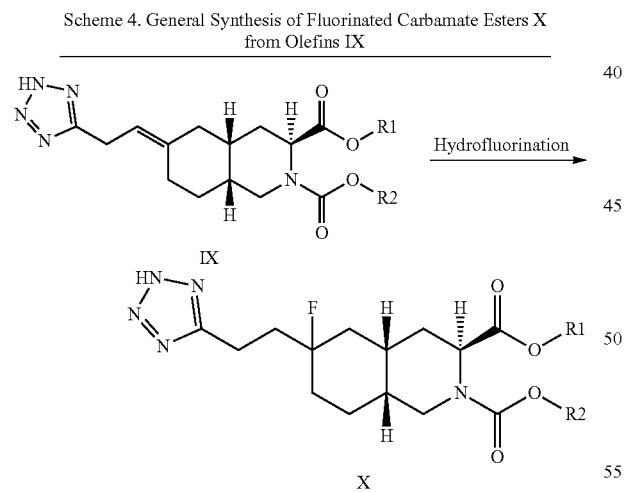

Scheme 5 illustrates a general synthetic scheme to make fluorinated ester amine prodrugs IX from fluorinated carbamate esters X. The carbamate-protecting group is removed using established published protocols (e.g. hydrogenation using hydrogen gas and a Pd/C catalyst for Cbz, TFA conditions or 4 N HCl for Boc, etc.). Isomers are separated by crystallization or chromatography to afford isomerically pure fluorinated ester amines XI.

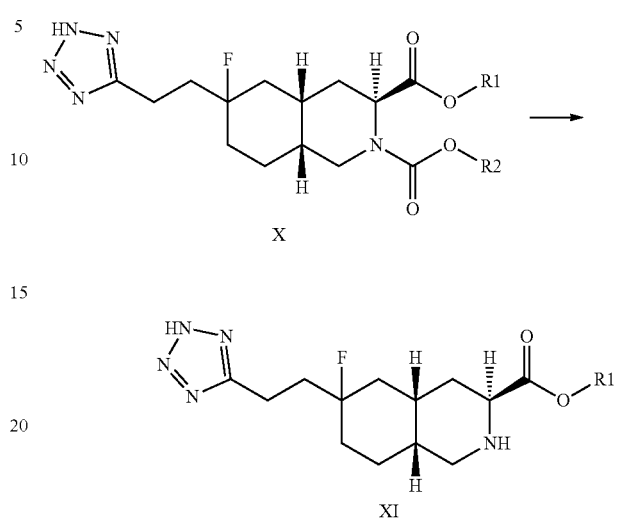

Scheme 6 illustrates a general synthetic scheme to make the desired fluorinated amino acid compound 1 from fluorinated amino esters XI. The esters are hydrolyzed under standard aqueous basic conditions (e.g. 2 N aqueous NaOH or 2 N aqueous NaOH in alcoholic solvent or similar aqueous miscible organic solvent) to afford fluorinated amino acid XII.

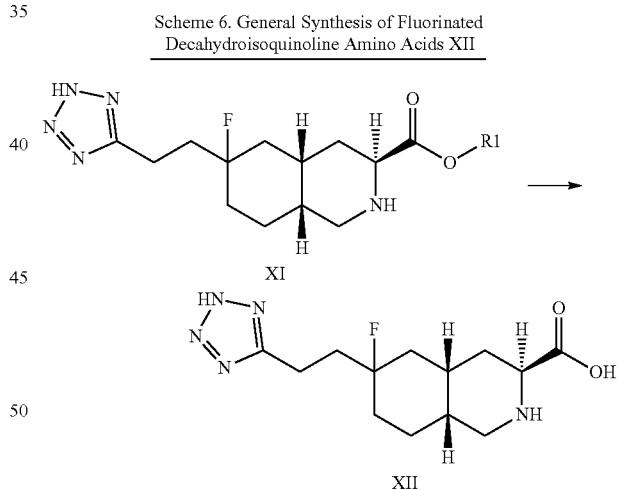

Final purification and isolation affords fluorinated decahydroisoquinoline amino acid 1 and 2.

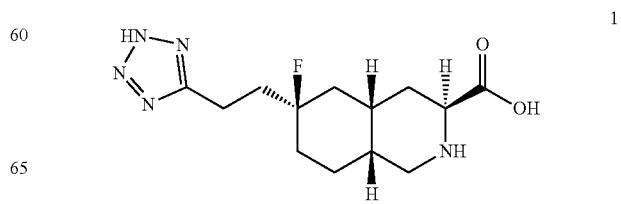

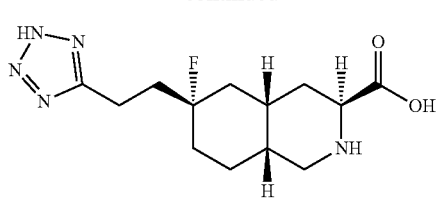

II. Experimental Chemical Synthesis Section

All chemical reagents were purchased commercially and were used without further purification. Reactions were done under air/nitrogen atmosphere according to the requirements. Column chromatography was performed on silica gel 60 (230-400 mesh) and analytical TLC was performed on plates coated with silica gel. TLC plates were stained with ceric ammonium molybdate (CAM), p-anisaldehyde (Anis), potassium permanganate ($KMnO_4$), or ninhydrin staining solutions. Routine $^1H$ NMR spectra were recorded using a Bruker 300 MHz or Varian 300 MHz instrument using deuterium oxide, chloroform-d, or methanol-$d_4$ as solvents. HPLC spectra were recorded using Agilent Series 1100 HPLC using a Zorbax SB-C18 (4.6×150 mm) column with gradient elution from 5% B to 95% B (Mobile Phase A: 0.05% $HClO_4$ in water; Mobile Phase B: acetonitrile) over 8.5 min and UV-detection at 205 nm or a Waters Sunfire C18 (4.6×75 mm, 3.5 μm, Part No. 186002552) column with gradient elution from 5% B to 95% B (Mobile Phase A: 0.1% TFA in water; Mobile Phase B: 0.1% TFA in acetonitrile) over 8.6 min and UV-detection at all wave length. Mass spectrometry was done using an Advion Expression CMS (ESI) or Agilent (Hewlett Packard Series 1100 MSD) with MassLynx interface (ESI: positive or negative ion mode) or a Waters 29996, Micromass ZQ (ESI: positive or negative ion mode). Preparative reverse phase chromatography was conducted using a Gilson System with a Waters Sunfire C18 OBD preparative column (30×150 mm column, 10 μm, Part No. 186002670). In some cases, normal phase silica gel column chromatography was performed using a CombiFlash Teledyne ISCO system.

Preparation of ethyl (3S,4aS,8aR)-6-oxo-decahydroisoquinoline-3-carboxylate (I-01)

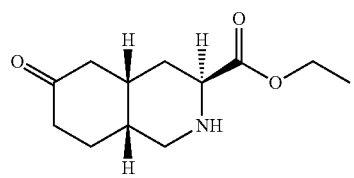

To a solution of 3-ethyl 2-methyl (3S,4aS,8aR)-6-oxo-decahydroisoquinoline-2,3-dicarboxylate (35.42 g, 125 mmol) in methylene chloride (600 mL) under nitrogen, was added iodotrimethylsilane (100 g, 500 mmol) in one portion at room temperature. The reaction mixture was stirred overnight and quenched with ethanol (250 mL). The solution was concentrated under vacuum and dried for 3 h under reduced pressure to afford the desired crude amino ester I-01 as a golden yellow solid (43 g crude) which was used directly without purification in the next step. $^1H$ NMR (300.13 MHz, $CD_3OD$) δ 4.31 (q, J=5.3 Hz, 2H), 4.17 (d, J=9.6 Hz, 1H), 3.31-3.21 (m, 1H), 3.14 (dd, J=9.6, 3.2 Hz, 1H), 2.21 (d, J=9.5 Hz, 1H), 2.13-2.08 (m, 2H), 2.00 (dt, J=10.1, 3.1 Hz, 1H), 1.88-1.69 (m, 4H), 1.58 (d, J=9.9 Hz, 1H), 1.40-1.35 (m, 1H), 1.32 (t, J=5.3 Hz, 3H) ppm.

Scale-Up Batch: To a solution of 3-ethyl 2-methyl (3S, 4aS,8aR)-6-oxo-decahydroisoquinoline-2,3-dicarboxylate (74.4 g, 262.6 mmol) in methylene chloride (1200 mL) under nitrogen, was added iodotrimethylsilane (200 g, 1.0 mol) in one portion at room temperature. The reaction mixture was stirred overnight and quenched with ethanol (280 mL). The solution was concentrated under vacuum and dried for 3 h under reduced pressure to afford the desired crude amino ester I-01 as a golden yellow solid (90.5 g crude) which was used directly without further purification.

Synthesis of Ketone Carbamate Esters IV

Preparation of 2-benzyl 3-ethyl (3S,4aS,8aR)-6-oxo-decahydroisoquinoline-2,3-dicarboxylate (I-02)

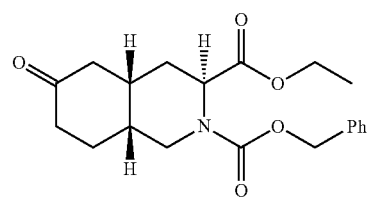

To a slurry of I-01 (crude, 6.25 mmol) in methylene chloride (50 mL) was added triethylamine (3.5 mL, 25.1 mmol) at 5-10° C. and the mixture was stirred for 10 min under nitrogen atmosphere. Benzyl chloroformate (1.12 mL, 7.62 mmol) was added slowly at 5-10° C. The mixture was warmed to room temperature and stirred for 2-3 h (the reaction was monitored by TLC and $KMnO_4$ staining). The mixture was adjusted to pH 3-4 using 3 N HCl and diluted with ethyl acetate (50 mL). The layers were separated and the combined organic layers were washed with brine (15 mL), dried over sodium sulfate, and concentrated under vacuum. The resulting residue was purified by flash column chromatography (silica gel, 0% to 40% ethyl acetate/hexane) to afford I-02 as a light yellow oil (2.12 g, 94% yield). $^1H$ NMR (300.13 MHz, $CDCl_3$) δ 7.36-7.27 (m, 5H), 5.14 (d, J=24.6, 14.1 Hz, 2H), 4.92 (dd, J=41.3, 8.3 Hz, 1H), 4.22-4.14 (m, 2H), 4.02 (dd, J=22.5, 13.5 Hz, 1H), 3.27 (ddd, J=34.5, 13.5, 3.0 Hz, 1H), 2.59 (dd, J=16.5, 6.0 Hz, 1H), 2.38-1.65 (m, 9H), 1.26 (t, J=7.2 Hz, 1.5H), 1.21 (t, J=7.2 Hz, 1.5H) ppm.

Preparation of 2-tert-butyl 3-ethyl (3S,4aS,8aR)-6-oxo-decahydroisoquinoline-2,3-dicarboxylate (I-03)

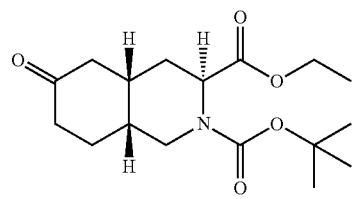

Crude I-01 (125 mmol) from a previous reaction was dissolved in methylene chloride (600 mL) and triethylamine (60.7 mL, 435 mmol) was added. After stirring for 15 minutes, a solution of di-tert-butyl-dicarbonate (32.7 g, 150 mmol) in methylene chloride (100 mL) was added. The resulting mixture was stirred overnight at room temperature and then concentrated under vacuum. The resulting solid was suspended in ethyl acetate (300 mL) and filtered. The filtrate was washed with 1 N HCl (60 mL) and brine (100 mL). The organic phase was dried over sodium sulfate, filtered, and concentrated under vacuum. The resulting residue was purified by flash column chromatography (silica gel, 0% to 25% ethyl acetate/hexane) to afford I-03 as a colorless oil (30.0 g, 74% yield). $^1$H NMR (300.13 MHz, CDCl$_3$) δ 4.82 (dd, J=65.0, 3.9 Hz, 1H), 4.17-4.14 (m, 2H), 3.90 (dd, J=27.9, 10.2 Hz, 1H), 3.15 (dd, J=39.7, 10.1 Hz, 1H), 2.56 (dd, J=10.7, 4.3 Hz, 1H), 2.41-2.30 (m, 2H), 2.16-1.97 (m, 5H), 1.95-1.78 (m, 1H), 1.75-1.65 (m, 1H), 1.42 (s, 4.5H), 1.40 (s, 4.5H), 1.23 (t, J=4.3 Hz, 3H) ppm.

Scale-Up Batch: Crude I-01 (393.9 mmol) from a previous reaction was dissolved in methylene chloride (1.8 L) and triethylamine (219.3 mL, 1573 mmol) was added. After stirring for 15 minutes, a solution of di-tert-butyl-dicarbonate (343.3 g, 1573 mmol) in methylene chloride (300 mL) was added. The resulting mixture was stirred overnight at room temperature and then concentrated under vacuum. The resulting solid was suspended in ethyl acetate (900 mL) and filtered. The filtrate was washed with 1 N HCl (180 mL) and brine (100 mL). The organic phase was dried over sodium sulfate, filtered, and concentrated under vacuum. The resulting colorless oil (151 g crude, quantitative yield) which was used directly without further purification.

Preparation of (3S,4aS,8aR)-2-[(tert-butoxy)carbonyl]-6-oxo-decahydroisoquinoline-3-carboxylic acid (I-04)

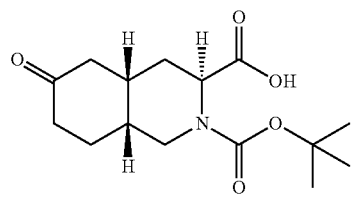

I-04

To a solution of I-03 (35.2 g, 108 mmol) in THF (100 mL) was added 2 N NaOH (486 mL, 972 mmol) at room temperature under nitrogen atmosphere. The solution was stirred at room temperature for 24 h and then concentrated under vacuum to remove most of the THF. The aqueous layer was extracted with MTBE (3×150 mL) to remove organic impurities, acidified with 1 N HCl to pH ~2, and extracted with ethyl acetate (4×300 mL). The combined organic layers were washed with brine (250 mL), dried over sodium sulfate, and concentrated under vacuum to afford I-04 as a white foaming solid (24.9 g, 78% yield). $^1$H NMR (300.13 MHz, CDCl$_3$) δ 4.92 (d, J=58.3 Hz, 1H), 3.95 (dd, J=29.7, 10.1 Hz, 1H), 3.21 (dd, J=32.9, 10.2 Hz, 1H), 2.61 (d, J=10.2 Hz, 1H), 2.42-1.71 (m, 9H), 1.46 (s, 4.5H), 1.44 (s, 4.5H) ppm.

Scale-Up Batch: To a solution of I-03 (Crude 151 g, 393.9 mmol) in THF (360 mL) was added 2 N NaOH (1772 mL, 3545 mmol) at room temperature under nitrogen atmosphere. The solution was stirred at room temperature for 24 h and then concentrated under vacuum to remove most of the THF. The aqueous layer was extracted with MTBE (3×250 mL) to remove organic impurities, acidified with 1 N HCl to pH ~2, and extracted with ethyl acetate (4×600 mL). The combined organic layers were washed with brine (500 mL), dried over sodium sulfate, and concentrated under vacuum to afford I-04 as a white foaming solid (122 g crude, quantitative yield).

Preparation of (3S,4aS,8aR)-2-[(tert-butoxy)carbonyl]-6-oxo-decahydroisoquinoline-3-carboxylic acid (I-05)

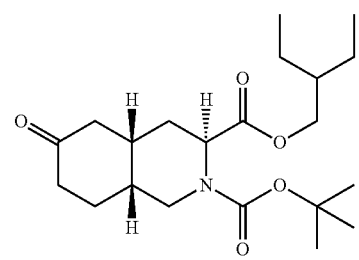

I-05

To a solution of I-04 (24.9 g, 83.7 mmol) in DMF (110 mL) was added solid NaHCO$_3$ (49.4 g, 588 mmol) and 3-(iodomethyl)pentane (23.33 g, 110 mmol) at room temperature under nitrogen atmosphere and the mixture was stirred at 35-40° C. for 4 h. The reaction was monitored by HPLC and after completion of the reaction the mixture was filtered, and the solid was washed with acetonitrile (400 mL). The combined organic layers were concentrated and the crude residue obtained was re-dissolved in ethyl acetate (500 mL). The solution was washed with water (300 mL), brine (300 mL), dried over sodium sulfate, and concentrated under vacuum. The residue was purified by flash column chromatography (silica gel, 0% to 40% ethyl acetate/hexane) to afford I-05 as a red semi-solid (15.2 g, 49% yield pure and 3.5 g, 11% yield less pure). $^1$H NMR (300.13 MHz, CDCl$_3$) δ 4.86 (d, J=63.5 Hz, 1H), 4.16-3.97 (m, 2.5H), 3.88 (d, J=10.1 Hz, 0.5H), 3.15 (dd, J=31.3, 9.8 Hz, 1H), 2.58 (d, J=8.4 Hz, 1H), 2.35 (m, 2H), 2.18-1.48 (m, 8H), 1.44 (m, 9H), 1.40-1.30 (m, 4H), 0.87 (m, 6H) ppm.

Scale-Up Batch: To a solution of crude I-04 (426.8 mmol) in DMF (500 mL) was added solid NaHCO$_3$ (231.6 g, 2.76 mol) and 3-(iodomethyl)pentane (159.7 g, 754.5 mmol) at room temperature under nitrogen atmosphere and the mixture was stirred at 35-40° C. for 3 days. The reaction was monitored by HPLC and after completion of the reaction the mixture was filtered, and the solid was washed with acetonitrile (1.5 L). The combined organic layers were concentrated and the crude residue obtained was re-dissolved in ethyl acetate (2 L). The solution was washed with water (500 mL), brine (500 mL), dried over sodium sulfate, and concentrated under vacuum to obtain crude product I-05 as a red semi-solid (92.6 g, 57% yield) which was used directly without further purification.

Preparation of 2-tert-butyl 3-nonyl (3S,4aS,8aR)-6-oxo-decahydroisoquinoline-2,3-dicarboxylate (I-06)

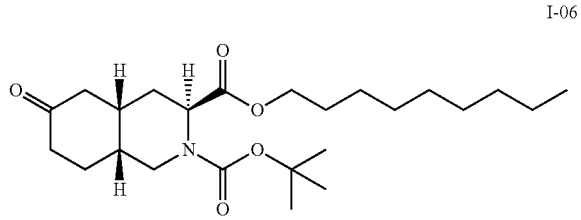 [SMILES: CCCCCCCCCOC(=O)[C@@H]1C[C@H]2CC(=O)CC[C@H]2CN1C(=O)OC(C)(C)C]

I-06

To a solution of I-04 (0.5 mmol) in DMF (2.0 mL) is added NaHCO₃ (3.5 mmol) and 1-iodononane (1.3 mmol) at room temperature under nitrogen atmosphere and the mixture is stirred at room temperature for 24 h. The reaction is monitored by HPLC and after completion of the reaction is poured into water (30 mL) and extracted ethyl acetate (2×30 mL). The combined organic layers are dried over sodium sulfate, and concentrated under vacuum. The resulting residue is purified by flash column chromatography (silica gel, ethyl acetate/hexane) to afford I-06.

Preparation of 3-(2R)-butan-2-yl 2-tert-butyl (3S,4aS,8aR)-6-oxo-decahydroisoquinoline-2,3-dicarboxylate (I-07)

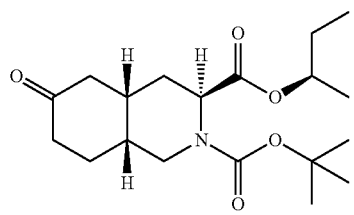 [SMILES: CC[C@@H](C)OC(=O)[C@@H]1C[C@H]2CC(=O)CC[C@H]2CN1C(=O)OC(C)(C)C]

To a mixture of I-04 (0.5 mmol) and (2R)-butanol (0.6 mmol) in dichloromethane (1.0 mL) is added DCC (0.6 mmol) and catalytic DMAP under nitrogen atmosphere. The mixture is stirred at room temperature for 18 h and monitored by TLC or HPLC. Upon completion, acetonitrile (10 mL) is added and the mixture is stirred for 5-10 min. The solid precipitate is removed by filtration through a sintered glass-funnel and the solid is washed with acetonitrile (10 mL). The filtrate is concentrated under vacuum and the residue is purified by flash column chromatography (silica gel, ethyl acetate/hexane) to afford I-07.

Synthesis of Olefin Compounds IX

Preparation of 2-benzyl 3-ethyl (3S,4aR,6E,8aR)-6-[2-(1H-1,2,3,4-tetrazol-5-yl)ethylidene]-decahydroisoquinoline-2,3-dicarboxylate (I-08)

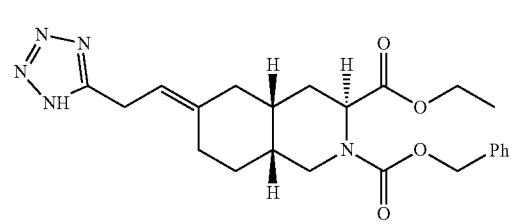

I-08

To a solution of triphenyl[2-(1H-1,2,3,4-tetrazol-5-yl)ethyl]phosphonium bromide salt (VIII, 9.09 g, 20.7 mmol) and ketone (I-02, 6.2 g, 17.25 mmol) in anhydrous DMF (50 mL) was added 2.0 M NaHMDS (24.15 mL, 48.3 mmol) in THF at 0° C. to −10° C. under nitrogen atmosphere. The internal temperature of the reaction was maintained at 0° C. during addition. The mixture was stirred at this temperature for 30 min and then allowed to warm to room temperature. After stirring for 18 h at room temperature, the mixture was slowly quenched with an ice-cold brine solution (120 mL) and extracted with MTBE (7×250 mL) to partially remove triphenylphosphine oxide. The pH of the aqueous layer was adjusted to pH 2 using 3 N HCl and extracted with ethyl acetate (4×250 mL). The combined organic layers were washed with water (2×200 mL), brine (200 mL), dried over sodium sulfate, and concentrated under vacuum. The residue was purified by flash column chromatography (silica gel, 10% to 60% ethyl acetate/hexane) to afford I-08 as a pure white foaming solid (2.0 g, 26% yield) and as a less pure yellow oil (2.0 g, 26% yield). ¹H NMR (299.96 MHz, CDCl₃) δ 7.38-7.27 (m, 5H), 5.50 (t, J=6.7 Hz, 0.5H), 5.32 (dt, J=21.5, 6.4 Hz, 0.5H), 5.23-5.14 (m, 1.5H), 5.06 (d, J=12.9 Hz, 0.5H), 4.89 (d, J=27.0 Hz, 1H), 4.17 (q, J=6.8 Hz, 2H), 3.95-3.87 (m, 1H), 3.76-3.69 (m, 2H), 3.25 (d, J=14.3 Hz, 0.5H), 3.15 (d, J=12.9 Hz, 0.5H), 2.65 (d, J=12.6 Hz, 0.5H), 2.47 (d, J=13.8 Hz, 0.5H), 2.34 (d, J=13.2 Hz, 0.5H), 2.24 (d, J=11.4 Hz, 0.5H), 2.08-1.65 (m, 6H), 1.62-1.47 (m, 2H), 1.20 (d, J=7.8 Hz, 3H) ppm.

Preparation of 2-tert-butyl 3-ethyl (3S,4aR,8aR)-6-[2-(1H-1,2,3,4-tetrazol-5-yl)ethylidene]-decahydroisoquinoline-2,3-dicarboxylate (I-09)

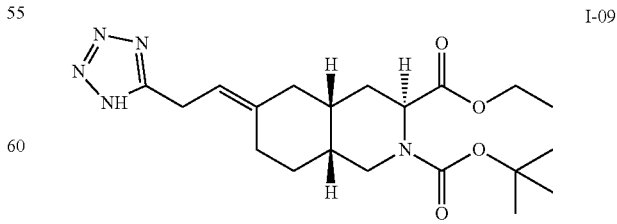

I-09

To a solution of triphenyl[2-(1H-1,2,3,4-tetrazol-5-yl)ethyl]phosphonium bromide salt (VIII, 6.16 g, 14.0 mmol) and ketone (I-03, 3.8 g, 11.7 mmol) in anhydrous DMF (35 mL) was added 2.0 M NaHMDS (16.4 mL, 32.8 mmol) in THF at 0° C. to −10° C. under nitrogen atmosphere. The internal temperature of the reaction was maintained at 0° C. during addition. The mixture was stirred at this temperature for 30 min and then allowed to warm to room temperature After stirring for 18 h at room temperature, the mixture was slowly quenched with an ice-cold brine solution (50 mL) and extracted with MTBE (8×60 mL) to partially remove triphenylphosphine oxide. The pH of the aqueous layer was adjusted to pH 2 using 3 N HCl and extracted with ethyl acetate (4×250 mL). The combined organic layers were washed with water (2×200 mL), brine (200 mL), dried over sodium sulfate, and concentrated under vacuum to afford I-09 as a red oil (6.1 g crude). $^1$H NMR (300.13 MHz, CDCl$_3$) δ 5.37 (m, 1H), 4.82 (dd, J=48.5, 3.5 Hz, 0.5H), 4.77 (d, J=45.5 Hz, 0.5H), 4.21-4.18 (m, 2H), 3.87-3.78 (m, 1H), 3.25-3.12 (m, 3H), 2.49-2.47 (m, 1.5H), 2.34 (d, J=13.1 Hz, 0.5H), 2.1.0-1.60 (m, 8H), 1.54-1.46 (m, 9H), 1.30-1.22 (m, 3H) ppm.

Preparation of 2-tert-butyl 3-(2-ethylbutyl) (3S,4aR, 8aR)-6-[2-(1H-1,2,3,4-tetrazol-5-yl)ethylidene]-decahydroisoquinoline-2,3-dicarboxylate (I-10)

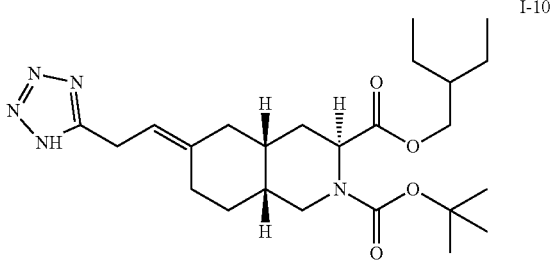 [SMILES: CCC(CC)COC(=O)[C@@H]1C[C@H]2C/C(=C/Cc3nnn[nH]3)CC[C@H]2CN1C(=O)OC(C)(C)C]

I-10

To a solution of tetrazole Wittig salt (VIII, 23.37 g, 53.2 mmol) and ketone (I-04, 16.9 g, 44.3 mmol) in anhydrous DMF (150 mL) was added 2.0 M NaHMDS (62 mL, 124 mmol) in THF at 0° C. to −10° C. under nitrogen atmosphere. The internal temperature of the reaction was maintained at 0° C. during addition. The mixture was stirred at this temperature for 30 min and then allowed to warm to room temperature After stirring for 2 h at room temperature, the mixture was slowly quenched with 10% brine solution (200 mL) and extracted with MTBE (4×300 mL) to partially remove triphenylphosphine oxide. The pH of the aqueous layer was adjusted to pH 2 using 3 N HCl and extracted with ethyl acetate (4×300 mL). The combined organic layers were washed with water (2×150 mL), brine (200 mL), dried over sodium sulfate, and concentrated under vacuum. The residue was purified by flash column chromatography (silica gel, 0% to 50% ethyl acetate/hexane) to afford I-10 as foaming solid (13.1 g, 64% yield pure) and as a pale yellow semi-solid (2.6 g, 13% yield, less pure). $^1$H NMR (299.96 MHz, CDCl$_3$) δ 5.55 (t, J=7.0 Hz, 0.4H), 5.38 (dt, J=20.3, 16.8 Hz, 0.6H), 4.84 (d, J=46.8 Hz, 1H), 4.09-4.00 (m, 2H), 3.89-3.73 (m, 3H), 3.14-3.03 (m, 1H), 2.69 (t, J=10.6 Hz, 0.6H), 2.49 (dd, J=13.6, 6.1 Hz, 0.4H), 2.34 (d, J=13.5 Hz, 0.6H), 2.31-2.21 (m, 0.4H), 2.09 (d, J=14.7 Hz, 1H), 2.01 (t, J=11.7 Hz, 1H), 1.90-1.75 (m, 4H), 1.65-1.40 (m, 3H), 1.45 (s, 9H), 1.40-1.26 (m, 5H), 0.91-0.85 (m, 6H) ppm.

Scale-Up Batch: To a solution of tetrazole Wittig salt (VIII, 121.8 g, 277.3 mmol) and crude ketone (I-04, 88 g, 230.7 mmol) in anhydrous DMF (670 mL) was added 2.0 M NaHMDS (323.3 mL, 646.6 mmol) in THF at 0° C. to −10° C. under nitrogen atmosphere. The internal temperature of the reaction was maintained at 0° C. during addition. The mixture was stirred at this temperature for 30 min and then allowed to warm to room temperature After stirring for 2 h at room temperature, the mixture was slowly quenched with 10% brine solution (500 mL) and extracted with MTBE (2×400 mL) to partially remove triphenylphosphine oxide. The pH of the aqueous layer was adjusted to pH 2 using 3 N HCl and extracted with ethyl acetate (4×1 L). The combined organic layers were washed with water (2×1 L), brine (500 mL), dried over sodium sulfate, and concentrated under vacuum. The residue was purified by flash column chromatography (silica gel, 0% to 50% ethyl acetate/hexane) to afford I-10 as foaming solid (51.6 g, 49% yield).

Synthesis of Fluorinated Carbamate Esters X

Preparation of 2-benzyl 3-ethyl (3S,4aS,8aR)-6-fluoro-6-[2-(1H-1,2,3,4-tetrazol-5-yl)ethyl]-decahydroisoquinoline-2,3-dicarboxylate (I-11)

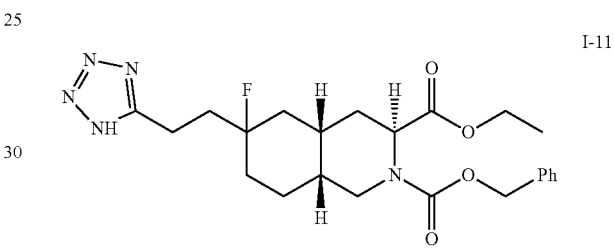

I-11

A 3-necked, 500 mL flask was prepared with a nitrogen inlet, temperature probe, and cooling bath. Water (85 mL) was charged into the flask, followed by iron (III) nitrate nonahydrate (Fe(NO$_3$)$_3$·9 H$_2$O (1.46 g, 3.04 mmol) and the mixture was stirred until dissolved (Solution A). Acetonitrile (85 mL) was charged into a 500 mL round-bottomed flask, followed by I-08 (667 mg, 1.517 mmol) and Selectfluor® (1.61 g, 4.55 mmol), and the mixture was stirred until dissolved (Solution B). Solution B was charged into Solution A while stirring at 22-25° C. A clear yellow solution was observed and the pH of the solution was measured to be pH 2. The reaction was degassed using nitrogen bubbling for 10 min and the mixture was cooled to −10° C. Sodium borohydride (591.2 mg) was charged in 4 installments as a solid over 5-10 min. The mixture was stirred at −10° C. for 2 h, then the mixture was warmed to 22-25° C. and stirring was continued for 5 h monitoring by HPLC. The mixture was concentrated to remove acetonitrile under vacuum using a rotary evaporator. To this mixture was added 1 N HCl (110 mL) while stirring and maintaining the temperature below 25° C., to adjust to pH 2. The solution was extracted with ethyl acetate (4×100 mL). The organic layers were washed with water (2×100 mL) and brine (100 mL), the solution was dried over sodium sulfate and concentrated under vacuum using a rotary evaporator to afford crude product (690 mg, 100%). The resulting residue was purified by flash column chromatography (silica gel, 0% to 6% methanol/dichloromethane) to afford I-11 as a white forming solid (590 mg, 85% yield). $^1$H NMR (299.96 MHz, CDCl$_3$) δ 7.35-7.26 (m, 5H), 5.25-5.09 (m, 2H), 4.93 (dd, J=24.9, 5.4 Hz, 0.6H), 4.62 (m, 0.4H), 4.21-4.10 (m, 2H), 4.00 (t, J=11.2 Hz, 0.6H), 3.61 (dd, J=12.9, 6.6 Hz, 0.4H), 3.43 (dd, J=13.5, 3.6 Hz, 0.4H), 3.27 (t, J=14.5 Hz, 0.6H), 3.17-3.05 (m, 2H), 2.39-1.36 (m, 12H), 1.27-1.21 (m, 3H) ppm.

Preparation of 2-tert-butyl 3-ethyl (3S,4aS,8aR)-6-fluoro-6-[2-(1H-1,2,3,4-tetrazol-5-yl)ethyl]-decahydroisoquinoline-2,3-dicarboxylate (I-12)

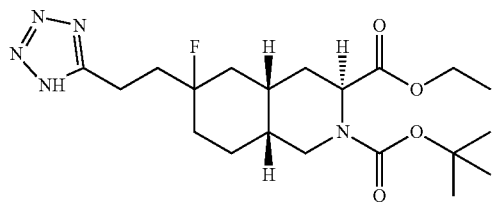

I-12

A 3-necked, 3-L flask was prepared with a nitrogen inlet, temperature probe, and cooling bath. Water (1.0 L) was charged into the flask, followed by iron (III) nitrate nonahydrate ($Fe(NO_3)_3 \cdot 9\,H_2O$, 44.17 g, 109.34 mmol) and the mixture was stirred until dissolved (Solution A). Acetonitrile (1.0 L) was charged into a 2-L round-bottomed flask, followed by I-09 (14.3 g, 35.27 mmol) and Selectfluor® (38.73 g, 109 mmol), and the mixture was stirred until dissolved (Solution B). Solution B was charged into Solution A while stirring at 22-25° C. A clear yellow solution was observed and the pH of the solution was measured to be pH 2. The reaction was degassed using nitrogen bubbling for 30 min and the mixture was cooled to −10° C. Sodium borohydride (13.34 g, 353 mmol) was charged in ten installments as a solid over 10-15 min. The mixture was stirred at −10° C. for 2 h, then the mixture was warmed to 22-25° C. and stirring was continued for 5 h while monitoring by HPLC. The mixture was concentrated under vacuum to remove acetonitrile using a rotary evaporator. To this mixture was added 1 N HCl (500 mL) while stirring and maintaining the temperature below 25° C., the mixture was adjusted to pH 2. The solution was extracted with ethyl acetate (4×500 mL). The combined organic layers were washed with water (2×500 mL) and brine (100 mL), dried over sodium sulfate, and concentrated under vacuum using a rotary evaporator to afford crude product (13.5 g, 90%). The resulting residue was purified by flash column chromatography (silica gel, 0% to 70% ethyl acetate/heptane) to afford I-12 as white foaming solid (11.36 g, 76% yield) as a mixture of diastereomers. $^1$H NMR (299.962 MHz, CDCl$_3$) δ 4.86 (dd, J=51.3, 5.1 Hz, 0.5H), 4.49 (t, J=5.1 Hz, 0.5H), 4.25-4.14 (m, 2H), 3.90 (t, J=15.0 Hz, 0.5H), 3.47 (dd, J=13.3, 7.3 Hz, 0.5H), 3.37 (dd, J=13.2, 4.8 Hz, 0.5H), 3.22-3.14 (m, 2H), 3.14-3.04 (m, 0.5H), 2.34-1.53 (m, 12H), 1.49-1.46 (m, 9H), 1.27 (t, J=6.8 Hz, 3H) ppm.

Preparation of 2-tert-butyl 3-(2-ethylbutyl) (3S,4aS,8aR)-6-fluoro-6-[2-(1H-1,2,3,4-tetrazol-5-yl)ethyl]-decahydroisoquinoline-2,3-dicarboxylate (I-13)

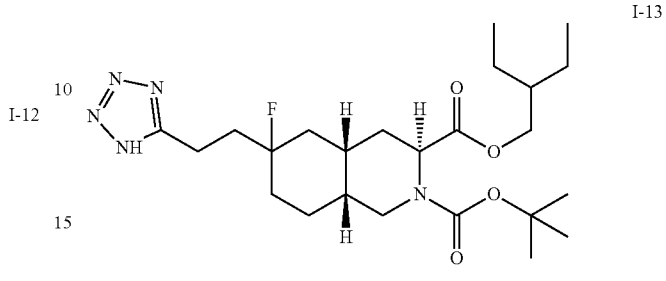

I-13

A 3-necked, 2-L flask was prepared with a nitrogen inlet, temperature probe, and cooling bath. Water (400 mL) was charged into the flask, followed by iron (III) nitrate nonahydrate ($Fe(NO_3)_3 \cdot 9\,H_2O$, 34.2 g, 84.63 mmol) and the mixture was stirred until dissolved (Solution A). Acetonitrile (400 mL) was charged into a 1-L round-bottomed flask, followed by I-10 (12.6 g, 27.3 mmol) and Selectfluor® (30 g, 84.63 mmol), and the mixture was stirred until dissolved (Solution B). Solution B was charged into Solution A while stirring at 22-25° C. A clear yellow solution was observed and the pH of the solution was measured to be pH 2. The reaction was degassed using nitrogen bubbling for 30 min and the mixture was cooled to −10° C. Sodium borohydride (10.33 g, 273 mmol) was charged in ten installments as a solid over 10-15 min. The mixture was stirred at −10° C. for 2 h, then the mixture was warmed to 22-25° C. and stirring was continued for 5 h monitoring by HPLC. The mixture was concentrated under vacuum to remove acetonitrile using a rotary evaporator. To this mixture was added 1 N HCl (~300 mL) while stirring and maintaining the temperature below 25° C., the mixture was adjusted to pH 2. The solution was extracted with ethyl acetate (3×350 mL). The combined organic layers were washed with water (400 mL) and brine (300 mL), dried over sodium sulfate, and concentrated under vacuum using a rotary evaporator to afford crude product. The resulting residue was purified by flash column chromatography (silica gel, 0% to 50% ethyl acetate/heptane) to afford I-13 as white foaming solid (8.03 g, 61% yield) as a mixture of diastereomers. $^1$H NMR (299.96 MHz, CDCl$_3$) δ 5.55 (t, J=7.0 Hz, 0.4H), 5.38 (dt, J=20.3, 16.8 Hz, 0.6H), 4.84 (d, J=46.8 Hz, 1H), 4.09-4.00 (m, 2H), 3.89-3.73 (m, 3H), 3.14-3.03 (m, 1H), 2.69 (t, J=10.6 Hz, 0.6H), 2.49 (dd, J=13.6, 6.1 Hz, 0.4H), 2.34 (d, J=13.5 Hz, 0.6H), 2.31-2.21 (m, 0.4H), 2.09 (d, J=14.7 Hz, 1H), 2.01 (t, J=11.7 Hz, 1H), 1.90-1.75 (m, 4H), 1.65-1.40 (m, 3H), 1.45 (s, 9H), 1.40-1.26 (m, 5H), 0.91-0.85 (m, 6H) ppm.

Scale-Up Batch: A 3-necked, 5-L flask was prepared with a nitrogen inlet, temperature probe, and cooling bath. Water (1.5 L) was charged into the flask, followed by iron (III) nitrate nonahydrate ($Fe(NO_3)_3 \cdot 9\,H_2O$, 72.3 g, 178.96 mmol) and the mixture was stirred until dissolved (Solution A). Acetonitrile (1.5 L) was charged into a 3-L round-bottomed flask, followed by I-10 (26.6 g, 57.9 mmol) and Selectfluor® (63.4 g, 178.96 mmol), and the mixture was stirred until dissolved (Solution B). Solution B was charged into Solution A while stirring at 22-25° C. A clear yellow solution was observed and the pH of the solution was measured to be pH 2. The reaction was degassed using nitrogen bubbling for 30 min and the mixture was cooled to −10° C. Sodium borohydride (21.8 g, 576.2 mmol) was charged in ten installments as a solid over 10-15 min. The mixture was stirred at −10° C. for 2 h, then the mixture was warmed to 22-25° C. and stirring was continued for 5 h monitoring by HPLC. The mixture was concentrated under vacuum to remove acetonitrile using a rotary evaporator. To this mixture was added 1 N HCl (~640 mL) while stirring and maintaining the temperature below 25° C., the mixture was adjusted to pH 2. The solution was extracted with ethyl acetate (3×500 mL). The combined organic layers were washed with water (500 mL) and brine (500 mL), dried over sodium sulfate, and concentrated under vacuum using a rotary evaporator to afford crude product. The resulting residue was purified by flash column chromatography (silica gel, 0% to 50% ethyl acetate/heptane) to afford I-13 as white foaming solid (21.7 g, 61% yield) as a mixture of diastereomers.

Preparation of (3S,4aS,8aR)-2-[(benzyloxy)carbonyl]-6-fluoro-6-[2-(2H-1,2,3,4-tetrazol-5-yl)ethyl]-decahydroisoquinoline-3-carboxylic acid (I-14)

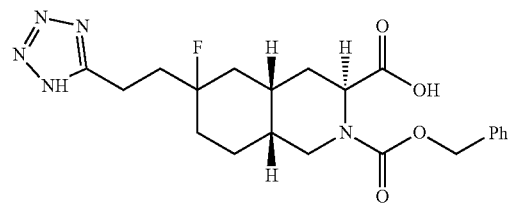

I-14

Compound I-11 (0.59 g, 1.28 mmol) was dissolved in 9:1 ethanol-water (2.0 mL) and 2N NaOH (5.3 mL) was added. The mixture was stirred at room temperature for 4 h. The reaction was diluted with water (50 mL) and extracted with MTBE (50 mL) to remove the organic impurities. The aqueous layer was acidified with 6N HCl to pH ~2. The mixture was extracted with ethyl acetate (3×50 mL) and washed with brine (50 mL). The organic layers were combined, dried over sodium sulfate, and concentrated under vacuum using a rotary evaporator to afford crude product I-14 as a white solid (435 mg, 79% yield). The crude product was used without further purification directly in a subsequent step.

Preparation of (3S,4aS,8aR)-2-[(tert-butoxy)carbonyl]-6-fluoro-6-[2-(1H-1,2,3,4-tetrazol-5-yl)ethyl]-decahydroisoquinoline-3-carboxylic acid (I-15)

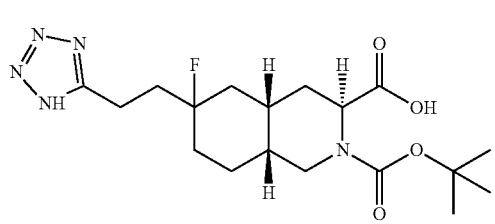

I-15

Compound I-12 (185 mg, 0.435 mmol) was dissolved in 9:1 ethanol-water (1.0 mL) and 2N NaOH (2.5 mL) was added. The mixture was stirred at room temperature for 4 h. The reaction was diluted with water (50 mL) and extracted with MTBE (50 mL) to remove the organic impurities. The aqueous layer was acidified with 6N HCl to pH ~2. The mixture was extracted with ethyl acetate (3×50 mL) and washed with brine (50 mL). The organic layers were combined, dried over sodium sulfate, and concentrated under vacuum using a rotary evaporator to afford crude product (183 mg), which was purified by silica gel column chromatography (using an ISCO gradient system 0% to 10% methanol-dichloromethane) to afford I-15 as an oil (143 mg, 83% yield). This material was used directly in a subsequent step.

Preparation of 2-benzyl 3-cyclohexyl (3S,4aS,8aR)-6-fluoro-6-[2-(1H-1,2,3,4-tetrazol-5-yl)ethyl]-decahydroisoquinoline-2,3-dicarboxylate (I-16)

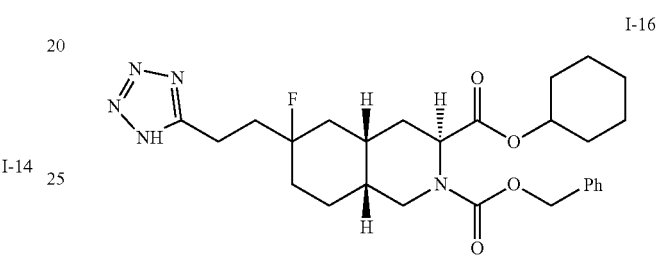

I-16

Compound I-14 (51.5 mg, 0.12 mmol) and cyclohexanol (14.4 mg, 0.144 mmol) were dissolved in dichloromethane (1 mL). Diisopropylcarbodiimide (20 mg, 0.16 mmol) and catalytic 4-dimethylaminopyridine (5 mg, 0.04 mmol) were added to the mixture under nitrogen atmosphere and the reaction was stirred at room temperature for 16-18 h. The reaction was monitored by HPLC, and upon completion, acetonitrile (1 mL) was added and the mixture was stirred for 5-10 min. The solid precipitate was removed by filtration through a sintered glass-funnel and the solid was washed with acetonitrile (5 mL). The filtrate was concentrated under vacuum and the residue was purified by silica gel flash column chromatography (0% to 5% methanol/dichloromethane) to afford I-16 as a colorless oil (40.4 mg, 66% yield). $^1$H NMR (299.96 MHz, CDCl$_3$) δ 7.35-7.27 (m, 5H), 5.23-5.07 (m, 2H), 4.95-4.50 (m, 2H), 3.97 (t, J=12.3 Hz, 0.4H), 3.89-3.73 (m, 0.4H), 3.61 (dd, J=13.6, 6.7 Hz, 0.4H), 3.40 (dd, J=12.9, 4.2 Hz, 0.3H), 3.32-3.20 (m, 0.5H), 3.16-3.05 (m, 2H), 2.34-1.65 (m, 13H), 1.51-1.25 (m, 8H), 1.16 (d, J=6.3 Hz, 1H) ppm.

Preparation of 2-benzyl 3-octyl (3S,4aS,8aR)-6-fluoro-6-[2-(1H-1,2,3,4-tetrazol-5-yl)ethyl]-decahydroisoquinoline-2,3-dicarboxylate (I-17)

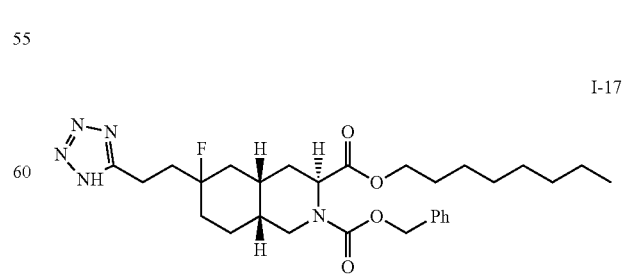

I-17

Compound I-14 (54.8 mg, 0.127 mmol) and 1-octanol (20 mg, 0.153 mmol) were dissolved in dichloromethane (1.0 mL). Dicyclohexylcarbodiimide (35 mg, 0.168 mmol) and catalytic 4-dimethylaminopyridine (5 mg, 0.037 mmol) were added to the mixture under nitrogen atmosphere and the reaction was stirred at room temperature for 16-18 h. The reaction was monitored by HPLC, and upon completion, the solid precipitate was removed by filtration through a sintered glass-funnel and the solid was washed with acetonitrile (5 mL). The filtrate was concentrated under vacuum and the residue was purified by silica gel flash column chromatography (0% to 5% methanol/dichloromethane) to afford I-17 as a colorless oil (40.2 mg, 58% yield). $^1$H NMR (299.96 MHz, CDCl$_3$) δ 7.40-7.25 (m, 5H), 5.25-5.10 (m, 2H), 4.94 (d, J=25.5 Hz, 0.65H), 4.65 (s, 0.35H), 4.10-3.95 (m, 3H), 3.70-3.60 (m, 1H), 3.45-3.20 (m, 1H), 3.19-3.05 (m, 2H), 2.35-1.56 (m, 24H), 0.87 (m, 3H) ppm.

Synthesis of Fluorinated Ester Amine Prodrugs XI

Preparation of ethyl (3S,4aS,6S,8aR)-6-fluoro-6-[2-(1H-1,2,3,4-tetrazol-5-yl)ethyl]-decahydroisoquinoline-3-carboxylate (3)

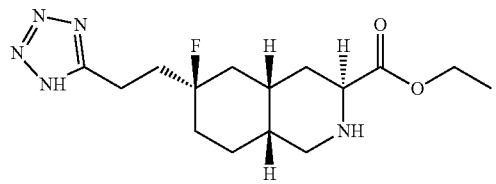

3

Compound I-12 (4.14 g, 9.73 mmol) was dissolved in 7:1 dioxane-anisole (57 mL, 0.17 M) and treated with 4 N HCl in dioxane (10 eq, 24 mL). After 1 h at room temperature, the reaction was checked by HPLC, which showed the reaction was not complete. Additional 4 N HCl (5 eq, 12 mL) was added and continue was stirring at room temperature. After 1 h, HPLC showed the reaction was not complete and so more 4 N HCl (5 eq, 12 mL) was added. After 30 min, HPLC again showed incomplete reaction and so more 4 N HCl (2 eq, 5 mL) was added. The reaction was complete after 4 h. Nitrogen gas was bubbled into the reaction to purge the solution of excess HCl and then the solvent was partially evaporated under vacuum to half the volume. Hexanes was added to precipitate the HCl salt and the supernatant was discarded. The residue was triturated with dioxane (2 mL), the hexanes (2 mL) was added to fully precipitate the HCl salt of the desired product. The residue was dried under vacuum to afford crude product 3 (3.48 g, 99 3% yield) as a mixture of fluorinated diastereomer isomers. The residue was purified by SFC chromatography (Analytical SFC Method—Column: 4.6×100 mm Chromegabond Ethyl Pyridine (ES Industries, West Berlin, N.J.); Solvent A: CO$_2$, Solvent B: Methanol with 0.1% triethylamine; Gradient Method: 5%-65% B over 4 minutes, hold at 65% B for one minute and return to initial conditions at 4 mL/min; System Pressure: 125 bar; Column Temperature: 40° C.; Sample Diluent: Methanol; Retention Time (3): 2.07 min; Retention Time (C6-F-Isomer): 1.06 min. Preparative SFC Method—Column: 3.0×25.0 cm 2-Ethylpyridine (Princeton Chromatography Inc., Princeton, N.J.); Solvent A: CO$_2$, Solvent B: Methanol with 0.5% triethylamine; Isocratic Method: 25% Solvent B at 100 g/min; System Pressure: 100 bar; Column Temperature: 25° C.; Sample Diluent: Methanol with 0.5% triethylamine) to afford 3 as a semi-solid (414 mg, 96.2% isomeric purity). The material was further purified via Gilson reverse phase chromatography (5% to 50% acetonitrile with 0.1% TFA-water with 0.1% TFA and then 5% to 95% acetonitrile-water) to provide pure compound for testing. $^1$H NMR (299.96 MHz, CD$_3$OD) δ 4.31 (q, J=7.1 Hz, 2H), 4.04 (dd, J=12.9, 3.9 Hz, 1H), 3.20 (t, J=13.0 Hz, 1H), 3.09 (dd, J=12.7, 4.3 Hz, 1H), 3.00 (t, J=8.1 Hz, 2H), 2.33-2.42 (m, 1H), 2.15-1.90 (m, 7H), 1.84-1.65 (m, 3H), 1.57-1.45 (m, 1H), 1.32 (t, J=7.2 Hz, 3H) ppm. $^{19}$F NMR (282.22 MHz, CD$_3$OD) δ −160.70 (m, uncorrected, TFA reference −76.97) ppm. Mass Analysis (ES+)=326.24 [M+H] (Formula: C$_{15}$H$_{24}$FN$_5$O$_2$, Exact Mass: 325.19).

Preparation of 2-ethylbutyl (3S,4aS,6S,8aR)-6-fluoro-6-[2-(1H-1,2,3,4-tetrazol-5-yl)ethyl]-decahydroisoquinoline-3-carboxylate (4)

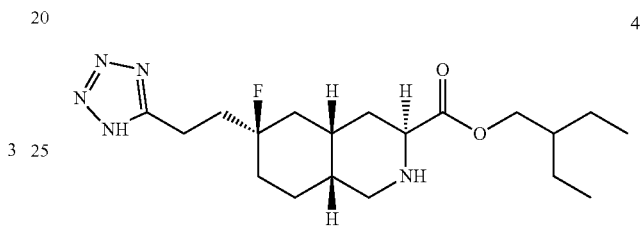

4

To a solution of I-13 (2.2 g, 4.57 mmol) in anhydrous THF (15 mL) was added 4 N HCl in dioxane (11.4 mL, 45.7 mmol) at room temperature while stirring. After stirring for 4 h at room temperature, the reaction was shown to be complete by HPLC. Nitrogen gas was bubbled into the reaction mixture to purge out the excess HCl and the solvent was partially evaporated under vacuum to half the volume. The mixture was diluted with 1:1 MTBE-Heptane (15 mL) resulting in separation of an oily layer, which was triturated and the supernatant discarded. The oily residue was triturated again with 1:1 MTBE-Heptane (15 mL) to further remove lipophilic impurities and the supernatant was discarded. The oily residue was placed under vacuum to remove residual solvent and to afford crude product as a white solid and a mixture of fluorinated diastereomers which was further dried under high vacuum to constant weight (1.6 g crude, 84% yield). The residue was purified by SFC chromatography (Analytical SFC Method—Column: 4.6× 100 mm Chiralpak IC SFC (Chiral Technologies, West Chester, Pa.); Solvent A: CO$_2$, Solvent B: Ethanol with 0.1% triethylamine; Gradient Method: 5%-65% Solvent B over 4 minutes at 4 mL/min; System Pressure: 125 bar; Column Temperature: 40° C.; Sample Diluent: Ethanol; SFC Retention Time (4): 3.40 min; Preparative SFC Method—Column: 2.1×25.0 cm Chiralpak IC (Chiral Technologies, West Chester, Pa.); Solvent A: CO$_2$, Solvent B: Ethanol with 0.25% triethylamine; Isocratic Method: 40% Solvent B at 70 g/min; System Pressure: 100 bar; Column Temperature: 25° C.; Sample Diluent: Ethanol with 0.25% triethylamine) to afford 4 as a thick colorless oil (96.9% isomeric purity). The material was further purified via Gilson reverse phase chromatography (15% to 60% acetonitrile with 0.1% TFA-water with 0.1% TFA and then 10% to 98% acetonitrile-water) to provide pure compound for testing. $^1$H NMR (299.96 MHz, CD$_3$OD) δ 4.21 (ddd, J=20.6, 10.9, 5.6 Hz, 2H), 4.07 (dd, J=12.6, 4.2 Hz, 1H), 3.19 (t, J=13.0 Hz, 1H), 4.07 (dd, J=12.6, 4.2 Hz, 1H), 2.98 (t, J=7.9 Hz, 2H), 2.33-2.42 (m, 1H), 2.13-1.90 (m, 6H), 1.84-1.65 (m, 3H), 1.60-1.30 (m, 7H), 0.93 (t, J=7.2 Hz, 6H) ppm. $^{19}$F NMR (282.22 MHz, CD$_3$OD) δ −160.46 (m, uncorrected, TFA reference −76.95) ppm. Mass Analysis (ES+)=282.23 [M+H] (Formula: C$_{19}$H$_{32}$FN$_5$O$_2$, Exact Mass: 381.25).

Scale-Up Batch: To a solution of I-13 (21.7 g, 45.06 mmol) in anhydrous THF (15 mL) was added 4 N HCl in dioxane (112.5 mL, 450.0 mmol) at room temperature while stirring. After stirring for 4 h at room temperature, the reaction was shown to be complete by HPLC. Nitrogen gas was bubbled into the reaction mixture to purge out the excess HCl and the solvent was partially evaporated under vacuum to half the volume. The mixture was diluted with 1:1 MTBE-Heptane (150 mL) resulting in separation of an oily layer which was triturated and the supernatant discarded. The oily residue was triturated again with 1:1 MTBE-Heptane (150 mL) to further remove lipophilic impurities and the supernatant was discarded. The oily residue was placed under vacuum to remove residual solvent and to afford crude product as a white solid and a mixture of fluorinated diastereomers which was further dried under high vacuum to constant weight (14 g crude, 75% yield). The residue was purified by SFC chromatography (Analytical SFC Method—Column: 4.6×100 mm Chiralpak IC SFC (Chiral Technologies, West Chester, Pa.); Solvent A: CO$_2$, Solvent B: Ethanol with 0.1% ammonium hydroxide; Gradient Method: 5%-65% Solvent B over 4 minutes at 4 mL/min; System Pressure: 125 bar; Column Temperature: 40° C.; Sample Diluent: Ethanol; SFC Retention Time (4): 2.90 min; Preparative SFC Method 1—Column: 2.1×25.0 cm Chiralpak IC (Chiral Technologies, West Chester, Pa.); Solvent A: CO$_2$, Solvent B: Ethanol with 0.25% ammonium hydroxide; Isocratic Method: 35% Solvent B at 70 g/min; System Pressure: 100 bar; Column Temperature: 25° C.; Sample Diluent: Ethanol with 0.25% ammonium hydroxide; Preparative SFC Method 2—Column: 2.0×25.0 cm PVA-Sil (YMC, Allentown, Pa.); Solvent A: CO$_2$, Solvent B: Ethanol with 0.25% ammonium hydroxide; Isocratic Method: 50% Solvent B at 80 g/min; System Pressure: 100 bar; Column Temperature: 25° C.; Sample Diluent: Ethanol with 0.25% ammonium hydroxide). The desired diastereomer fraction was then further purified via reverse phase chromatography (Column: 19×50 mm XBridge OBD Prep C18 5 μm, 5% acetonitrile and 95% water with 0.1% ammonium hydroxide for 2 minutes and then 5% to 95% acetonitrile-water with 0.1% ammonium hydroxide for 3 minutes; Flow Rate: 25 mL/min; Column Temperature: 40° C.; Sample Diluent: 2:1:1 Ethanol:Acetonitrile:Water). The desired fractions were concentrated via rotary evaporation at 35° C. The dried material was reconstituted in 1:1 acetonitrile:water and the solution was concentrated via rotary evaporation to remove the acetonitrile and then frozen and lyophilized to afford 4 as a white solid (2.42 g, 90% purity, 97.8% ee).

Preparation of 2-ethylbutyl (3S,4aS,6R,8aR)-6-fluoro-6-[2-(1H-1,2,3,4-tetrazol-5-yl)ethyl]-decahydroisoquinoline-3-carboxylate (5)

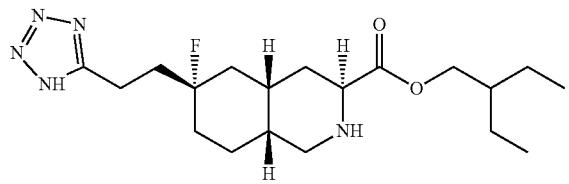

SFC chromatography to provide compound 4 also provided the C6-F-Isomer 5 (SFC Retention Time: 3.04 min) as a thick colorless oil (97.9% isomeric purity). The material was further purified via Gilson reverse phase chromatography (15% to 60% acetonitrile with 0.1% TFA-water with 0.1% TFA and then 10% to 98% acetonitrile-water) to provide pure compound for testing. $^1$H NMR (299.96 MHz, CD$_3$OD) δ 4.30-4.25 (m, 2H), 4.18 (dd, J=10.9, 5.5 Hz, 1H), 3.35-3.27 (m, 2H), 3.09 (t, J=8.1 Hz, 2H), 2.28-1.94 (m, 7H), 1.86-1.69 (m, 5H), 1.59 (p, J=6.1 Hz, 1H), 1.46-1.36 (m, 4H), 0.94 (t, J=7.3 Hz, 6H) ppm.

Preparation of cyclohexyl (3S,4aS,6S,8aR)-6-fluoro-6-[2-(1H-1,2,3,4-tetrazol-5-yl)ethyl]-decahydroisoquinoline-3-carboxylate (6)

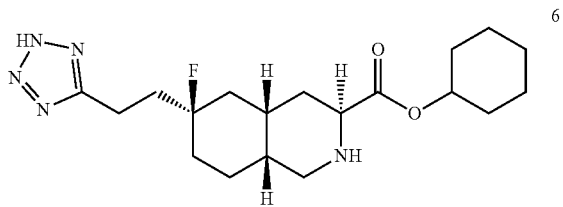 [SMILES: O=C(OC1CCCCC1)[C@@H]1C[C@H]2C[C@@](F)(CCc3nn[nH]n3)CC[C@H]2CN1]

Compound I-16 (100 mg, 0.2 mmol) was dissolved in THF (20 mL) and 10% Pd/C (100 mg) was added. This mixture was degassed by three hydrogen purge cycles (vacuum, release, and pressurization with hydrogen to 52 psi). The mixture was stirred under hydrogen overnight and then monitored by HPLC. The mixture was filtered through Celite®, washed with THF (20 mL), and the filtrate was concentrated under vacuum. The residue was dissolved in THF (20 mL) and fresh 10% Pd/C (100 mg) catalyst was added, followed by hydrogen purge cycles as before. The mixture was stirred under hydrogen overnight and monitored by HPLC. The mixture was filtered through Celite®, washed with THF (100 mL), and the filtrate was concentrated under vacuum. The crude product was purified via Gilson reverse phase chromatography (20% to 60% acetonitrile with 0.1% TFA-water with 0.1% TFA) to afford 6 as the TFA salt (17.0 mg, 2$^{nd}$ peak) and the C6-F-Isomer TFA Salt (21.7 mg, 1$^{st}$ peak). The desired isomer was further purified via Gilson reverse phase chromatography (10% to 98% acetonitrile-water) to provide pure compound 6 for testing. $^1$H NMR (299.96 MHz, CD$_3$OD) δ 4.89-4.94 (m, 1H), 4.01 (dd, J=12.9, 3.9 Hz, 1H), 3.17 (t, J=12.7 Hz, 1H), 3.06 (dd, J=13.0, 4.6 Hz, 1H), 2.98 (t, J=7.9 Hz, 2H), 2.33-2.42 (m, 1H), 1.97-2.15 (m, 5H), 1.83-1.96 (m, 3H), 1.64-1.82 (m, 5H), 1.25-1.62 (m, 8H) ppm. $^{19}$F NMR (282.22 MHz, CD$_3$OD) δ −160.20 (m, uncorrected, TFA reference −76.97) ppm. Mass Analysis (ES+)=380.19 [M+H] (Formula: C$_{19}$H$_{30}$FN$_5$O$_2$, Exact Mass: 379.24).

Preparation of octyl (3S,4aS,6S,8aR)-6-fluoro-6-[2-(1H-1,2,3,4-tetrazol-5-yl)ethyl]-decahydroisoquinoline-3-carboxylate (7)

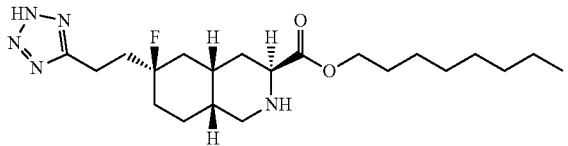

7

Compound I-17 (40 mg, 0.074 mmol) was dissolved in THF (10 mL) and 10% Pd/C (100 mg) was added. This mixture was degassed by three hydrogen purge cycles (vacuum, release, and pressurization with hydrogen to 52 psi). The mixture was stirred under hydrogen overnight and then monitored by HPLC. The mixture was filtered through Celite®, washed with THF (20 mL), and the filtrate was concentrated under vacuum. The residue was dissolved in THF (20 mL) and fresh 10% Pd/C (100 mg) catalyst was added, followed by hydrogen purge cycles as before. The mixture was stirred under hydrogen overnight and monitored by HPLC. The mixture was filtered through Celite®, washed with THF (100 mL), and the filtrate was concentrated under vacuum. The crude product was purified via Gilson (30% to 60% acetonitrile with 0.1% TFA-water with 0.1% TFA) to afford 7 as the TFA salt (2.9 mg, $2^{nd}$ peak) and the C6-F-Isomer TFA salt (4.5 mg, $1^{st}$ peak). $^1$H NMR (299.96 MHz, CD$_3$OD) δ 4.26 (dt, J=6.6, 1.8 Hz, 2H), 4.10 (dd, J=12.7, 4.0 Hz, 1H), 3.23 (d, J=13.2 Hz, 1H), 3.17-3.09 (m, 3H), 2.43-2.36 (m, 1H), 2.20-1.93 (m, 1H), 1.89-1.52 (m, 1H), 1.45-1.30 (m, 1H), 0.91 (t, J=6.9 Hz, 3H) ppm. Mass Analysis (ES+)=410.17 [M+H] (Formula: C$_{21}$H$_{36}$FN$_5$O$_2$, Exact Mass: 409.29).

Using the above protocols, additional ketone carbamate esters IV can be made and then reacted with the tetrazole Wittig VIII, fluorinated, and deprotected to generate novel fluorinated ester amine prodrugs (XI) as shown in Table 1.

TABLE 1

Fluorinated Ester Amine Prodrugs (XI).

| Compound No. | Structure |
|---|---|
| 3 | 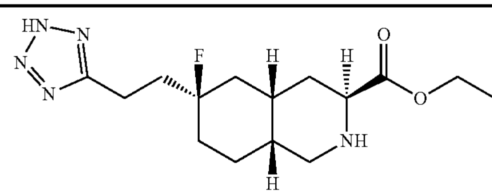 |
| 4 | 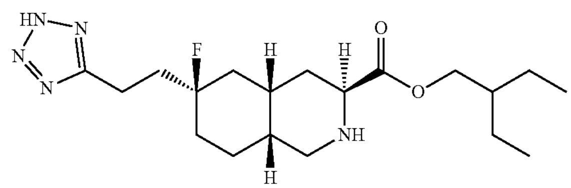 [SMILES: CCC(CC)COC(=O)[C@@H]1C[C@H]2C[C@@](F)(CCc3nn[nH]n3)CC[C@H]2CN1] |
| 5 | 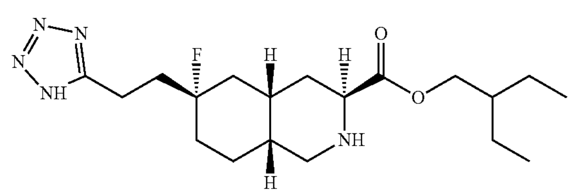 [SMILES: CCC(CC)COC(=O)[C@@H]1C[C@H]2C[C@](F)(CCc3nnn[nH]3)CC[C@H]2CN1] |
| 6 | 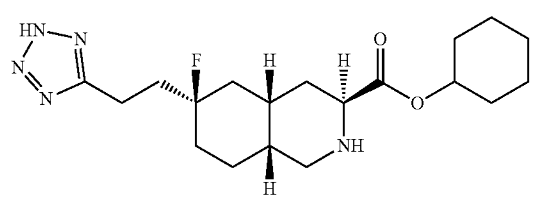 [SMILES: O=C(OC1CCCCC1)[C@@H]1C[C@H]2C[C@@](F)(CCc3nn[nH]n3)CC[C@H]2CN1] |
| 7 | 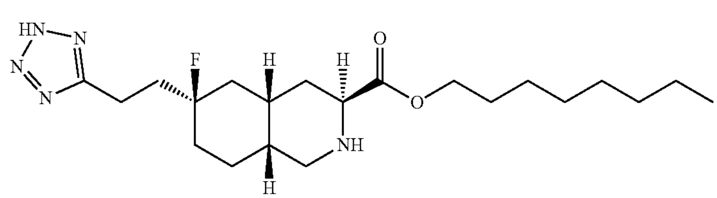 [SMILES: CCCCCCCCOC(=O)[C@@H]1C[C@H]2C[C@@](F)(CCc3nn[nH]n3)CC[C@H]2CN1] |

TABLE 1-continued
Fluorinated Ester Amine Prodrugs (XI).
| Compound No. | Structure |
|---|---|
| 8 | 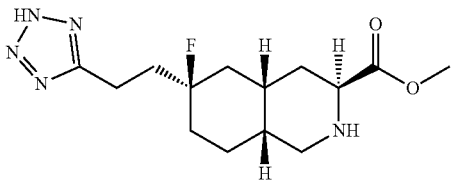 [SMILES: COC(=O)[C@@H]1C[C@H]2C[C@@](F)(CCc3nn[nH]n3)CC[C@H]2CN1] |
| 9 | 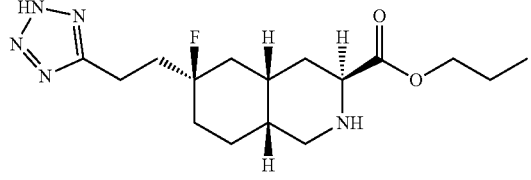 [SMILES: CCCOC(=O)[C@@H]1C[C@H]2C[C@@](F)(CCc3nn[nH]n3)CC[C@H]2CN1] |
| 10 | 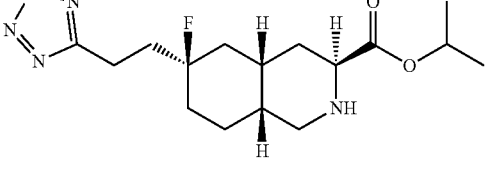 |
| 11 | 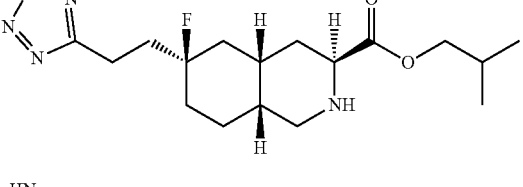 |
| 12 | 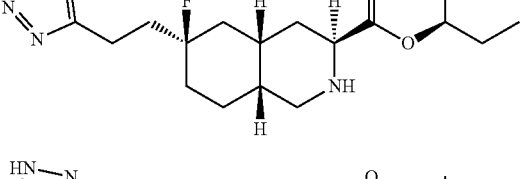 |
| 13 | 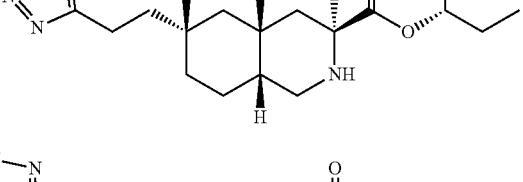 |
| 14 | 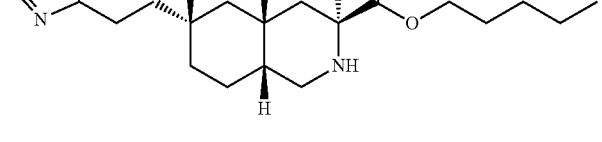 |
| 15 | 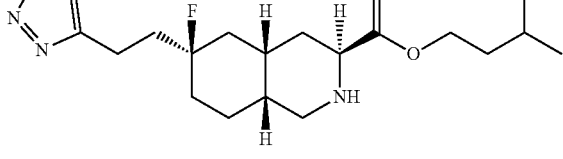 |

TABLE 1-continued

Fluorinated Ester Amine Prodrugs (XI).

| Compound No. | Structure |
|---|---|
| 16 | (structure: tetrazole-ethyl-decahydroisoquinoline with F, ester of pentan-3-ol) |
| 17 | (structure: tetrazole-ethyl-decahydroisoquinoline with F, cyclopentyl ester) |
| 18 | (structure: tetrazole-ethyl-decahydroisoquinoline with F, hexyl ester) |
| 19 | (structure: tetrazole-ethyl-decahydroisoquinoline with F, nonyl ester) |
| 20 | (structure: tetrazole-ethyl-decahydroisoquinoline with F, heptan-4-yl ester) |
| 21 | (structure: tetrazole-ethyl-decahydroisoquinoline with F, 2-ethylhexyl-type ester (2-propylpentyl)) |
| 22 | (structure: tetrazole-ethyl-decahydroisoquinoline with F, 2-butylhexyl ester) |
| 23 | (structure: tetrazole-ethyl-decahydroisoquinoline with F, cyclohexylmethyl ester) |

TABLE 1-continued

Fluorinated Ester Amine Prodrugs (XI).

| Compound No. | Structure |
|---|---|
| 24 | [Structure: decahydroisoquinoline with tetrazolylethyl and F substituents, benzyl ester] |
| 25 | [Structure: decahydroisoquinoline with tetrazolylethyl and F substituents, phenethyl ester] |
| 26 | [Structure: decahydroisoquinoline with tetrazolylethyl and F substituents, 4-phenylbutyl ester] |
| 27 | [Structure: decahydroisoquinoline with tetrazolylethyl and F substituents, decyl ester] |
| 28 | [Structure: decahydroisoquinoline with tetrazolylethyl and F substituents, dodecyl ester] |
| 29 | [Structure: decahydroisoquinoline with tetrazolylethyl and F substituents, tetradecyl ester] |
| 30 | [Structure: decahydroisoquinoline with tetrazolylethyl and F substituents, oleyl ester] |

TABLE 1-continued

Fluorinated Ester Amine Prodrugs (XI).

| Compound No. | Structure |
|---|---|
| 31 | 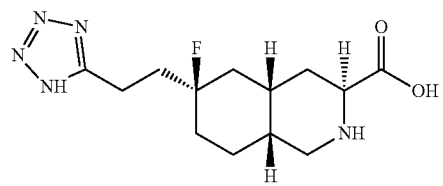 (structure for compound 31) |
| 32 | (structure for compound 32) |

Synthesis of Fluorinated Decahydroisoquinoline Amino Acids XII

Preparation of (3S,4aS,6S,8aR)-6-fluoro-6-[2-(1H-1,2,3,4-tetrazol-5-yl)ethyl]-decahydroisoquinoline-3-carboxylic acid (1)

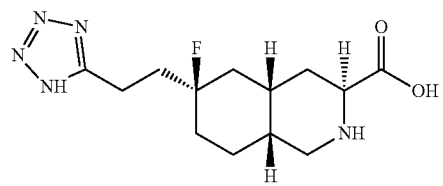

To a solution of compound 3 (1.29 g, 3.97 mmol) in water (2 mL) was added 2 N NaOH (9 mL, 16.9 mmol) at room temperature under nitrogen atmosphere. The solution was stirred at room temperature for 12 h and then quenched with 1N HCl (18.5 mL) to adjust pH between pH 2-3. The compound was purified by resin catch-and-release, Dowex 50WX8 200-400 mesh resin (Sigma-Aldrich, 1.7 eq/wet mL, 14 mL), which was washed with water until the pH was neutral in a coarse porosity sintered glass funnel. Resin (5 mL) was added to the compound solution and the mixture was stirred for 10 min at room temperature. Fresh resin (9 mL) was placed into a column with a coarse frit and the mixture was gently transferred onto the column (including all the resin). The top of the resin column was covered with cotton to prevent disturbing the layer. The solution was allowed to elute slowly and then the resin was wash with water (3×30 mL) to remove salts, 1:1 THF:water (3×30 mL) to remove organic impurities, water (2×30 mL), and then 6% ammonium hydroxide (300 mL) to release the desired compound. Fractions were collected and desired compound was detected using ninhydrin staining on reverse phase TLC plates (10% acetonitrile-water). Desired fractions were combined and concentrated under vacuum to afford crude product. The crude product was dissolved in water and lyophilized to afford 1 as a white solid (1.02 g, 86% yield). $^1$H NMR (299.96 MHz, D$_2$O) δ 3.58 (dd, J=12.9, 3.9 Hz, 1H), 3.11 (dd, J=19.2, 12.9 Hz, 1H), 3.08 (s, 1H), 2.97 (dd, J=8.8, 7.0 Hz, 2H), 2.35-2.28 (m, 1H), 2.14-1.61 (m, 9H), 1.56-1.47 (m, 1H), 1.38 (dtd, J=42.6, 14.6, 4.6 Hz, 1H) ppm. $^{19}$F NMR (282.22 MHz, D$_2$O) 6-157.59 (m, uncorrected) ppm. Mass Analysis (ES+)=298.12 [M+H] (Formula: C$_{13}$H$_{20}$FN$_5$O$_2$, Exact Mass: 297.16).

Preparation of (3S,4aS,6R,8aR)-6-fluoro-6-[2-(1H-1,2,3,4-tetrazol-5-yl)ethyl]-decahydroisoquinoline-3-carboxylic acid (2)

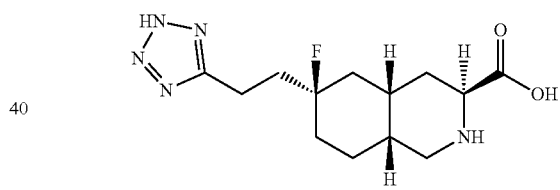

Using a similar protocol to make compound 1, the C6-F-isomer compound 5 was hydrolyzed with NaOH and purified by resin catch-and-release to afford 2. $^1$H NMR (299.96 MHz, D$_2$O) δ 3.75 (dd, J=10.6, 3.4 Hz, 1H), 3.29-3.14 (m, 2H), 2.96 (t, J=7.8 Hz, 2H), 2.22 (dt, J=7.8, 3.6 Hz, 1H), 2.13 (dt, J=7.8, 3.2 Hz, 1H), 2.10-1.86 (m, 3H), 1.84-1.61 (m, 5H) ppm. $^{19}$F NMR (282.22 MHz, D$_2$O) 6-167.27 (uncorrected, TFA reference −75.69) ppm. Mass Analysis (ES+)=298.26 [M+H] (Formula: C$_{13}$H$_{20}$FN$_5$O$_2$, Exact Mass: 297.16).

III. In Vitro Biology and In Vivo Pharmacology Materials, Methods and Experimental Data Section The present disclosure relates to chemical composition of matter (molecules) and characterizes biological and pharmacological activity of the molecules as AMPA receptor (AMPAR) antagonists or prodrugs of such molecules. The present disclosure also discloses uses for the treatment of pain, convulsions, seizures, epilepsy, and status epilepticus.

Additionally biological activity of compounds as antagonists of AMPA receptors or NMDA receptors (also called ionotropic glutamate-gated ion channels) were conducted using ex vivo functional electrophysiological assays of pyramidal neurons in slices of rat brain prefrontal cortex. Effects of test compounds cf. reference compounds were studied by whole cell patch-clamp electrophysiology recordings of s-AMPA-induced currents or NMDA-induced currents, respectively, using rat brain slice prefrontal cortex (layer V) pyramidal neurons.

Brain Slice Preparation Protocol.

Male Sprague Dawley rats were supplied by Charles River Laboratories (Wilmington, Mass. USA) and were housed 4 per cage within a temperature (20.5-23.5° C.) and humidity (30-80%) controlled environment on a 12 hour light/dark cycle with access to food (Teklad Global Soy Protein, Cat. No. T.2920X10, Envigo, Indianapolis, Ind., USA) and water ad libitum. At 4-6 weeks of age rats were terminally anaesthetized using isofluorane [(1-chloro-2,2,2-trifluoroethyl difluoromethyl ether) supplied by Baxter Healthcare Corp, Deerfield, Ill., USA], and decapitated. The brain was removed and 300 μm thick coronal prefrontal cortex (PFC) or sagittal hippocampal slices were sectioned using a Vibratome microtome. After brain removal, and throughout slicing, the tissue was submerged in ice cold aqueous cerebrospinal fluid (aCSF). Once slices were cut, they were transferred to a beaker containing aCSF and left at room temperature for a minimum of 1 hour before commencing electrophysiological recordings. After this period, individual slices were transferred to a recording chamber continuously perfused with aCSF at a rate of 4-6 mL/min before commencing experiment protocols. aCSF composition (in mM): NaCl, 127; KCl, 1.9; $KH_2PO_4$, 1.2; $CaCl_2$, 2.4; $MgCl_2$, 1.3; $NaHCO_3$, 26; D-glucose, 10; in water equilibrated with 95% Oxygen gas-5% $CO_2$ gas (reagent suppliers listed below). Experiments investigating NMDA currents had aCSF supplemented with 10 μM glycine (reagents suppliers listed below). All experiments were conducted following protocols with the approval of an Institutional Animal Care and Use Committee (IACUC).

Reagents for Electrophysiology Studies.

Fisher Scientific (Fairlawn, N.J., USA) supplied NaCl product #S271; KCl product #P330; CaCl2) product #C79; MgCl2 product #M33; D-glucose product #D16; HEPES product #BP310; sucrose product #S5, and $NaHCO_3$, product #S233. Millipore-Sigma (St. Louis, Mo., USA) supplied Mg-ATP product #A9187; CsCl product #$C_{3032}$; EGTA-Na product #E4378; GTP product #G8877; glycine product #G7126; KOH product #417661; and potassium D-gluconate product #G4500. EMD Chemicals (Gibbstown, N.J., USA) supplied KH2PO4 product #PX1565. Tocris and BioTechne (Bristol, United Kingdom and Minneapolis, Minn. USA) supplied (S)-alpha-amino-3-hydroxy-5-methyl-4-isoxazolepropionic acid, s-AMPA, product #0254; and supplied N-methyl-D-aspartic acid, NMDA, product #0114. Thermo Scientific (Rockford, Ill. USA) supplied DMSO product #20688.

Electrophysiological Recording of s-AMPA or NMDA Induced Currents in Pyramidal Neurons of Brain Slices from Prefrontal Cortex of Rats.

Whole cell patch-clamp recordings were performed from Layer V prefrontal cortex pyramidal neurons at room temperature using the 'visualized' version of the patch-clamp technique. Neurons were visualized using a BX51 upright microscope fitted with a 40×LUMPlanF1 water immersion objective (Olympus, Richmond Hill, Ontario, Canada). The microscope was connected to a C2400 CCD camera (Hamamatsu Bridgewater, N.J., USA) and images viewed on a VM 5516 B/W monitor (Sanyo, Moriguchi, Osaka Prefecture, Japan). Electrophysiological recordings were obtained using a Multiclamp 700B patch clamp amplifier (Molecular Devices, Sunnyvale, Calif., USA), with analogue signals digitized on a Digidata 1440a (Molecular Devices, Sunnyvale, Calif., USA). Patch pipettes were pulled using a P-87 Flaming/Brown micropipette puller (Sutter, Novato, Calif., USA), from GC150TF-10 thin-walled borosilicate glass (Harvard Apparatus, Saint-Laurent, Quebec, Canada) which had resistances of between 3 and 8 M2 when filled with intracellular solution.

Intracellular solutions used for PFC neuron recordings had the following composition (mM): potassium D-gluconate, 140; KCl, 10; EGTA-Na, 1; HEPES, 10; Mg-ATP, 4, 0.3 GTP; with pH and osmolarity compensated with potassium hydroxide and sucrose, respectively in all intracellular solutions (reagent suppliers listed above).

All test compound experiments were carried out in the voltage-clamp recording configuration of the whole cell patch-clamp technique and all recordings performed at a holding potential of −60 mV. Recordings were monitored on a Dell personal computer (PC) running Axon pClamp software (Molecular Devices, Sunnyvale, Calif., USA) and digitized at 10 kHz.

AMPA Receptor Biological Activity Assay of Compounds in Brain Slice Neurons.

Compounds were tested in whole-cell patch clamp electrophysiology experiments to measure antagonist effect on s-AMPA induced currents. These experiments examined the effects of a single concentration of each test-compound on 20 μM s-AMPA evoked currents in layer V rat brain slice prefrontal cortex pyramidal neurons. Both 1 μM and 10 μM concentrations of Compound 1 were tested and a 1 μM concentration of Compound 2 was tested, respectively in different experiments to the brain slice by bath perfusion from 50 mL syringes arranged in series with the main perfusion line from the aCSF reservoir. 20 μM s-AMPA was pressure-ejected for 100-1000 ms every 1-2 minutes using a NPI PDES-02DX (npi Electronic GmbH, Tamm, Germany) pneumatic picopump connected directly to a microelectrode placed within 200 μm of the recorded neuron. Each protocol was repeated three times. If the peak current was reduced by more than 70% upon first application of a test compound at 10 PM, then a single experiment was conducted at this 10 μM compound concentration. In that case the single 10 μM test of the compound was followed by testing the compound at 1 μM concentration three times.

NMDA Receptor Biological Activity Assay of Compounds in Brain Slice Neurons.

Compounds are tested in whole-cell patch clamp electrophysiology experiments to measure antagonist effect on NMDA induced currents. NMDA induced currents Experiments examined the effects of a single concentration of each test-compound on 50 μM NMDA-evoked currents in layer V rat brain slice prefrontal cortex pyramidal neurons. A 30 μM concentration of Compound 1 was administered to the slice by bath perfusion from 50 mL syringes arranged in series with the main perfusion line from the aCSF reservoir. 50 μM NMDA was pressure-ejected for 100-1000 ms every 1-2 minutes using a NPI PDES-02DX (npi Electronic GmbH, Tamm, Germany) pneumatic picopump connected directly to a microelectrode placed within 200 μm of the recorded neuron. Compound 1 was tested at 30 μM concentration in three experiments. Test Compounds or Reference compounds or inducer s-AMPA or inducer NMDA formulation. Test compounds (Sea Pharmaceuticals LLC, Cambridge Mass. USA) were prepared as 10 mM or 30 mM stock solutions in 100% DMSO solvent (solvent supplier listed above). Inducers of currents, s-AMPA or NMDA, were made as a 20 µM or 50 µM stock solution respectively in aCSF. Test compound stock solutions were diluted in the appropriate external recording solution to the final indicated test concentrations immediately prior to use. All compounds were stored at −20° C. prior to use.

Reference Compound Tests.

Tezampanel was tested as a reference compound at 30 µM, 10 µM, 3 µM, 1 µM, 0.3 µM, and 0.1 µM concentrations in the s-AMPA electrophysiological assay. This compound showed concentration-dependent inhibition of peak amplitude responses of rat brain slice PFC pyramidal neurons to 20 µM s-AMPA ($IC_{50}$ concentration where 50% of signal is inhibited was observed at 481+/−84 nM in the s-AMPA induced currents in rat brain cortex pyramidal neurons, n=4 to 5 experiments per concentration).

Tezampanel was tested at 30 µM concentration in the NMDA electrophysiological assay. Tezampanel at this concentration shows partial inhibition (40%+/−2%, n=4 experiments) of peak amplitude responses of rat brain slice PFC pyramidal neurons to 50 µM NMDA induced currents in rat brain cortex pyramidal neurons.

Data and Statistical Analysis of Electrophysiology Experiments.

All data were sampled using pClamp Clampex acquisition software with all offline analysis carried out using Clampfit (MDS Analytical Technologies). Data compilation and figure construction was carried out using Excel (Microsoft). One-way repeated measures analysis of variance (ANOVA, Prism, Graphpad) with Dunnett's post hoc comparison was used for statistical analysis.

(0.9% NaCl), then 0.1 N or 1 N sodium hydroxide solution was added carefully to pH 9 to pH 9.5 and the samples were stirred and agitated with vortex and heating at approximately 40° C. until fully dissolved (up to 15 minutes). Then 0.1 N or 1 N hydrochloric acid solution was then added carefully to adjust the pH to pH 7.1 to pH 7.3. Alternatively 0.5% methylcellulose solution in water could be substituted for normal saline solution. Vehicle solution was prepared using this same protocol without compound present. Dosing mixtures were allowed to equilibrate to room temperature prior to administration. Dosing mixtures were prepared fresh on the day of testing and used in less than 3 hours. All dosing solutions or dosing suspensions were mixed thoroughly prior to administration.

Compound #1 was formulated in SPHA. Other carboxylic acid isomers and their salts may be similarly formulated. Levetiracetam (TCI America, Portland Oreg.) dosing solution was prepared in a 0.5% methylcellulose (MC) in water.

Compounds may be formulated in alternative vehicle formulations not limited to those presented above.

Animal Handling Protocols and Compound or Vehicle Administration in Rodent Seizure Models (in Mice or Rats).

Adult male Carworth Farms (CF-1) mice (25-35 g) or young male Sprague-Dawley (SD) rats (100-150 g) were obtained from Charles River Laboratories Inc (Wilmington Mass. USA). CF1 mice were typically used for the 6 Hz psychomotor seizure model (6 Hz model described in the section below) but could also be used for the Maximal electroshock seizure (MES) model if performed in mice (Maximal electroshock seizure model described in the sec-

TABLE 2

Summary of In Vitro Biology Data for Compound # 1 and Compound # 2.

Electrophysiological assays for antagonist activity. % inhibition +/− SEM of s-AMPA or NMDA induced currents in neurons (whole cell patch-clamp recordings in rat brain cortex slices)

| Compound No. | s-AMPA (Tested at 1 pM) | s-AMPA (Tested at 10 pM) | NMDA (Tested at 30 pM) |
|---|---|---|---|
| 1 | 55.6 ± 5.8 (n = 3) | >90 (n = 1) | 61.0 ± 6.3 (n = 3) |
| 2 | 21.4 ± 2.1 (n = 3) | NT | NT |

NT = not tested.
SEM = Standard Error of the mean.
n = number of experiments

In Vivo Pharmacology of Compounds after Treatment of Rodents, Including In Vivo Rodent Epilepsy or Seizure Models and In Vivo Rodent Pain Model.

Compound Formulation and Preparation for Administration to Animals:

Dose suspensions or solutions of test compounds were formulated as specified in either of two formulations (i) DMSO in aqueous methylcellulose (referred to as DMC) or (ii) saline pH-adjusted (referred to as SPHA). For DMC formulation test Compounds 3, 4, or 6 were dissolved in DMSO and diluted into 0.5% methylcellulose (containing up to 3% DMSO final concentration). 0.5% methylcellulose (0.5% MC, Sigma, Catalog M-0430, St. Louis, Mo.) was prepared in water as per the manufacturer's instructions. DMC mixtures of compounds were homogenized by vortex agitation and stirred on a heated plate (~40° C.) until either the test compound mixtures was a homogenous suspension or was completely dissolved. SPHA formulation was used for some test articles that were higher aqueous soluble compounds or salts. For SPHA formulation compound powder was mixed directly into physiological (normal) saline tion below). SD rats were typically used for MES model but could also be used for 6 Hz psychomotor model if performed in rats. Animals were allowed free access to food and water, except during testing periods. After delivery from supplier lab to the in vivo pharmacology testing lab, animals were allowed sufficient time to acclimate to housing conditions prior to testing. Animals were housed in plastic cages in rooms with controlled humidity, ventilation, and lighting (12 hours lights on and 12 hours darkness). The animals were housed and fed in a manner consistent with the recommendations in the "Guide for Care and Use of Laboratory Animals" (National Research Council), and in accordance with guidelines set by an Institutional Animal Care and Use Committee (IACUC). Animal experiments were conducted in a manner consistent with Animal Research: Reporting of In Vivo Experiments (ARRIVE) guidelines (UK) and were approved by an IACUC. Test compounds or respective vehicle (placebo) were administered using an optimal fluid volume-to-body fluid ratio. Solutions or suspensions of test compounds, reference compounds or vehicles were administered to mice or rats in a volume of 0.01 mL/g body weight (mice) or 0.004 mL/g body weight (rats) by subcutaneous (s.c.) injection, intraperitoneal (i.p.) injection or by oral gavage (p.o.) unless otherwise indicated. Reference drug Levetiracetam or vehicle was administered by intraperitoneal (i.p.) injection.

Literature Description and In Vivo Pharmacological Validation of the Six Hertz (6 Hz) Psychomotor Seizure Model in Rodents.

Dr. James E. P. Toman first described the 6 Hz psychomotor seizure model in 1951. The 6 Hz psychomotor seizure model was extensively characterized and pharmacologically validated in mice using clinically used anti-epileptic drugs (AED's) by pharmacologist Louis S. Goodman in 1953 who showed certain clinically-used AED's were ineffective in the 6 Hz model in mice vs. the MES model in mice (described in another section below) and was found to resistant to treatment by certain AEDs such as phenytoin. The 6 Hz psychomotor seizure model in mice was little used for the next 50 years until revisited in 2001 by H. Steven White and Harold H. Wolf who pharmacologically compared several classes of AEDs. Toman J E 1951. Neurology 1:444-460. Brown W C et al. 1953. J Pharmacol Exp Ther 107:273-283. Barton M E et al. 2001. Epilepsy Res 47:217-227. Metcalf C S et al. 2017a. Epilepsia 58:484-493. Metcalf C S. 2017b. Epilepsia 58:1073-1084.

6 Hz Psychomotor Seizure Test of Compounds for Anti-Seizure Activity.

Mice are given a topical anesthetic on the cornea of each eye prior to placement of corneal electrodes. 6 Hz psychomotor seizures were induced in mice (usually 8 animals per group) using electrical stimulation via corneal electrodes (6 Hz, 0.2 millisecond rectangular pulse, 3 second duration at 22 mA using a Grass 48 stimulator instrument as described in Barton M E et al 2001. Epilepsy Res 47:217-227). Prior to placement of corneal electrodes for electrical stimulation 0.5% tetracaine in saline (Sigma) drops were applied to each eye. Seizures and behaviors that arise from the electrical stimulus in the 6 Hz model include a minor clonic seizure phase followed by stereotyped automatistic behaviors including stun, forelimb clonus, twitching of the vibrissae and Straub-tail. For a period of 1 minute after stimulation animals were observed for these behaviors by a pharmacologist. If any of these behaviors are observed the animal was considered to have demonstrated a seizure. Animals not presenting any of these behaviors were considered "protected" from seizures. This serves as a screen for in vivo pharmacological activity of test articles or reference anti-epilepsy drugs and defines anti-seizure activity as shown in several publications [Barton M E et al. 2001. Epilepsy Res. 47:217-227; Barton M E et al. 2003 Epilepsy Res. 56:17-26; Brown W C et al. 1953. J Pharmacol Exp Ther 107:273-283. Metcalf C S et al. 2017a. Epilepsia 58:484-493.; Metcalf C S et al. 2017c. Epilepsia 58:239-246.

Unless otherwise indicated pretreatment times of mice or rats were typically 0.5 hours for respective vehicle, Compounds 1, 3, 4, 6 or other compounds administered by subcutaneous or intraperitoneal route (unless other times indicated). A pretreatment time of 1 hour was used for Compounds 3, 4, 6 or other compounds administered by oral route unless other times indicated. Test compounds or respective vehicles were tested in some cases at other pretreatment times as indicated. A median effective dose ($ED_{50}$) and 95% confidence interval (CI) were calculated using a Prism (Graphpad software).

REFERENCES FOR RODENT 6 HZ PSYCHOMOTOR SEIZURE MODELS

Toman J E 1951. Neurology 1:444-460. "*Neuropharmacologic considerations in psychic seizures.*"

Brown W C, Schiffman D O, Swinyard E A, Goodman L S. 1953. J Pharmacol Exp Ther 107:273-283. "*Comparative Assay of an Antiepileptic Drugs by Psychomotor Seizure Test and Minimal Electroshock Threshold Test.*"

Barton M E, Klein B D, Wolf H H, White H S. 2001. Epilepsy Res 47:217-227. "*Pharmacological characterization of the 6 Hz psychomotor seizure model of partial epilepsy.*"

Metcalf C S, Klein B D, Smith M D, Pruess T, Ceusters M, Lavreysen H, Pype S, Van Osselaer N, Twyman R, White H S. 2017a. Epilepsia 58:484-493. *Efficacy of mGlu2 positive allosteric modulators alone and in combination with levetiracetam in the mouse 6 Hz model of psychomotor seizures;*

Metcalf C S, West P J, Thomson K E, Edwards S F, Smith M D, White H S, Wilcox K S. 2017b. Epilepsia 58:1073-1084. "*Development and pharmacologic characterization of the rat 6 Hz model of partial seizures.*"

Metcalf C S, Klein B D, McDougle D R, Zhang L, Kaufmann D, Grzegorz Bulaj G, White H S. 2017c. Epilepsia 58:239-246. "*Preclinical Evaluation of Intravenous NAX 810-2, a Novel GalR2-preferring Analog, for Anticonvulsant Efficacy and Pharmacokinetics.*"

Literature Description of MES (Maximum Electroshock Seizure) Model for Testing Molecules for Anti-Convulsant, Anti-Seizure and Anti-Epileptic Activity in Rodents.

Pharmacologist Louis S. Goodman extensively characterized the MES model in vivo pharmacology in treatment studies of experimental anti-convulsant, anti-seizure, anti-epileptic agents compared to anti-epileptic drugs (AEDs) in the 1950s-1970s. Later work 1980s-2010s by H. Steve White and Harold H. Wolf further extended use of the MES seizure model for pharmacological characterization of anti-epileptic compounds.

MES model materials, methods, and validation of several clinically used anti-epileptic drugs are described in Swinyard E A, et al. 1952. J Pharmacol Exp Ther 106:319-330.

Goodman's methods for MES model used an electrical stimulus instrument and electrodes described in Woodbury L A, Davenport V D. 1952. Arch Int Pharmacodyn Ther 92:97-107. The MES animal model and this type of MES instrument have been extensively used for in vivo pharmacological characterization of efficacy of anti-convulsive agents and anti-epileptic drugs (AEDs) for the last several decades by the United States National Institute of Health in screening of compounds for anti-convulsant activity (first two references are Chapters in 2 books) White H S, et al. (1995). In Levy R H, Mattson R H, Meldrum B S (Eds) Book title: *Antiepileptic Drugs*. 4th edition. pp. 99-110; White H S, et al. (2002) In Levy R, Mattson R, Meldrum B, Perucca E (Eds) Book title: *Antiepileptic Drugs*. 5th edition., pp. 36-48; White H S et al. 1995. Italian Journal Neurological Sciences 16:73-77 White H S, et al. 1998. Advances in Neurol 76:29-39. (Review); White H S, et al. 2008. Epilepsia 49:1213-1220. (Methods: updated MES model description); Barton M E, Peters S C, Shannon H E. 2003 Epilepsy Res. 56:17-26 (detailed methods on mouse 6 Hz and mouse MES models);

REFERENCES FOR RODENT MAXIMAL ELECTROSHOCK SEIZURES (MES) MODEL IN RATS OR MICE

Swinyard E A, Brown W C, Goodman L S. 1952. J Pharmacol Exp Ther 106:319-330. "*Comparative assays of antiepileptic drugs in mice and rats*"

Woodbury L A, Davenport V D. 1952. Arch Int Pharmacodyn Ther 92:97-107. "*Design and use of a new electroshock seizure apparatus, and analysis of factors altering seizure threshold and pattern.*"

White H S, Woodhead J H, Franklin M R. Swinyard E A, Wolf H H. (1995) *General principles: experimental selection, quantification, and evaluation of antiepileptic drugs*. In Levy R H, Mattson R H, Meldrum B S (Eds) Book title: *Antiepileptic Drugs*. 4th edition. Raven, New York, pp. 99-110;

White H S, Woodhead J H, Wilcox K S, Stables J P, Kupferberg H J, Wolf H H. (2002) *Discovery and preclinical development of antiepileptic drugs*. In Levy R, Mattson R, Meldrum B, Perucca E (Eds) Book title: *Antiepileptic Drugs*. 5th edition. Lippincott Williams & Wilkins, Philadelphia, pp. 36-48;

White H S, Johnson M, Wolf H H, Kupferberg H J. 1995. Italian Journal Neurological Sciences 16:73-77. "*The early identification of anticonvulsant activity: role of the maximal electroshock and subcutaneous pentylenetetrazol seizure models.*" (Review);

White H S, Wolf H H, Woodhead J H, Kupferberg H J. 1998. Advances in Neurol 76:29-39. "*The national institutes of health anticonvulsant drug development program: screening for efficacy.*" (Review);

White H S, Franklin M R, Kupferberg H J, Schmutz M, Stables J P, Wolf H H. 2008. Epilepsia 49:1213-1220. "*The anticonvulsant profile of rufinamide (CGP 33101) in rodent seizure models.*"

Leander J D, Rathbun R C, Zimmerman D M. 1988. Brain Res. 454:368-732 "*Anticonvulsant effects of phencyclidine-like drugs: relation to N-methyl-D-aspartic acid antagonism*";

Leander J D. 1989. Epilepsy Res. 4: 28-33 "*Evaluation of dextromethorphan and carbetapentane as anti-convulsants and N-methyl-D-aspartic acid antagonists in mice*";

Yamaguchi S, Donevan S D, Rogawski M A. 1993. Epilepsy Res. 15:179-184 "*Anticonvulsant activity of AMPA/kainate antagonists: comparison of GYKI 52466 and NBOX in maximal electroshock and chemoconvulsant seizure models.*"

Barton M E, Peters S C, Shannon H E. 2003 Epilepsy Res. 56:17-26 "*Comparison of the effect of glutamate receptor modulators in the 6 Hz and maximal electroshock seizure models*"

Metcalf C S, West P J, Thomson K E, Edwards S F, Smith M D, White H S, Wilcox K S. 2017c. Epilepsia 58:1073-1084. "*Development and pharmacologic characterization of the rat 6 Hz model of partial seizures*".

Maximal Electroshock Seizure (MES) Model In Vivo Pharmacology Test of Compounds for Anti-Seizure Activity in Rats.

Male Sprague-Dawley rats (body weight 100 to 150 grams at time of testing) were supplied by Charles River Laboratories Wilmington Mass. USA (N 8-10 animals per group). Rats were administered test article (experimental compounds, or vehicle, or positive control reference anti-convulsant compounds) by intraperitoneal (i.p.), subcutaneous (s.c.), intravenous (i.v.) or by oral gavage (p.o.) route. Corneas of rats were anesthetized with 0.5% tetracaine in saline at time of dosing and again prior to corneal stimulus. Unless otherwise indicated the pretreatment time for Compound 1 was 30 minutes (pretreatment time for vehicles or other test compounds was 60 min or as indicated) prior to corneal application of stimulus via electrodes (electric stimulus alternating current 60 Hz, 150 mA for 0.2 seconds duration for rats). Note if mice were used the stimulus parameters would follow published procedures of alternating current 60 Hz, 50 mA for 0.2 seconds [Metcalf C S, et al. 2017c. Epilepsia 58:1073-1084; White H S et al. 1995. Italian Journal Neurological Sciences 16:73-77; Barton M E, et al. 2003 Epilepsy Res. 56:17-26 (contains detailed description of MES and 6 Hz models both in mice); Leander J D, Rathbun R C, Zimmerman D M. Brain Res. 1988, 454:68-72; Leander J D 1989 Epilepsy Res. 4:28-33; and Yamaguchi S, Donevan S D, Rogawski M A. 1993 Epilepsy Res. 15:179-184.]. If animals do not show hind limb extension, they are considered protected from the convulsant effect of electroshock. In some cases the effective dose ($ED_{50}$ and 95% confidence interval) of test compound or reference compound that abolished the tonic-extensor component of the convulsion in 50% of the animals is calculated from dose-response data [Litchfield, J T Jr, Wilcoxon. 1949. *J. Pharmacol. Exp. Ther.* 96:99-113 "*A simplified method of evaluating dose-effect experiments.*"]. One group of animals always receives vehicle treatment (negative control) and one group of animals always receives reference compound treatment (positive control) for each experiment.

AMPA Receptor Antagonist Activity of Compounds In Vivo.

In vivo activity of AMPA receptor antagonists compounds can be assayed using the Maximum electroshock seizure (MES) model in mice or in rats or the 6 Hz psychomotor seizure model in mice or rats. In vivo efficacy data for AMPA receptor antagonist tezampanel treatment has been shown in mouse MES model in Ornstein P L et al. 1993. J Med. Chem 36:2046-2048 and in both the mouse MES and mouse 6 Hz psychomotor seizure model in Barton M E et al. 2003. Epilepsy Res 56:17-26. In vivo efficacy data for treatment of mice with FDA approved anti-epileptic drug AMPA receptor antagonist (AMPARA) perampanel in both the 6 Hz seizure model and in the maximal electroshock seizure MES model in mice was presented by Hanada T et al. 2011. Epilepsia 52:1331-1340. In vivo efficacy data with experimental AMPA receptor antagonist (AMPARA) compound YM928 tested in MES mice model was shown in Yamashita H, et al. 2004. J Pharmacol Exp Ther 308:127-133. In vivo efficacy data comparing experimental therapeutic AMPARA compound YM928 vs its derivatives cf. a clinically studied AMPARA (talampanel) treatment of mice in the MES model was shown in Inami H, et al. 2019. Chem Pharm Bull (Tokyo) 67:699-706.

REFERENCES FOR AMPA RECEPTOR ANTAGONIST COMPOUND OR DRUG TREATMENT EFFICACY IN RAT OR MOUSE MES OR 6 HZ PSYCHOMOTOR SEIZURE MODELS

Ornstein P L, Arnold M B, Augenstein N K, Lodge D, Leander J D, Schoepp D D. 1993. J Med. Chem 36:2046-2048. "(3SR,4aRS,6RS,8aRS)-6-[2-(1H-tetrazol-5-yl) ethyl]decahydroisoquinoline-3-carboxylic acid: a structurally novel, systemically active, competitive AMPA receptor antagonist" (tezampanel);

Barton M E, Peters S C, Shannon H E. 2003. Epilepsy Res 56:17-26. "*Comparison of the effect of glutamate receptor modulators in the 6 Hz and maximal electroshock seizure models*" (tezampanel);

Hanada T, Hashizume Y, Tokuhara N, Takenaka O, Kohmura N, Ogasawara A, Hatakeyama S, Ohgoh M, Ueno M, Nishizawa Y. 2011. Epilepsia 52:1331-1340. "*Perampanel: A Novel, Orally Active, Noncompetitive AMPA-receptor Antagonist That Reduces Seizure Activity in*

Rodent Models of Epilepsy" (FDA approved anti-epileptic drug AMPA receptor antagonist perampanel in 6 Hz seizure or MES models in mice);

Yamashita H, Ohno K, Amada Y, Hattori H, Ozawa-Funatsu Y, Toya T, Inami H, Shishikura J-I, Sakamoto S, Okada M, Yamaguchi T. 2004. J Pharmacol Exp Ther 308:127-133. "*Effects of 2-[N-(4-chlorophenyl)-N-methylamino]-4H-pyrido[3.2-e]-1,3-thiazin-4-one (YM928), an orally active alpha-amino-3-hydroxy-5-methyl-4-isoxazolepropionic acid receptor antagonist, in models of generalized epileptic seizure in mice and rats*" (experimental AMPA receptor antagonist (AMPARA) compound YM928 tested in MES mice model);

Inami H, Shishikura J-I, Yasunaga T, Hirano M, Kimura T, Yamashita H, Ohno K, Sakamoto S. 2019. Chem Pharm Bull (Tokyo) 67:699-706. "*Synthesis and pharmacological evaluation of 3-[(4-oxo-4H-pyrido[3,2-e][1,3]thiazin-2-yl)(phenyl)amino]propanenitrile derivatives as orally active AMPA receptor antagonists*". (in vivo efficacy data comparing experimental therapeutic AMPARA compound YM928 vs its derivatives cf. a clinically studied AMPARA (talampanel) in the MES model in mice).

Rotarod Test for Motor Impairment.

Testing mouse performance on the rotarod was conducted in tandem with 6 Hz psychomotor seizure model stimulation to verify whether doses administered produced substantial motor impairment. Evaluation in the rotarod assay was conducted immediately prior to 6 Hz psychomotor seizure model testing. Therefore, each treatment group was subjected to evaluation in the rotarod assay followed immediately by testing in the 6 Hz psychomotor seizure model. When mice are placed on a 1-inch knurled rod rotating at a speed of 6 rpm, the animals can maintain equilibrium for long periods. Motor impairment was assessed by determining whether mice remained on the rotarod during a 1-minute observation period; that is, three falls during a 1 minute period was considered a rotarod failure.

Rat behavior pharmacology observations for signs of motor impairment by trained observer. Rats were monitored after dosing for any signs of impairment by Compound 1 administered as 6 mg/kg dose by subcutaneous route. No tolerability or neurological changes were observed all rats were alert, upright and behaved normally for the 30 minute observation period following administration.

Statistical Analysis.

Seizure protection and rotarod motor impairment data are presented as # (the number of animals protected from seizure)/N (the treatment group size consisting of the number of animals tested by treatment with vehicle or compound at a given dose) and # with motor impairment/N tested, respectively. A Fisher exact test was used to compare motor impairment values for specific treatment groups with VEH-treated animals. For dose-response analyses the dose resulting in 50% efficacy $ED_{50}$ (and 95% CI) values were calculated using Prism (Graphpad Software) analysis wherein at least three treatment groups (N=6 to 10 animals per group) were used in the calculation. Plasma levels are presented as means standard error and were compared using a Student's t-test.

Table 3 shows the results of tests of Compound 1 in vivo seizure protection studies in the Maximal Electroshock Seizure (MES) model test in rats after single acute systemic administration. Compound 1 treatment or Vehicle treatment were each well tolerated by rats.

TABLE 3

Results of Compound 1 Treatment in the Maximal Electroshock Seizure (MES) Model in Rats.

| Test Article Treatment | Dose (mg/kg) | Treatment Time* (hours) | Route | Formulation | MES Test Results (# rats protected from seizure/# rats tested) |
|---|---|---|---|---|---|
| Compound 1 | 6 | 0.5 | S.C. | SPHA | 6/6 |
| Vehicle DMC | — | 1 | P.O. | DMC | 1/8 |

*Prior to corneal stimulus.

Table 4 shows the results of tests of Compounds 1, 3, 4, and 6 in vivo seizure protection studies in the 6 Hz Psychomotor seizure model test in mice after single acute systemic administration.

TABLE 4

Results of Compounds 1, 3, 4, and 6 Treatment in the 6 Hz Psychomotor Seizure Model in Mice.

| Test article Treatment | Dose (mg/kg) | Treatment Time* (hours) | Route | Formulation | 6 Hz Test Results (# mice protected from seizure/# mice tested) |
|---|---|---|---|---|---|
| Compound 1 | 10 | 0.5 | s.c. | SPHA | 8/8 |
| Compound 1 | 6 | 0.5 | s.c. | SPHA | 7/8 |
| Compound 1 | 3 | 0.5 | s.c. | SPHA | 5/8 |
| Compound 1 | 1 | 0.5 | s.c. | SPHA | 3/8 |
| Compound 1 | 0.6 | 0.5 | s.c. | SPHA | 3/8 |
| Compound 1 | 0.3 | 0.5 | s.c. | SPHA | 1/8 |
| Vehicle SPHA | — | 1 | s.c. | SPHA | 0/8 |
| Compound 3 | 13 | 0.5 | s.c. | DMC | 8/8 |
| Compound 4 | 13 | 0.5 | s.c. | DMC | 8/8 |
| Compound 3 | 13 | 1 | p.o. | DMC | 5/8 |
| Compound 4 | 13 | 1 | p.o. | DMC | 6/7 |
| Compound 6 | 13 | 1 | p.o. | DMC | 8/8 |
| Vehicle DMC | — | 1 | p.o. | DMC | 1/8 |

*Compound treatment at doses shown or Vehicle treatment 30 minutes by the subcutaneous route or 60 minutes by the oral route, prior to corneal stimulus.

Subcutaneous Pentylenetetrazole (scPTZ) seizure model in rodents.

The scPTZ model can be performed using mice or rats. The materials, methods and protocol is described in White H S, Johnson M, Wolf H H, Kupferberg H J. 1995. Italian Journal Neurological Sciences 16:73-77. "*The early identification of anticonvulsant activity: role of the maximal electroshock and subcutaneous pentylenetetrazol seizure models*" (review) and see reviews (2 Chapters in 2 books) White H S, Woodhead J H, Franklin M R. Swinyard E A, Wolf H H. (1995) *General principles: experimental selection, quantification, and evaluation of antiepileptic drugs*. In Levy R H, Mattson R H, Meldrum B S (Eds) Book title: *Antiepileptic Drugs*. 4th edition. Raven, New York, pp. 99-110; and White H S, Woodhead J H, Wilcox K S, Stables J P, Kupferberg H J, Wolf H H. (2002) *Discovery and preclinical development of antiepileptic drugs*. In Levy R, Mattson R, Meldrum B, Perucca E (Eds) Book title: *Antiepileptic Drugs*. 5th edition. Lippincott Williams & Wilkins, Philadelphia, pp. 36-48.

Lithium-Pilocarpine Induced Status Epilepticus Rat Model.

Either Long-Evans or Sprague-Dawley rats can be used following published procedures to induce status epilepticus in animals (see Metcalf C S, Radwanski P B, Bealer S L. "Status epilepticus produces chronic alterations in cardiac sympathovagal balance." *Epilepsia*. 2009, 50 (4), 747-54; Clifford, D. B., Olney, J. W., Maniotis, A., Collins, R. C., Zorumski, C. F. "The functional anatomy and pathology of lithium-pilocarpine and high-dose pilocarpine seizures." *Neuroscience*, 1987, 23, 953-968; Hanada T, Ido K, Kosasa T. "Effect of perampanel, a novel AMPA antagonist, on benzodiazepine-resistant status epilepticus in a lithium-pilocarpine rat model." *Pharmacol. Res. Perspect.* 2014, 2 (5), e00063; Wu T, Ido K, Osada Y, Kotani S, Tamaoka A, Hanada T "The neuroprotective effect of perampanel in lithium-pilocarpine rat seizure model." *Epilepsy Res.* 2017, 137, 152-158). The effect of test compounds vs respective vehicle is compared to reference compounds perampanel or other reference compounds.

Rodent Pain Model.

The formalin pain test is based on the modifications of the original model descriptions (Malmberg A B, Yaksh T L. "Antinociceptive actions of spinal nonsteroidal anti-inflammatory agents on the formalin test in the rat." *J. Pharmacol Exp. Ther.* 1992, 263 (1), 136-46 and Wheeler-Aceto H, Porreca F, Cowan A. "The rat paw formalin test: comparison of noxious agents." *Pain.* 1990, 40 (2), 229-38). Briefly, slight modifications can be made to the above methods: young Sprague-Dawley rats are used (as described below) and formalin (Sigma) is prepared fresh in sterile saline each day.

Young adult male Sprague-Dawley rats (60-70 g body weight) can be obtained from Charles River Laboratories (Wilmington Mass., USA). Animals are allowed free access to food and water, except during testing periods. After delivery, animals are allowed sufficient time to acclimate to housing conditions prior to testing (~1 week) and are housed in plastic cages in rooms with controlled humidity, ventilation, and lighting (12 hours on-12 hours off). The animals are housed and fed in a manner consistent with the recommendations in the "Guide for Care and Use of Laboratory Animals" (National Research Council), and in accordance with guidelines set by an Institutional Animal Care and Use Committee (IACUC). Animal experiments are conducted in a manner consistent with ARRIVE guidelines (United Kingdom). Protocols are pre-approved by the IACUC prior to testing.

Test compounds can be administered using an optimal fluid volume to body fluid ratio. Test compounds can be administered in a volume of 0.04 mL/10 g body weight in rats. Test compounds can be formulated as described above in the 6 Hz seizure model section in either formulation described. Morphine Sulfate can be purchased from Sigma and prepared by formulation in Saline. Morphine is usually administered by subcutaneous (s.c.) route. Test articles or Vehicle can be administered by s.c. route of administration unless indicated. Other routes of administration (e.g., i.p., s.c., p.o., i.m. etc. may be used) and method of compound administration, including vehicle solution and solvent formulations may be used.

Formalin Pain Model in Rats. The Formalin Pain Model can be performed as follows. Test compounds are administered to animals either 0.5 or 1 hour prior to the injection (50 µL; 30 gauge needle) of a solution of 5% formalin [prepared by mixing Formalin (Sigma, St. Louis Mo.) into sterile saline] sub-dermally into the plantar region of the right hind-paw of rats. The formalin test is a well-established model for evaluation of analgesic effects of various compounds in mice and rats. Formalin elicits a distinct biphasic behavioral profile characterized by licking of the affected paw initially (Phase I: 0-10 min following formalin administration), then after a brief reduction in paw licking behavior, the behavior resumes (Phase II: 20-45 min following formalin administration). Following the injection of formalin, each animal is observed for alternating first 2 min of 5 min epochs until 45 min have elapsed. The cumulative length of licking for each 2 minute time period is measured. Area under the curve (AUC) values for both Phase I and Phase II are normalized to vehicle (VEH)-treated rats.

in vivo pharmacological methods—patent Sea Pharmaceuticals, LLC in Sprague-Dawley male rats (Charles River Laboratories) were used for the 3 different studies of test compounds:

Study I. PK (pharmacokinetics) of acute dose in vivo in rats.

Study II. SAD (single ascending dose) 1-day determination of maximum tolerated dose and bioanalytical determination of dose-exposure relationship in vivo in rats.

Study III. MAD (multiple ascending dose) repeated once-daily administration for 5-days determination of maximum tolerated dose and bioanalytical determination of dose-exposure relationship in vivo in rats.

The Sprague Dawley male rats used in the studies were supplied by Charles River Laboratories (Wilmington, Mass., USA). The animals were housed for a 7-day acclimation period at a veterinarian-certified animal care facility in the United States. Upon arrival, the rats weighed between 225-250 grams. The rats were 7-8 weeks of age with an average weight of 260-280 grams at the time of the PK study. Rats were housed 2 per cage in a ventilated HEPA filtered, cage rack system. The rats were kept on a 12:12 hour normal light cycle (12 hours darkness, 12 hours light with lights on at 7:00 AM local time). Rats were allowed standard rodent chow and water ad libitum for both studies. Rats were not fasted during the study. Animals were handled prior to the study and assigned randomly by body weight to treatment groups. The holding room and procedure room temperature was 21-24 degrees C. and humidity was at 40-42% during the experiments (within the normal range of the care facility). All procedures were completed according to IACUC (Institutional Animal Care and Use Committee) approved protocols for housing and study of administered test articles.

Administration of test articles (each respective compound formulated in excipients).

Intravenous (IV) route of administration. To perform IV dosing, each rat was restrained in a decapicone (plastic bag with open end for breathing) clipped on either side of the tail to the table surface with the tail freely accessible. A needle (23 G×1 in. BD Precision Glide catalog #BD305145, manufacturer BD Biosciences, New Jersey USA) attached to a 1 mL (catalog #BD 301025, manufacturer BD Biosciences, New Jersey USA) syringe was inserted into the lateral vein of the tail. Proper placement was ensured by drawing back on syringe until a flash of blood was perceived. Once confirmed, the required volume was administered.

Oral gavage per os (PO) route of administration. To perform the PO dosing, each rat was restrained by the scruff of the neck and the head and upper body immobilized to prevent struggling and injury. Once in a stable vertical position, the rat was then dosed by inserting the feeding tube (18 G Instech FTP-18-38, manufacturer Plymouth Meeting, Pennsylvania, USA) attached to a 1 mL (BD 301025, manufacturer BD Biosciences, New Jersey USA) or 3 mL syringe (BD309588, manufacturer BD Biosciences, New Jersey USA) according to required dose volume into the esophagus of the rat. Once in proper position, the volume was dispensed into the stomach of the rat.

Subcutaneous route of administration. To perform the SC dosing, each rat was restrained by the scruff of the neck and the head and upper body immobilized to allow for 'tenting' of the skin. Once in a stable position a needle (21 G×0.5 in BD Precision Glide BD 305111, manufacturer BD Biosciences, New Jersey USA) attached to a 1 mL (BD 301025, manufacturer BD Biosciences, New Jersey USA) syringe was inserted under the fur of the animal between the shoulder blades into the tented area. The volume was then dispensed under the fur of the rat.

Blood was collected via tail bleed (0.0833, 0.25, 0.5, 1, 2, 4 hr for IV) and (0.5, 1, 1.167, 1.5, 2, 4, 6 hr for PO), and (0.25, 0.5, 1, 2, 4, 6 hr for SC). Terminal blood collection was done via cardiac puncture at 4 hr post-dose (IV) and 6 hr post-dose (PO and SC). Terminal blood was done via cardiac puncture at 70 mins for rats undergoing Irwin test (for certain PO and SC groups as indicated). Terminal blood was done via cardiac puncture at 30 mins for rats for a certain SC group as indicated.

Irwin Test Procedure

Rats were subjected to the Irwin Test Procedure of in vivo assessment of test compounds effects on neurological functions in rodents which was modified for rats. Rats were acclimated to the procedure room for at least 30 minutes. Rats were assessed for the features described below. Each rat was scored on a 0 to 3 scale with 0 representing the response in a normal animal and 3 representing a maximally impaired animal. Note that it is normal for an animal to score within the 0 to 1 range during Irwin testing. Animals were tested 55-60 min after test compound administration. Reference: Irwin, S. 20 Sep. 1968; "*Comprehensive observational assessment: la. A symptomatic quantitative procedure for assessing the behavioral and physiologic state of the mouse*" Psychopharmacologia 13(3): 222-257.

Irwin Parameters—Scoring
1. General Appearance—outward appearance
a. Grooming, coat color, whiskers etc. Comment.
b. Scored 0 to 3.
  i. 0: normal—coat is sleek, shiny; eyes wide open; no wounds
  ii. 1: slightly scruffy coat, slight eye closure
  iii. 2: medium scruffy coat; eye discharge/eye closure/skin lesions
  iv. 3: scruffy coat; bloody nails
2. Hyperactivity
a. In cage observation
b. Scored between 0-3 with Absent=0; present=3
  i. 0: normal activity; not hyperactive
  ii. 1: a touch or stimulus elicits a more than normal response
  iii. 2: interrupted grooming, running around cage more than normal exploration
  iv. 3: actively running around; jumping out of cage; not attempting to groom
3. Hypoactivity
a. In cage observation
b. Scored between 0-3 with Absent=0; present=3
  i. 0: normal activity, not hypoactive
  ii. 1: delayed in normal movement, more stationary; stopping without grooming
  iii. 2: little movement to stimulus, more stationary than mobile
  iv. 3: no movement, no response to stimulus, stationary
4. Sedation
a. In cage observation
b. Scored between 0-3 with Absent=0; present=3
  i. 0: normal—no sedation
  ii. 1: unsteady gait, wobbly
  iii. 2: partially closed eyes
  iv. 3: fully sedated; eyes closed
5. Seizures
a. Scored between 0-3 with Absent=0; present=3
  i. 0: no seizures
  ii. 1: tremors (shuddering)
  iii. 2: HIC—handling induced convulsions
  iv. 3: full seizure—running-bouncing clonus or tonic hindlimb
6. Suspended body placement
a. Suspend animal by its tail. Animal should struggle and/or extend all 4 limbs.
b. Scored between 0-3 with Absent=3; present=0
  i. 0: presence of struggle and extends all four limbs
  ii. 1: extension of some limbs with light struggle
  iii. 2: initial struggle, then nothing
  iv. 3: absence of any struggle or limb movement
7. Crossed extensor reflex
a. When foot of one of the hind limbs is pinched the opposite hind limb extends
b. Scored 0 or 3 with Absent=3; present=0
8. Forelimb/hind limb placing response
a. Contact to back of each paw in turn by a thin rod results in a raising and placing of the foot on the surface of the object if the animal is suspended in the air and no other paw is touching a solid surface
b. Score 0 or 3 with Absent=3; present=0
9. Grasp reflex
a. The animal will grasp an instrument when the paw is stroked
b. Scored 0 or 3 with Absent=3; present=0
  i. 0: immediate grasps instrument
  ii. 3: no response to paw touch
10. Bar holding
a. Place bar holding rod to animal's front paws and allow it to support its own weight
b. Scored 0 or 3 with Absent=3; present=0
  i. 0: animal supports weight
  ii. 3: animal will not hold bar after released/does not stay on bar
11. Righting reflex test
a. Place animal on its back and judge the to turn over onto its belly (normal position)
b. Scored between 0-3 with Absent=3; present=0
  i. 0: flips immediately, cannot get to flip onto back
  ii. 1: on back, flips over quickly
  iii. 2: on back, turns over slowly, or struggle to right
  iv. 3: not trying to right themselves
12. Tail pinch response
a. Animal will respond to tail pinch by flinching, by pinching ~1 cm from base of tail.
b. Scored 0 or 3 with Absent=3; present=0
  i. 0: present, normal flick or escape response
  ii. 3: absent, no movement or escape
13. Auditory startle
a. A response should be observed after a auditory startle is initiated after using a dog clicker (noise-making device).
b. Scored 0 or 3 with Absent=3; present=0: presence of startle, ears flicker.
  i. 0: present, normal startle or ear flicker
  ii. 3: absent, no startle response OFA. Open Field Activity Measurement of Spontaneous Locomotor Activity of Live Rats.

Animals were acclimated to the procedure room for at least 30 minutes prior to testing.

All animals were dosed and at the specified time post-dose (immediately after Irwin testing) placed into the open field chamber for a 15 minute period of recording time (from 60 to 75 minutes after administration of test article treatments (compounds formulated in excipients or vehicle) or untreated controls. All open field experiments were conducted in an "open field arena" open roof box made of clear plexiglass dimensions 43×43×30 cm (length×width×height interior chamber dimensions) catalog number ENV-515 Open Field Apparatus; manufacturer Med Associates Inc, city and state: Fairfax, Vermont, USA. Each ENV-515 consists of 16×16 infrared photo beams with a space of 2 cm between beams to record movement in all 3 dimensions (x, y, z planes). Movement was recorded using the Activity Monitor™ program designed by Med Associates to determine the endpoints stereotypical movement counts and ambulatory movement counts (Activity Monitor 7 Software developed by Med Associates Inc, manufacturer city and state: Fairfax, Vermont, USA). Distance travelled and vertical activity were recorded (Activity Monitor 7 Software developed by Med Associates Inc, manufacturer city and state: Fairfax, Vermont, USA). Reference: Open Field Activity of rodents and effects of drugs or test article treatments: Fox K M, Sterling R C, Van Bockstaele E J (2009), "*Cannabinoids and novelty investigation: influence of age and duration of exposure*". Behavioral Brain Research 196:248-253.

Plasma and Tissue Collection.

Blood was collected in K2EDTA tubes (BD microtainer, BD Biosciences, New Jersey USA) and plasma collected by spinning blood in a refrigerated centrifuge. Plasma was transferred to a clean microcentrifuge tube, frozen on dry ice, stored at −80 C until bioanalysis. A minimum of 50 microliters of plasma was collected. Whole brain was dissected at the proper termination time point, weighed, and flash frozen on dry ice. Cerebral Spinal Fluid (CSF) was collected at the designated termination time point. CSF samples and brains were stored at −80 degrees C.

Blood Collection Procedures (for Plasma).

Tail Bleed Blood Collection Procedure. With the rat in the home cage, tails were carefully snipped (cut with a scissors) about 1 cm from the tip. Using a BD microtainer, blood was carefully collected in a K2EDTA tube. After the tube is withdrawn, mild pressure should be applied with cotton or a gauze sponge to stop the bleeding.

Cardiac Puncture—Cardiac Blood Collection Procedure. Rats were anesthetized by placement in a chamber with CO2. The rat was in a euthanasia plane of anesthesia (fully anesthetized). The animal was laid on its back and rub alcohol over the sternum. A needle was placed under the skin just left (animal's left) of the sternum. A 10 mL needle (23 G 1" BD305145, manufacturer BD Biosciences, New Jersey USA)) 5 mm from the center of the thorax towards the animal's chin, 5-10 mm deep, holding the syringe 25-30 degrees away from the chest. The plunger was pulled slightly to create slight negative pressure in the syringe. The needle was advanced to the midpoint of the chest cavity. Once the needle reached the heart, blood flowed into the syringe to collect sample. The cardiac needle was held steady and plunger was gently pulled back to collect blood sample. Rats were euthanized by placing it back in the CO2 chamber.

Cerebral Spinal Fluid (CSF) Collection Procedure.

Animals were placed in a euthanasia chamber with carbon dioxide to euthanize. Rats were removed from chamber and positioned in sternal recumbency on a procedure area. The skin from the upper portion of the neck was cut with scissors, extending midline to expose the cranial region of skull. The head was positioned using a thumb and finger of one hand so the head is flexed downward at approximately 45°. CSF was collected by direct needle puncture into the cisterna magna, using the occipital bone and the wings of the atlas as landmarks.

Suction on the syringe was released with butterfly needle (EXEL INT 21 G×¾" Thin Wall catalog number #277-04, manufacturer EXEL INT, Redondo Beach, California, USA). The needle was held (bevel up) carefully in the opposite hand, the midline was carefully followed beyond the occipital crest, and the needle was gently "walked" or "slid" back towards the cisterna magna (bony part) until the operator could feel the needle enter the spinal cavity. Once correct placement was established, a small amount of negative pressure was applied to the syringe: CSF then flowed into the needle hub (note if there was no flow of CSF, then the needle was repositioned and procedure repeated). Negative pressure was applied with one hand until CSF flowed; the procedure was conducted slowly to avoid blood contamination of the sample. A white paper was used as a background to monitor for color change in the sample just above the needle during collection (note: upon observation of color change, pressure on syringe was ceased or clamp butterfly just above color change). To complete CSF sample collection: the needle was removed from the syringe. The CSF sample was transferred to a micro-centrifuge tube from the syringe (note: if blood traveled into centrifuge tube it was placed in a clinical micro-centrifuge and centrifuged 13,000 RPM for 1 minute. CSF supernatant layer was collected avoiding the blood at bottom of tube. CSF was then flash frozen on dry ice and stored at −80 degrees C. until bioanalysis.

Brain Collection Procedure.

After CSF collection the skull was dissected by rapidly cutting using a scissors. The brain was gently lifted out using a forceps and immediately flash frozen on dry ice then stored −80 degrees C. until bioanalysis.

Dose Sample (DS) Collection Procedure.

Dose solutions or Dose suspensions of compound 1 or compound 2 in excipients were collected after administration each day to animals. The Dose samples were flash frozen at −80 degrees C. until bioanalysis.

Quantitative LCMS bioanalysis of Compound 1 or Compound 2.

Measurement of Compound 1 or Compound 2 from rat samples (plasma, cerebral spinal fluid "CSF" or brain homogenate) was done by high resolution using a sensitive LCMS method.

Extracts of biological samples (either organic solvent precipitated or organic solvent extracted i. plasma or ii. CSF or iii. homogenates of whole brains from Compound 1 or Compound 2 treated rats) were subjected to LCMS and were compared to freshly prepared standard curves on exactly the same LCMS instrument. The standard curves were prepared of Compound 1 or Compound 2 at known concentrations dispensed (spiked) into rat plasma (supplied by Bioivt formerly Bioreclamation, Cat. No. RAT00PLK2Y2N, Bioivt, Hicksville N.Y. USA) as Sprague Dawley male rat plasma prepared by collection of blood into potassium-EDTA "K2-EDTA" tubes, centrifuged and stored at −80 C until usage). Standard LCMS (liquid chromatography mass spectrometry) was performed using an AB Sciex Exion instrument and Mass Spectrometry (MS) detection by API 5500 instrument. An autosampler AD multiplate was used (AB Sciex). The HPLC method used a Restek Force Biphenyl column (dimensions 2.1×30 mm, 1.8 micrometer particle size) eluted using a gradient with a flow rate of 0.6 mL/min with two mobile phases (Mobile Phase A: Water with 0.1% Formic Acid and Mobile Phase B: Acetonitrile with 0.1% Formic Acid). MS detection and calibration for Compound 1 or Compound 2 used Tolbutamide also as an Internal Standard. The lower limit of quantification of Compound 1 or Compound 2 based on the conditions used was 1 ng/ml and the standard curve was linear to 5,000 ng/ml. Compound 2 levels were below limit of detection in vivo. Compound 2 levels were stable in vitro incubated in physiological buffers with or without fatty acid free Bovine Serum Albumin (Sigma-Aldrich, St Louis Mo.) for incubation time of 30 minutes at 37 degrees C. Compound 2 was hydrolyzed to Compound 1 by rat plasma in vitro studies within minutes when incubated at 37 degrees C. Compound 2 hydrolysis by rat plasma was blocked by pretreatment of the rat plasma (37 degrees C. for 5 min with 10 micromolar concentration of the serine hydrolase esterase inhibitor methyl arachidonoyl fluoro phosphonate supplied by Sigma Aldrich).

PK (Pharmacokinetics) Studies of Compounds 1 or 2 In Vivo in Sprague Dawley Male Rats.

Figure 4:
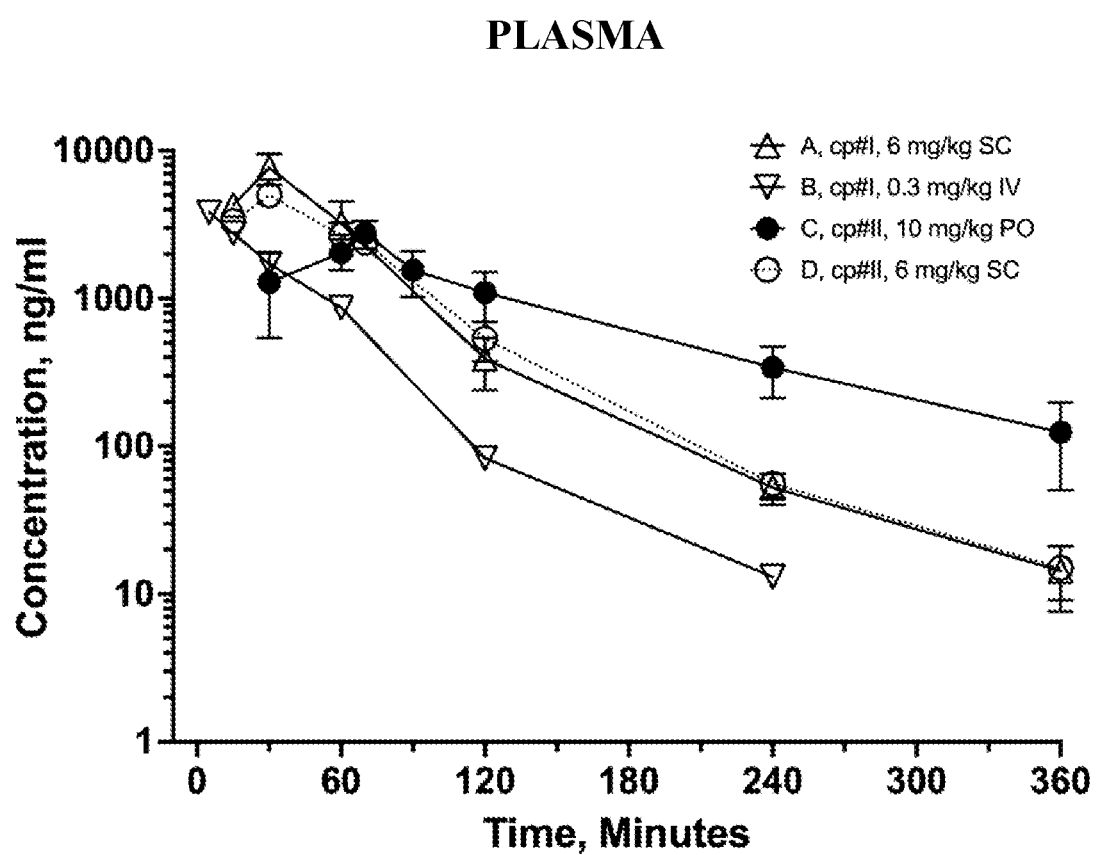
FIG. 4 illustrates the results of a single acute administration pharmacokinetic study of Compound 1 or Compound 2 treatment of Sprague Dawley rats, wherein Compound 1 is measured in plasma samples by LCMS.
Figure 5:
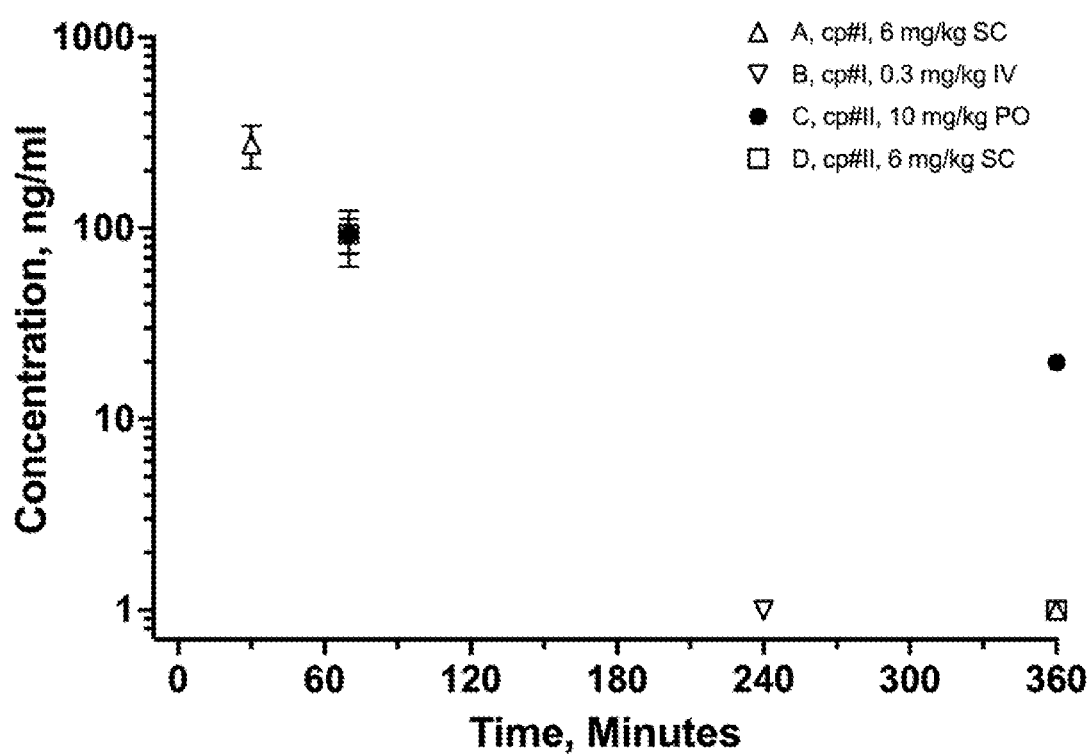
FIG. 5 illustrates the results of a single acute administration pharmacokinetic study of Compound 1 or Compound 2 treatment of Sprague Dawley rats, wherein Compound 1 is measured in brain samples by LCMS.
Figure 6:
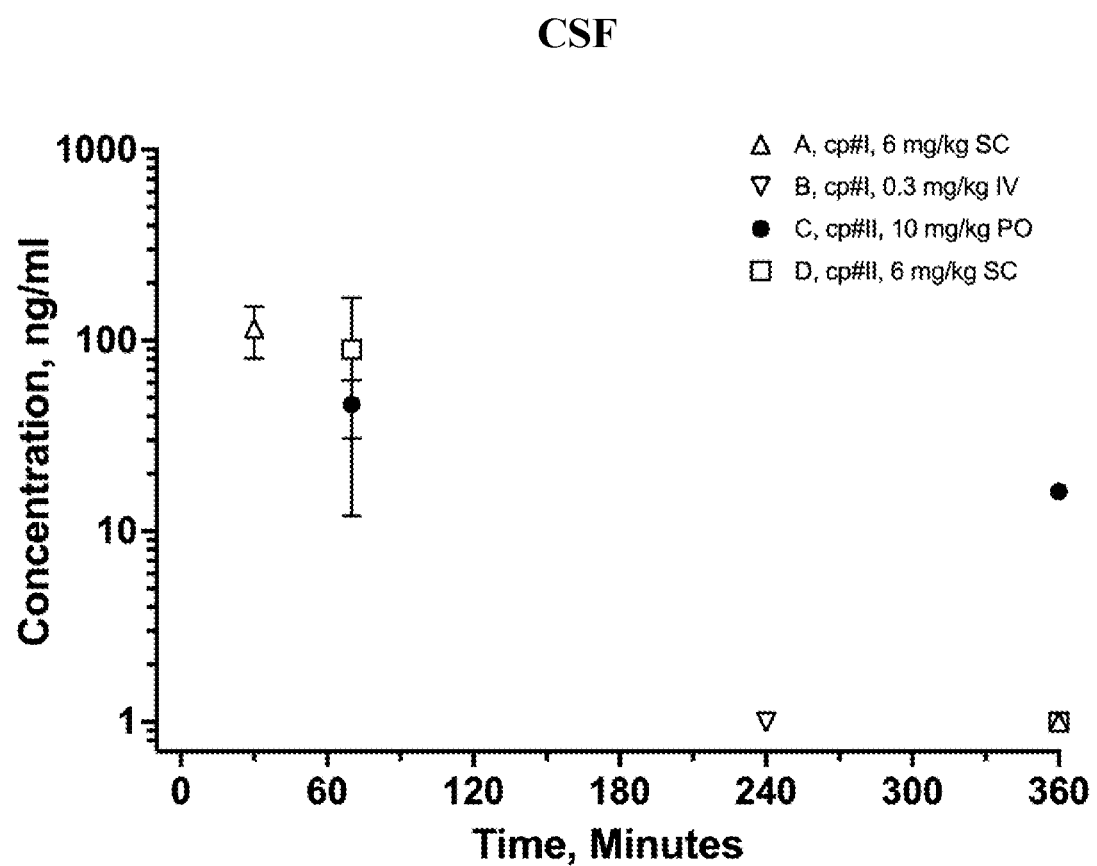
FIG. 6 illustrates the results of a single acute administration pharmacokinetic study of Compound 1 or Compound 2 treatment of Sprague Dawley rats, wherein Compound 1 is measured in cerebral spinal fluid (CSF) samples by LCMS.

Acute administration of test compound 1 or test compound 2 by routes described (either PO, SC or IV) was done to rats and samples collected at the timepoints described for subsequent extraction, dissolution and quantitative LCMS bioanalysis. See FIG. 4, FIG. 5, and FIG. 6. In these FIGS., A through E represent different treatment groups of rats (A,B,C,D,E) administered various formulations by various routes of compound 1 or compound 2 respectively (as specified). Treatment group A rats were administered SC administration of Cp#1 (formulated in saline pH elevated to pH 9.5 by NaOH; pH adjusted to 7.3 using HCl). Rats treatment group B was administered Cp#1 (formulated in saline pH elevated to pH 9.5 by NaOH; pH adjusted to 7.3 using HCl) by the intravenous (IV) route. Rats treatment group C was administered Cp#2 HCl (formulated as a solution at concentration 10 mg/ml in 0.5% methylcellulose in water, 3% DMSO) by PO route. Rats treatment group D was administered Cp#2 HCl (formulated as a solution at concentration 10 mg/ml in 0.5% methylcellulose in water, 3% DMSO) by subcutaneous SC route. The PO 10 mg/kg dose and SC 6 mg/kg dose were administered from a 10 mg/ml concentration solution of Cp#2.

SAD Study of Compound 2 In Vivo in Sprague Dawley Male Rats.

Figure 7A:
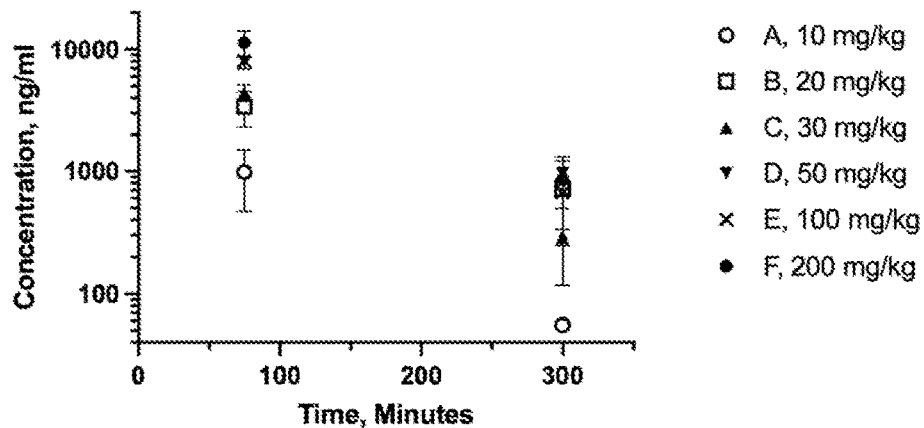
FIGS. 7A-7C illustrate the results of single ascending dose (SAD) studies of acute oral administration of Compound 2 with 1-day treatment in vivo in Sprague Dawley rats, wherein Compound 1 is measured in plasma (FIG. 7A), CSF (FIG. 7B), and brain (FIG. 7C) samples by LCMS at 75 minutes and 300 minutes.
Figure 7B:
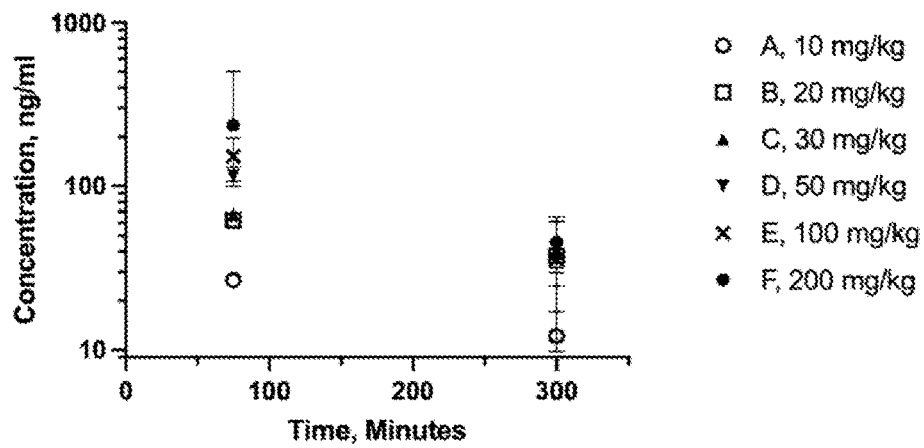
Figure 7C:
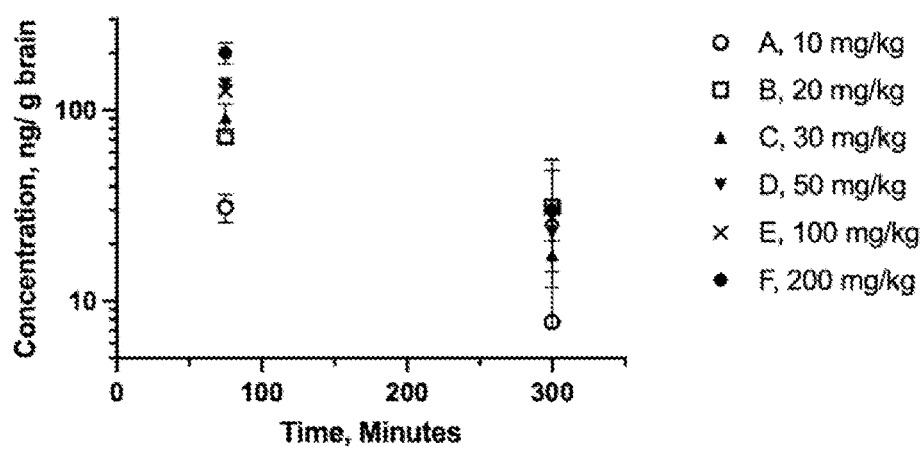

Single Ascending Dose (SAD) 1-day acute administration of test compound 2 by the oral PO route of administration to rats and samples collected at the timepoints described for subsequent extraction, dissolution and quantitative LCMS bioanalysis. See FIG. 7. In treatment groups of rats A through D, doses (A 10 mg/kg, B 20 mg/kg, C 30 mg/kg, D 50 mg/kg) were administered from a solution of Cp#2 formulated in 0.5% methylcellulose in water and 3% DMSO with Compound 2 a concentration of 10 mg/ml. In treatment groups of rats E and F, doses (E 100 mg/kg and F 200 mg/kg) were administered from a stable suspension of Cp#2 formulated in 0.5% methylcellulose in water and 3% DMSO at a concentration of 50 mg/ml.

Irwin test of live rats was conducted in the SAD study 55-60 minutes post treatment of test compound 2 on day 1 (the only day of the study). See FIG. 10. Note: for endpoint the data are presented from left to right ascending doses 10 mg/kg, 20 mg/kg, 30 mg/kg 50 mg/kg, 100 mg/kg, 200 mg/kg beneath each endpoint presented on the X axis. Normal or very little change from normal was observed for many of the doses and no bar is shown for a value of Zero.

Figure 8A:
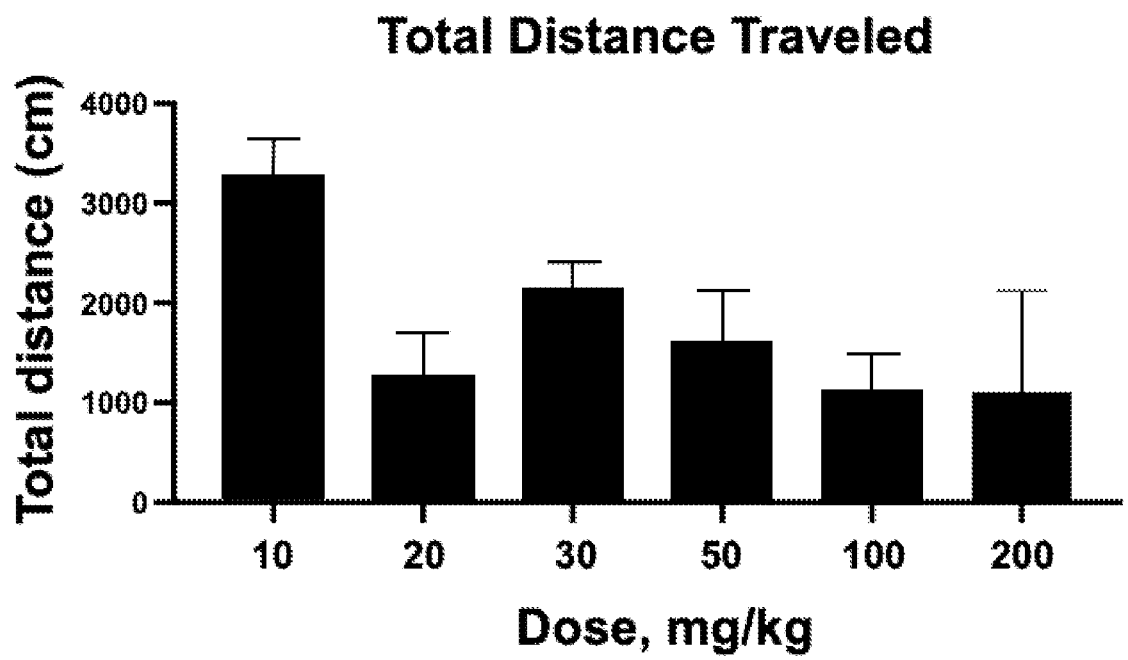
FIGS. 8A and 8B illustrate the results of an open field assay (OFA) on the same animals as in the SAD studies of FIGS. 7A-7C, wherein the total distance traveled (FIG. 8A) and vertical time exploring (FIG. 8B) were measured.
Figure 8B:
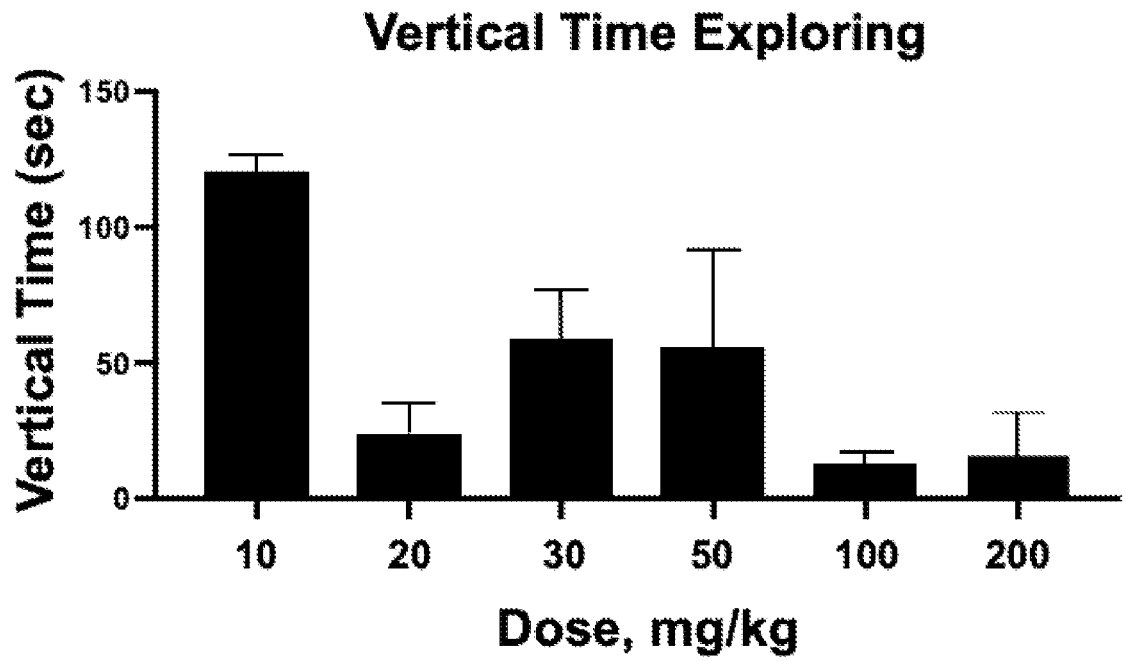
Figure 9A:
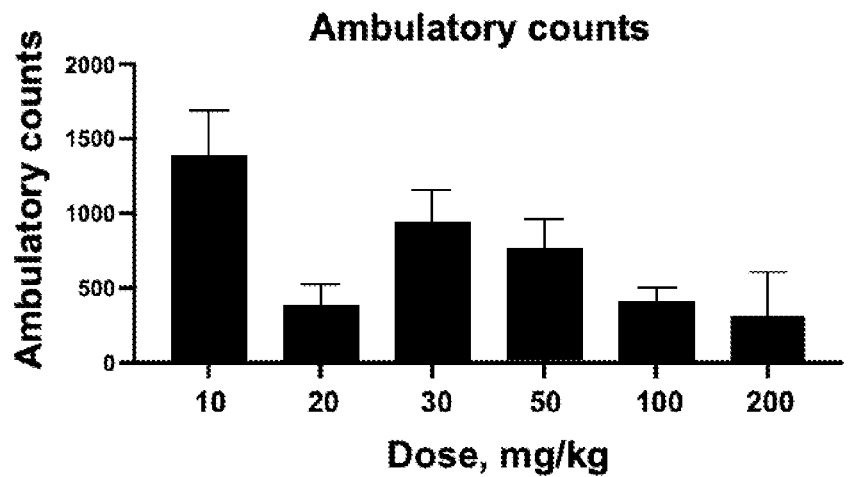
FIGS. 9A-9C illustrate further results of the OFA in FIGS. 8A and 8B, wherein ambulatory movement (FIG. 9A) and stereotypical movement (FIG. 9B) were counted and resting time (FIG. 9C) was measured.
Figure 9B:
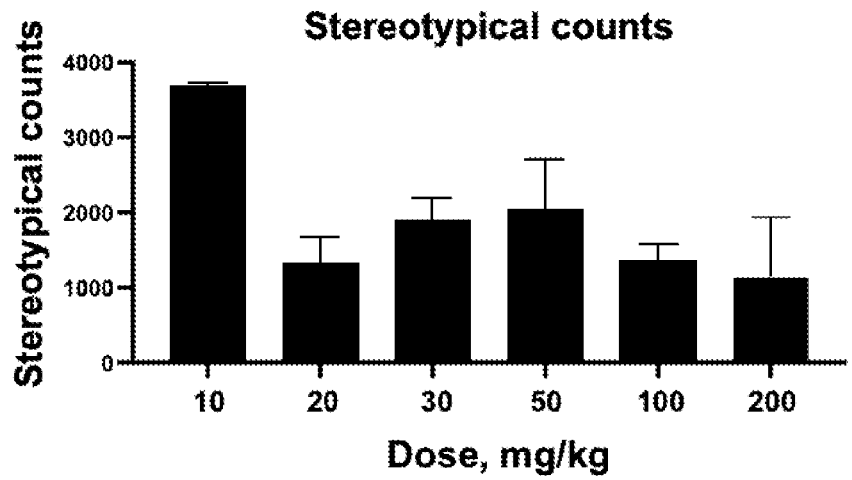
Figure 9C:
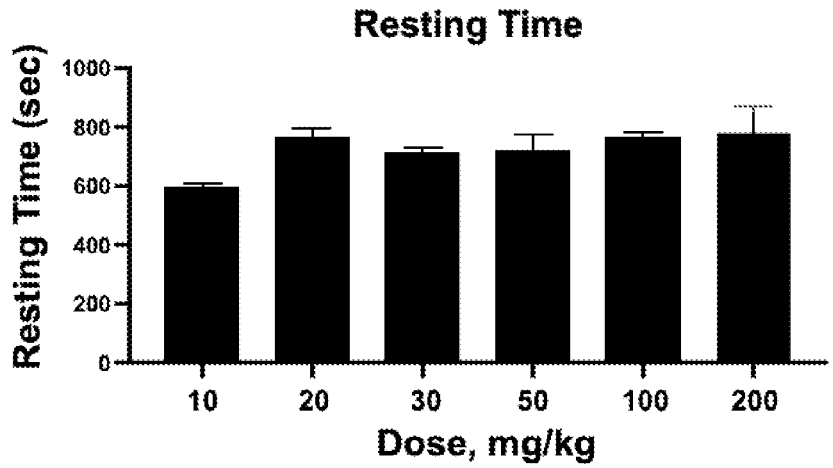
Figure 10A:
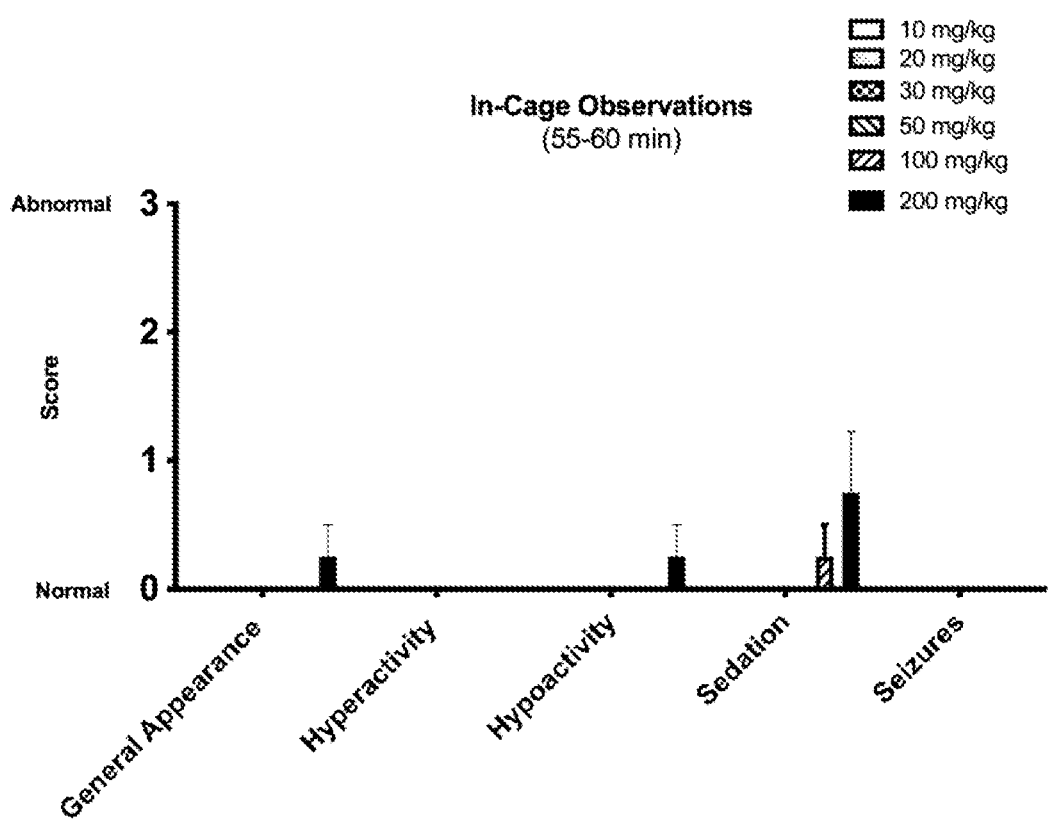
FIGS. 10A-10D illustrate the results of an Irwin neurological test battery on the same animals in the SAD studies of FIGS. 7A-7C, wherein in-cage observations (FIG. 10A), autonomic responses (FIG. 10B), and suspended tests (FIG. 10C) were scored, and fecal pellets (FIG. 10D) were counted.
Figure 10B:
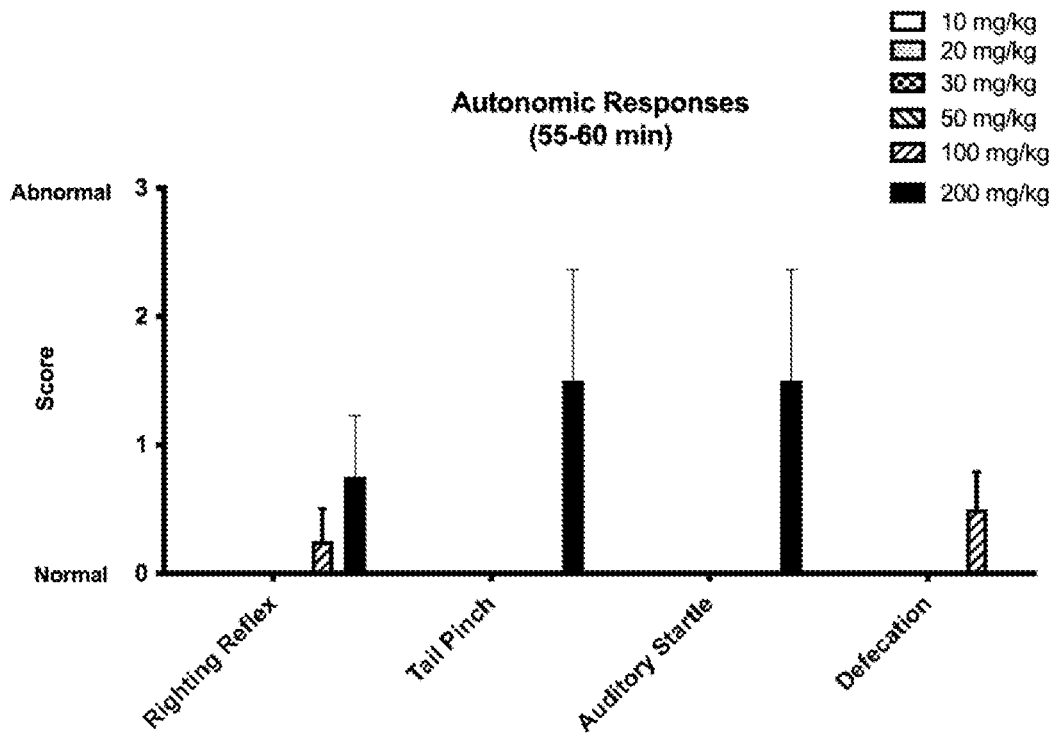
Figure 10C:
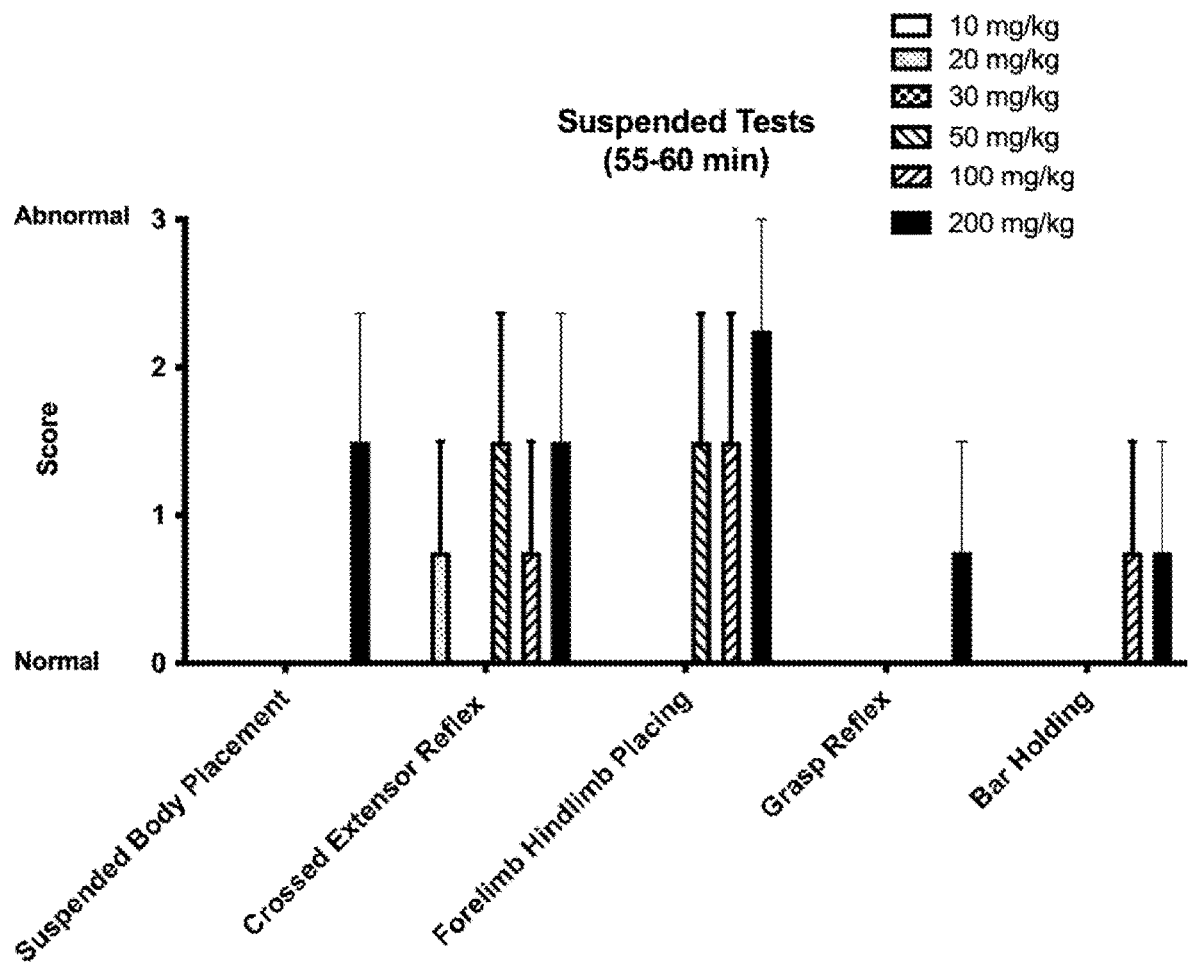
Figure 10D:
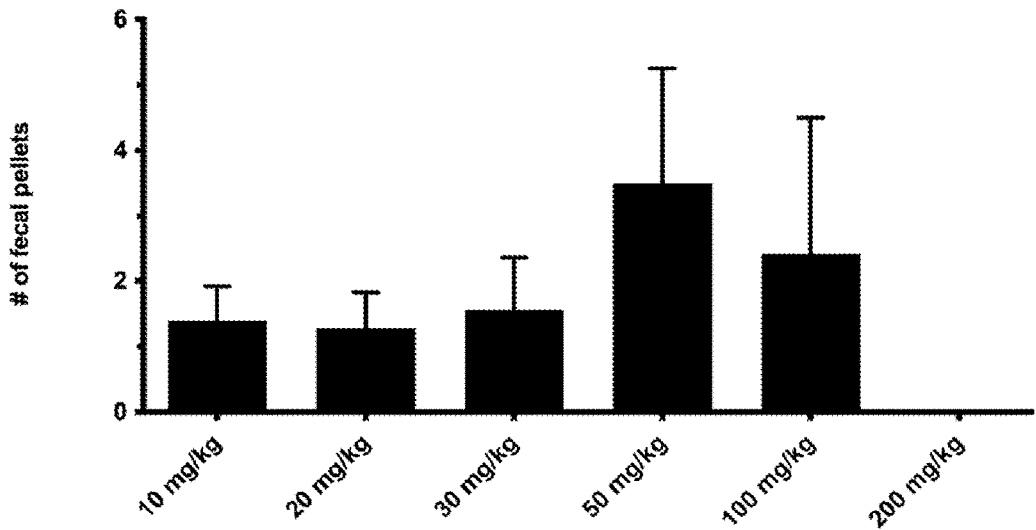

OFA (open field activity) of live rats was conducted 60-75 minutes post treatment of test compound 2 on this 1-day study. See FIG. 8 and FIG. 9.

MAD Study of Compound 2 In Vivo in Sprague Dawley Male Rats.

Figure 15A:
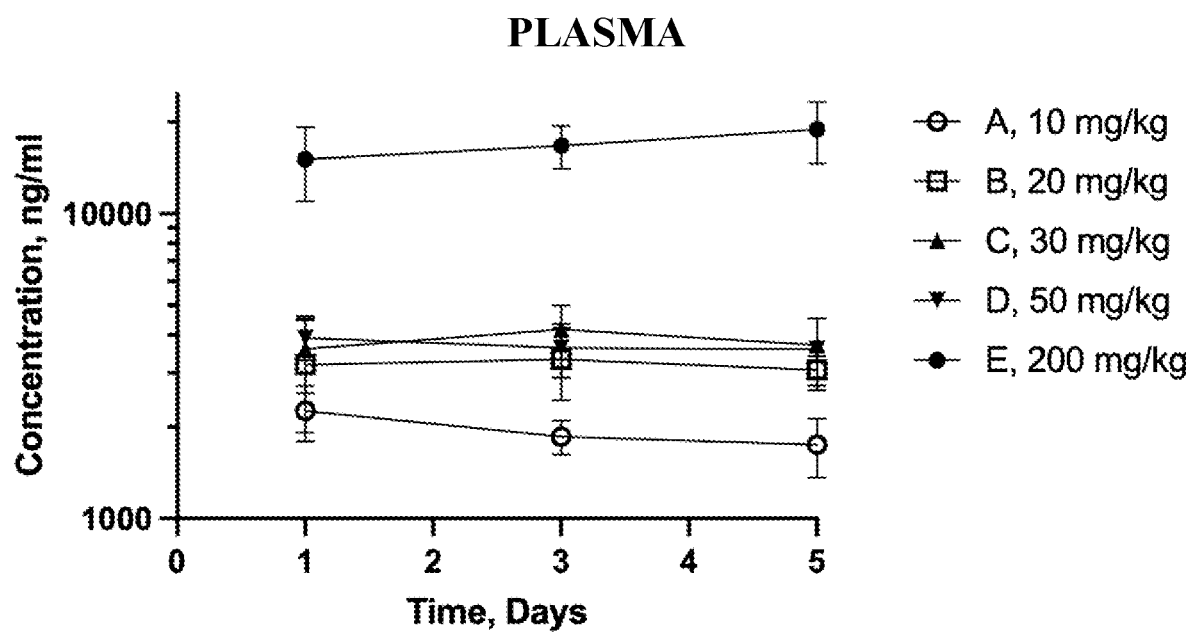
FIGS. 15A and 15B illustrate the results of MAD studies with once daily oral administration of Sprague Dawley rats for five days, wherein the level of Compound 1 is measured in plasma by LCMS on days 1, 3, and 5; Compound 1 concentration is plotted versus time (FIG. 15A) and dose (FIG. 15B)
Figure 15B:
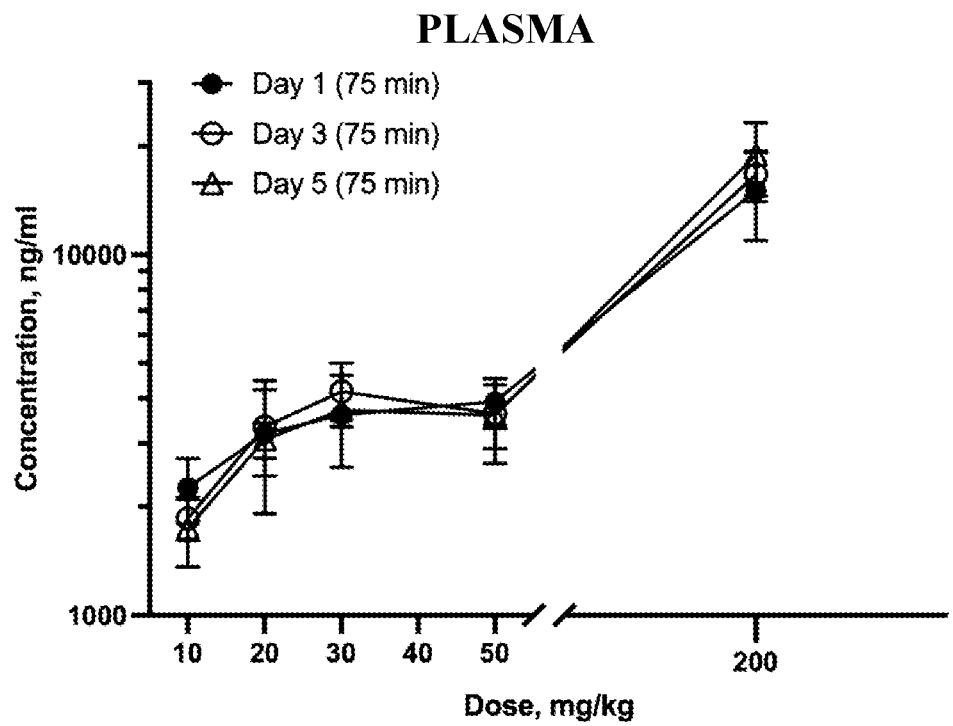
Figure 16:
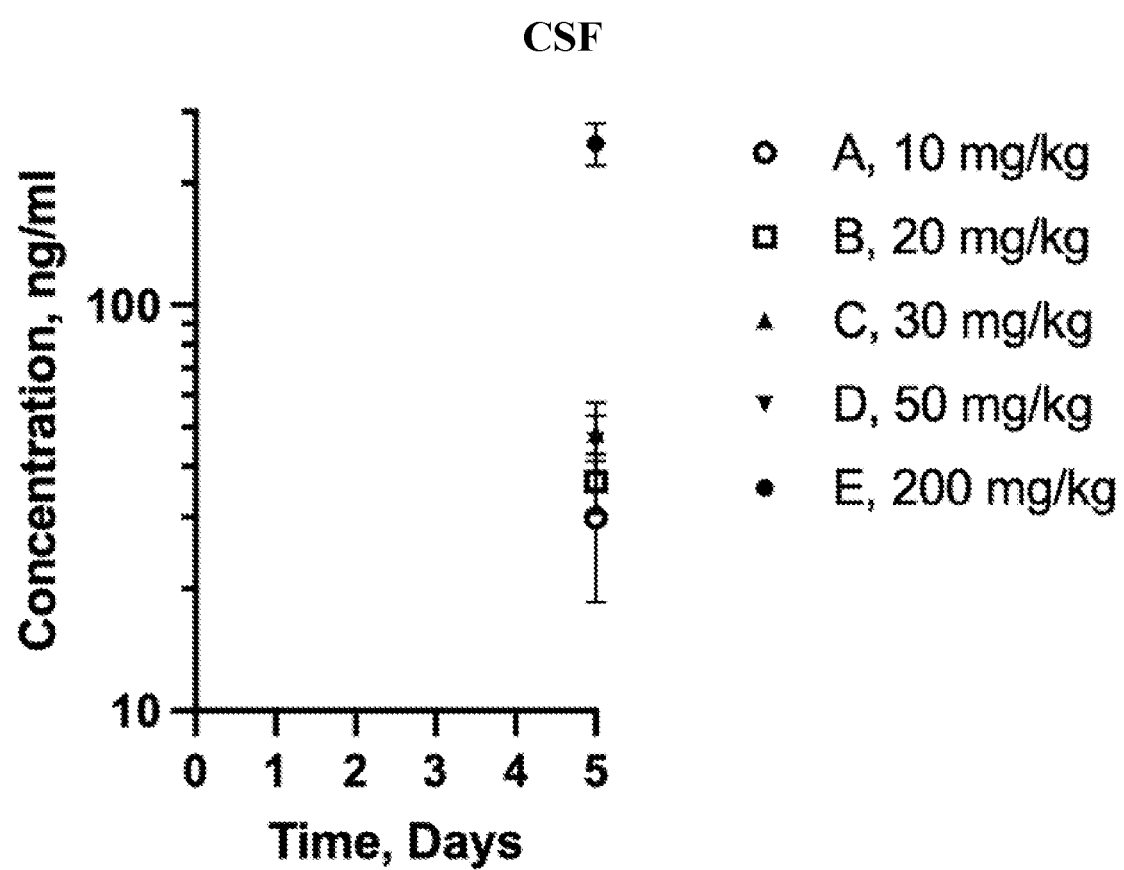
FIG. 16 illustrates the results of the same MAD studies in FIGS. 15A and 15B, wherein the level of Compound 1 is measured in CSF by LCMS on day 5.
Figure 17:
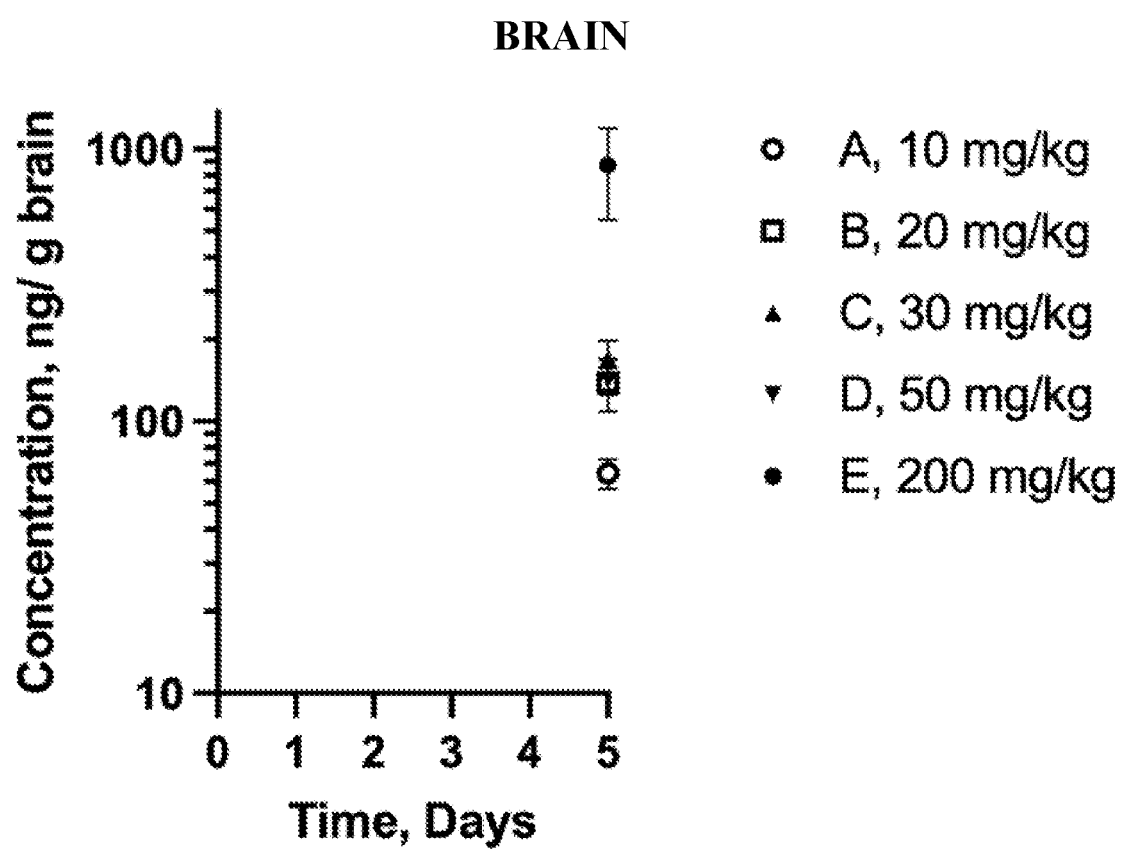
FIG. 17 illustrates the results of the same MAD studies in FIGS. 15A and 15B, wherein the level of Compound 1 is measured in brain on day 5.

Multiple Ascending Dose (MAD) 5-day once daily administration of test compounds was done to rats and samples collected at the timepoints described for subsequent extraction, dissolution and quantitative LCMS bioanalysis. In treatment groups of rats A through D, doses (A 10 mg/kg, B 20 mg/kg, C 30 mg/kg, D 50 mg/kg) were administered from a solution of Cp#2 formulated in 0.5% methylcellulose in water and 3% DMSO with Compound 2 a concentration of 10 mg/ml. In treatment group of rats E, dose (E 200 mg/kg) was administered from a stable suspension of Cp#2 formulated in 0.5% methylcellulose in water and 3% DMSO at a concentration of 50 mg/ml. See FIG. 15, FIG. 16, and FIG. 17. Irwin test of live rats was conducted in the MAD study 55-60 minutes post treatment of test compound 2 on two different treatment days (day 3 and day 5). See FIG. 13 and FIG. 14. Note: for endpoint the data are presented from left to right ascending doses 10 mg/kg, 20 mg/kg, 30 mg/kg 50 mg/kg, 100 mg/kg, 200 mg/kg beneath each endpoint presented on the X axis. Normal or very little change from normal was observed for many of the doses and no bar is shown for a value of Zero.

Figure 11:
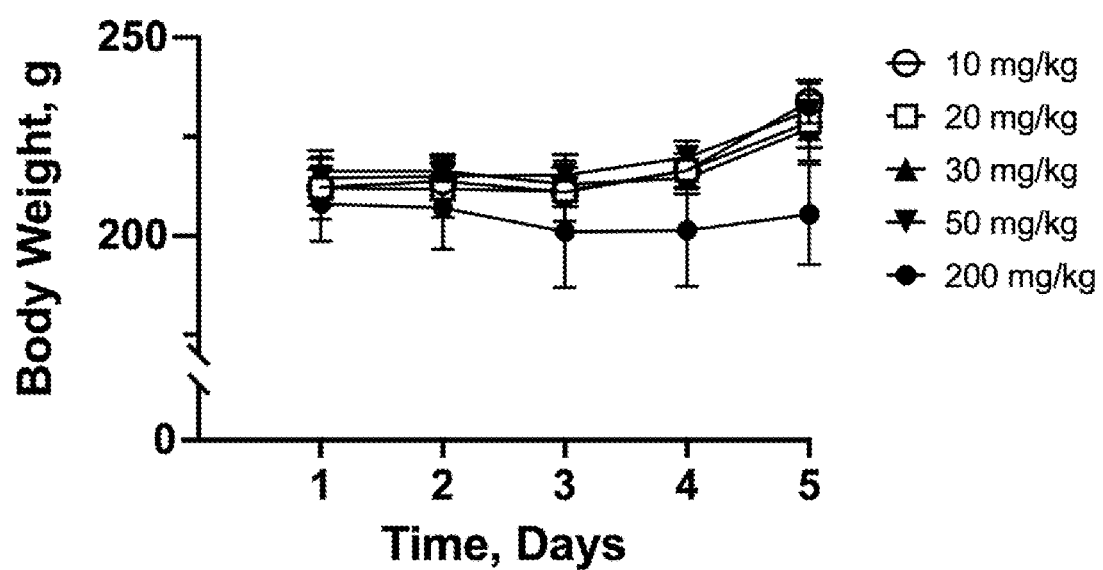
FIG. 11 illustrates the results of body weight measurements of Sprague Dawley rats participating in a multiple ascending dose (MAD) study of 5-days with once daily dosing.
Figure 12:
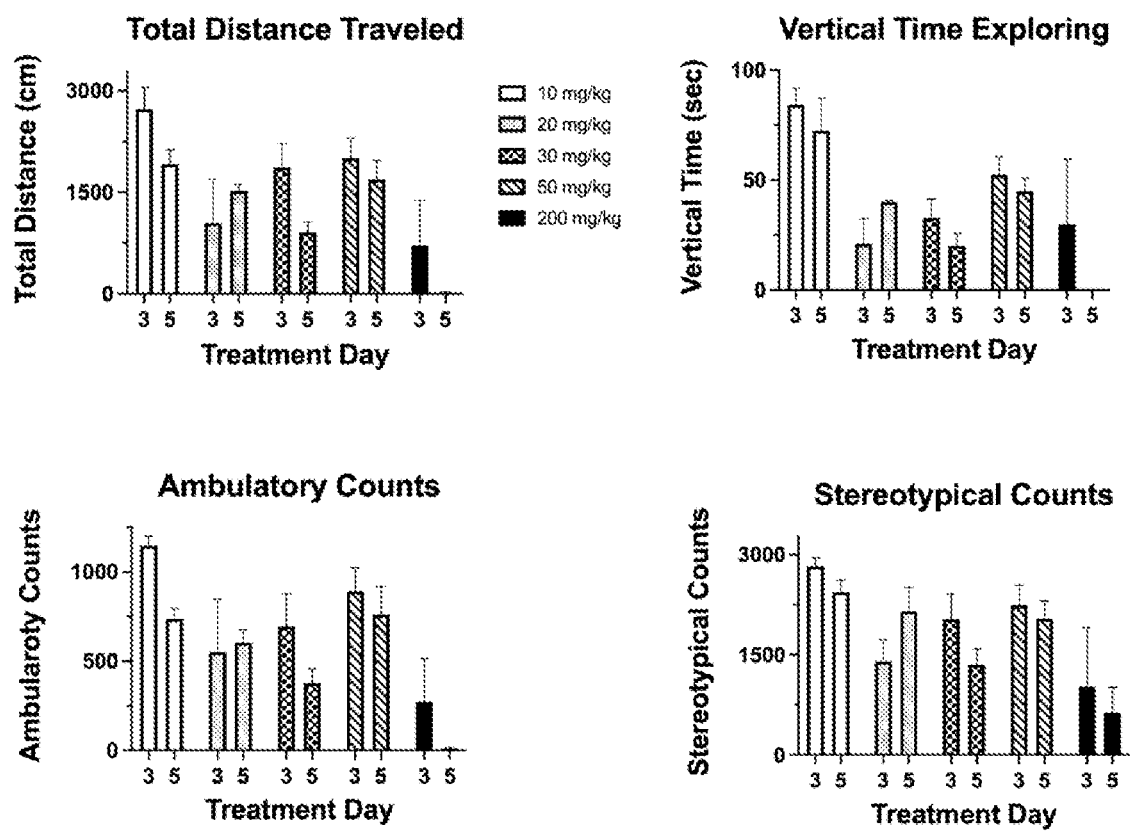
FIG. 12 illustrates the results of an OFA on the same Sprague Dawley rats as in FIG. 11, wherein the total distance traveled and vertical time exploring were measured and ambulatory movement and stereotypical movement were counted.
Figure 13A:
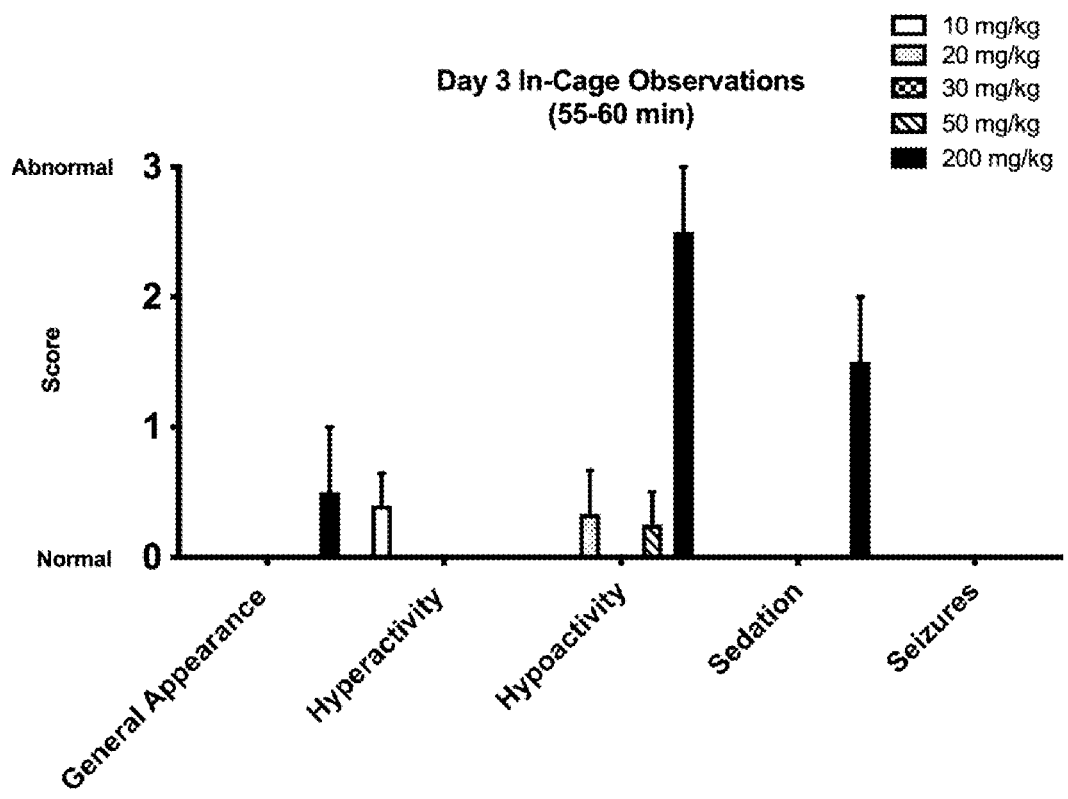
FIGS. 13A-13D illustrate the results of an Irwin neurological test battery on the same Sprague Dawley rats as in FIG. 11, wherein in-cage observations (FIG. 13A), anatomic responses (FIG. 13B), and suspended tests (FIG. 13C) were scored, and fecal pellets (FIG. 13D) were counted; performed on day three (3) of the MAD study.
Figure 13B:
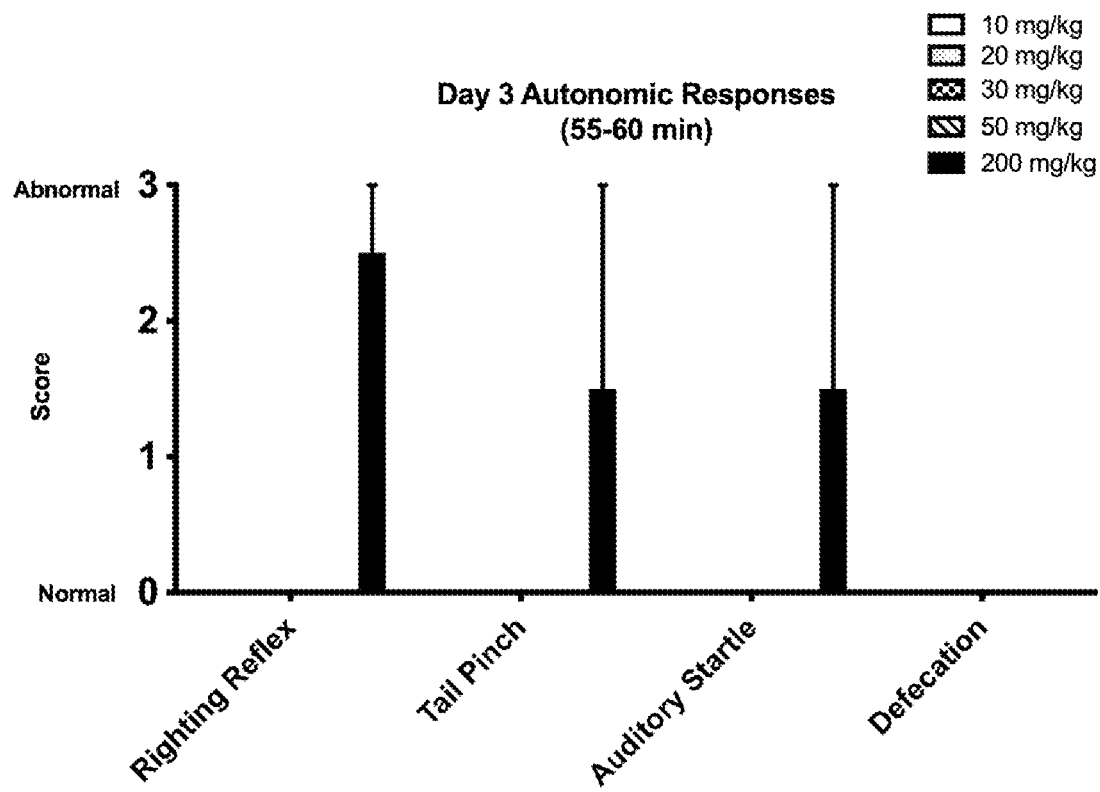
Figure 13C:
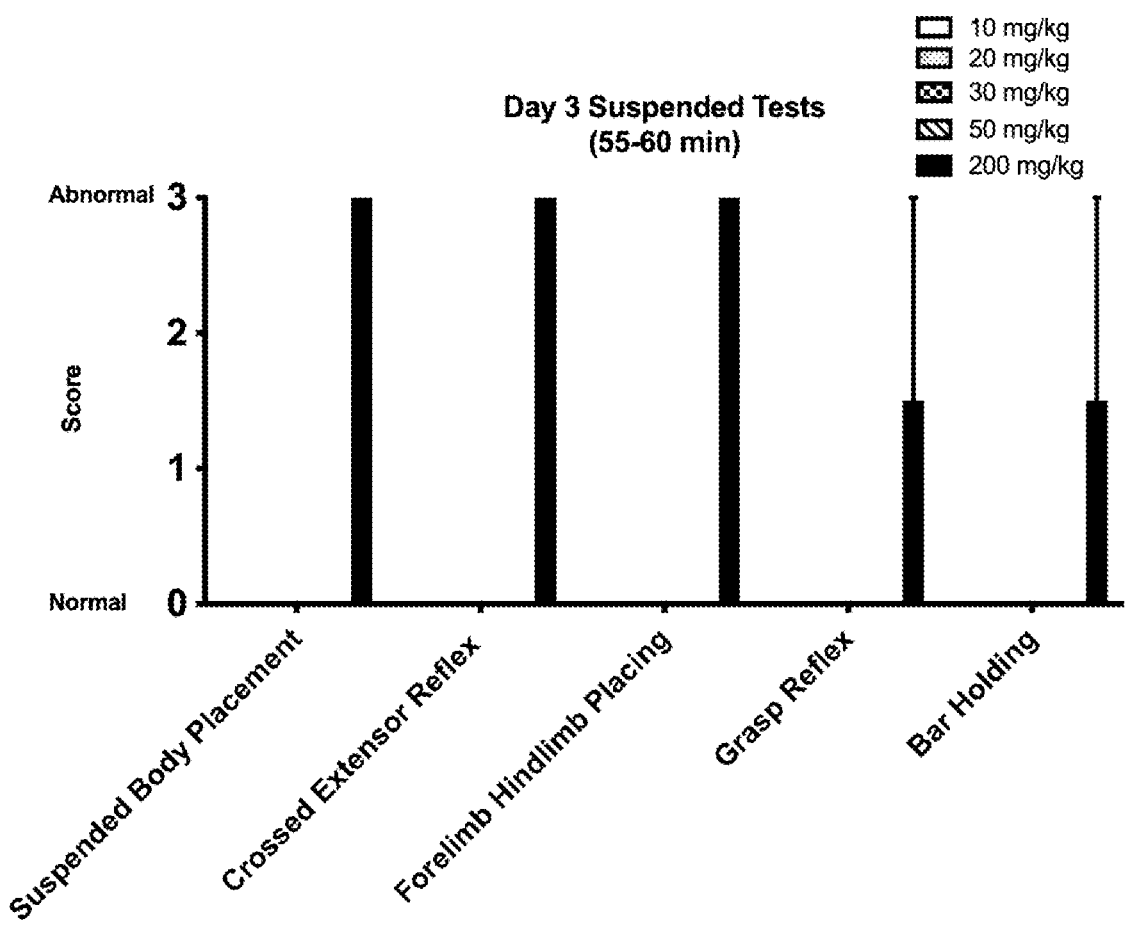
Figure 13D:
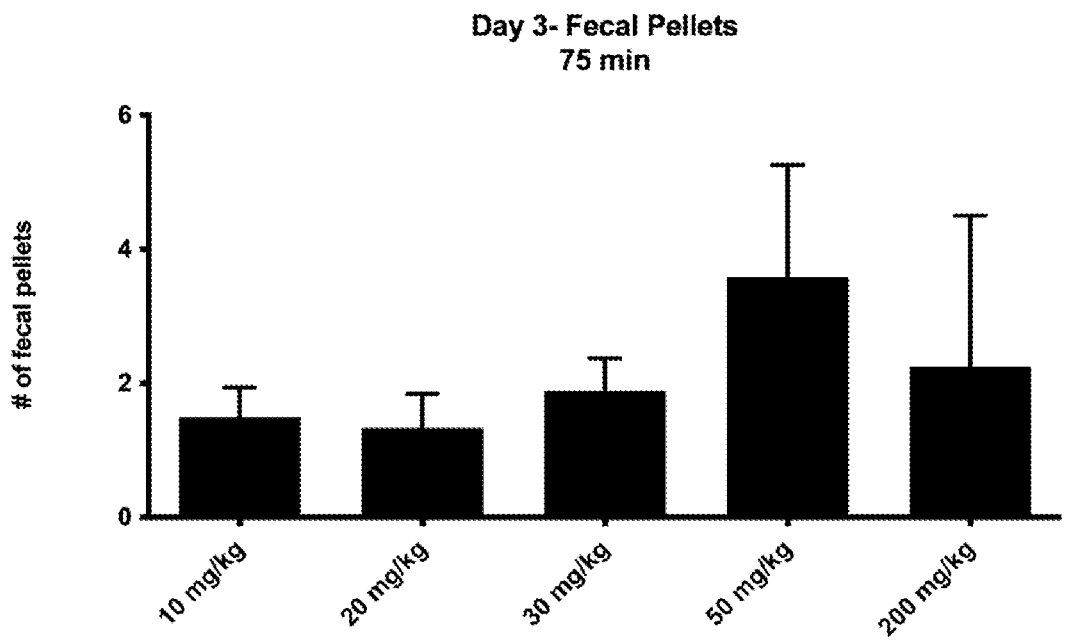
Figure 14A:
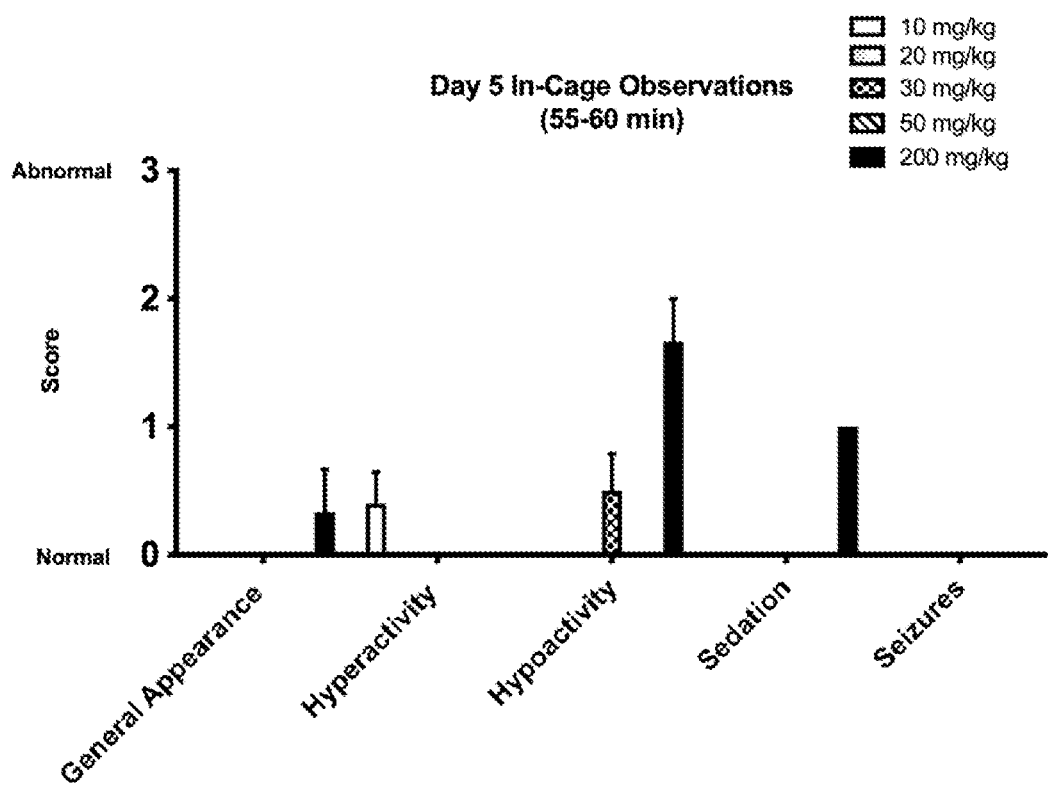
FIGS. 14A-14D illustrate the results of an Irwin neurological test battery on the same Sprague Dawley rats as in FIGS. 13A-13D, wherein in-cage observations (FIG. 14A), anatomic responses (FIG. 14B), and suspended tests (FIG. 14C) were scored, and fecal pellets (FIG. 14D) were counted; performed on day five (5) of the MAD study.
Figure 14B:
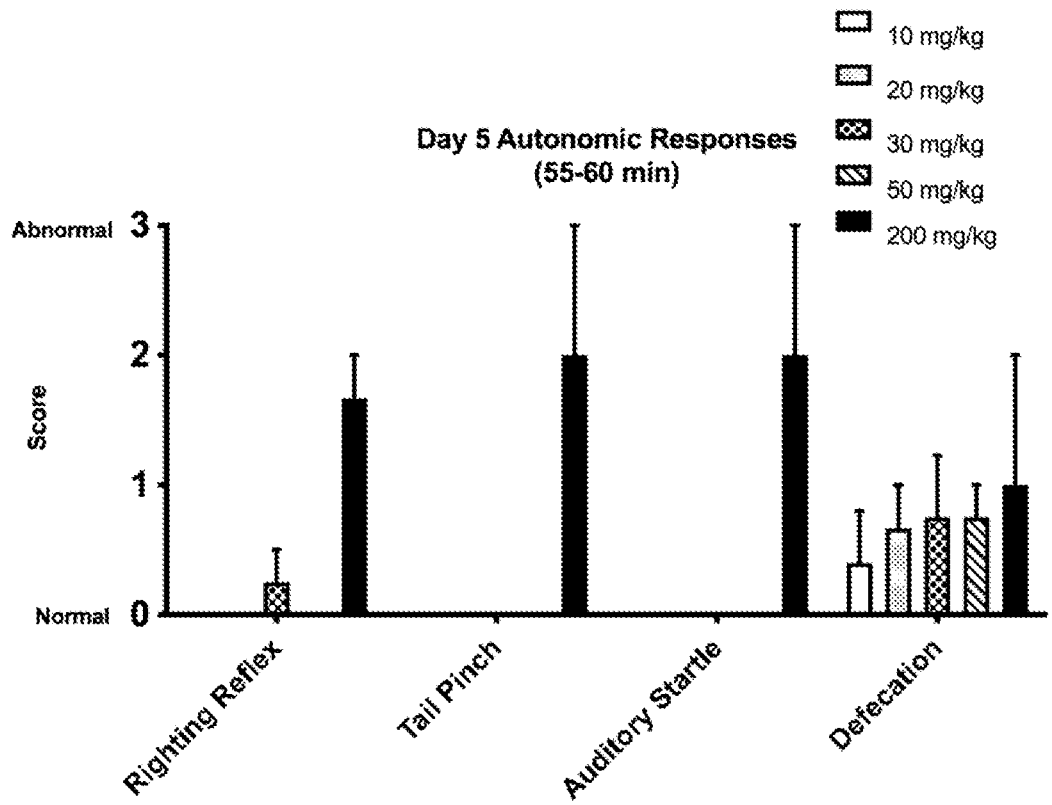
Figure 14C:
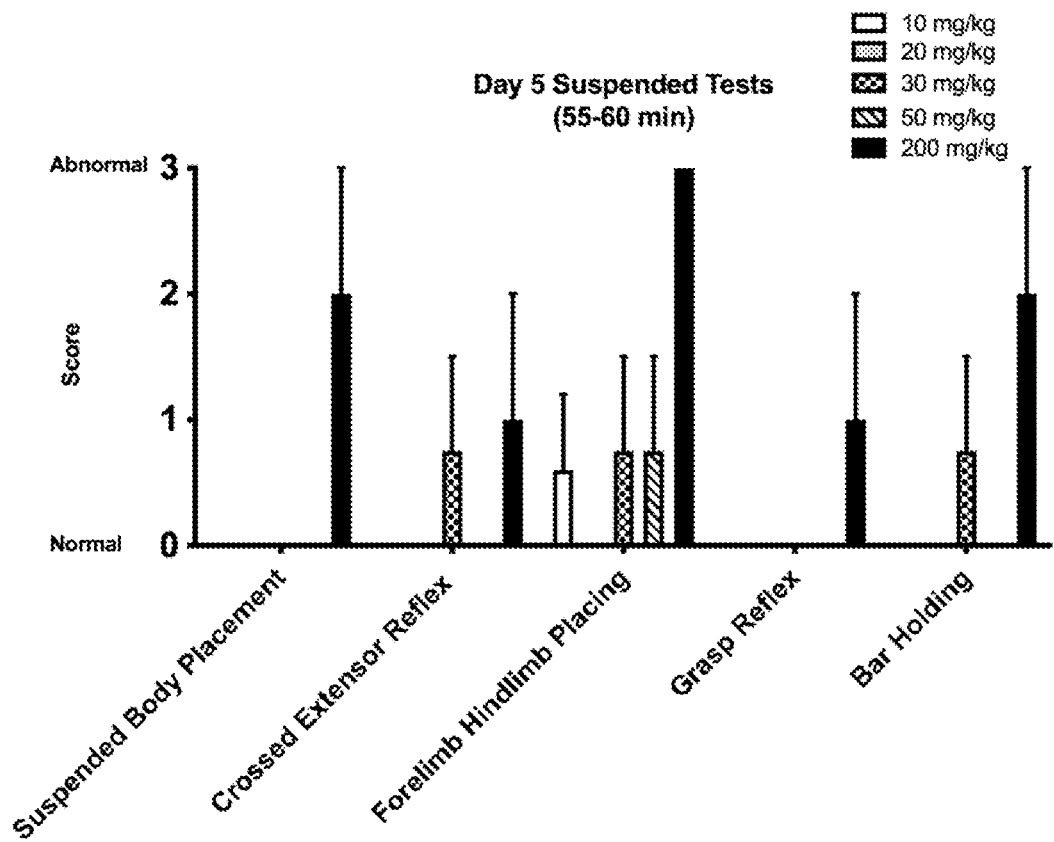
Figure 14D:
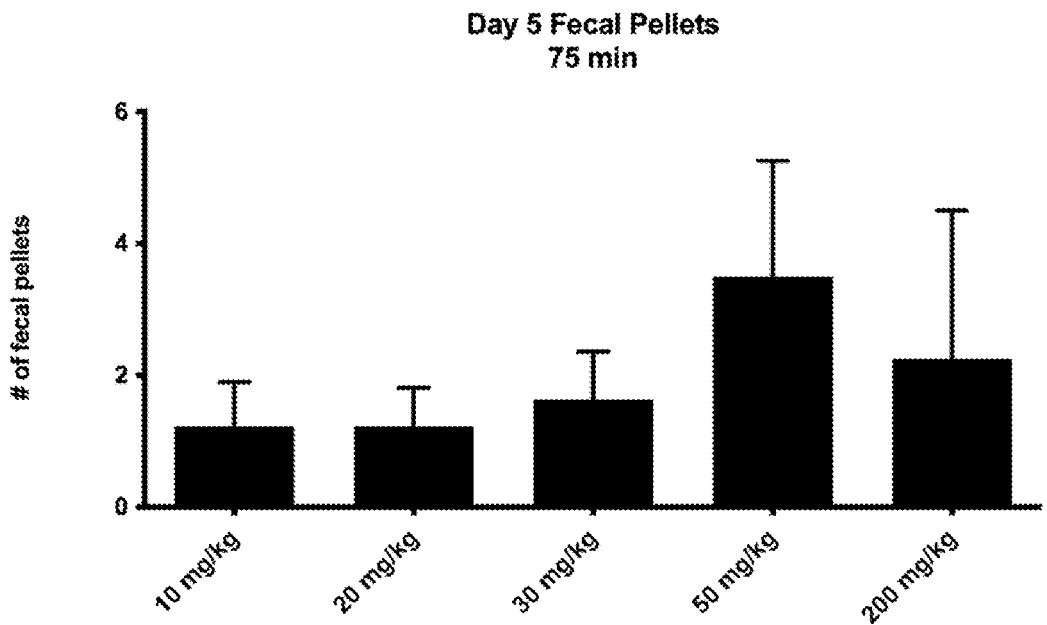

OFA (open field activity) of live rats was conducted 60-75 minutes post treatment of test compound 2 on two different treatment days (day 3 and day 5). See FIG. 11 and FIG. 12.

The invention claimed is:

1. A compound of formula I:

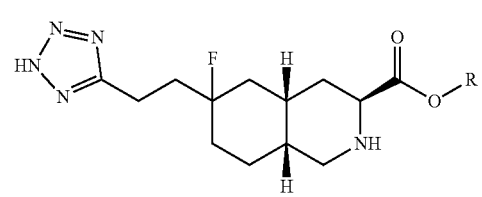

wherein:
R is selected from H and $(C_1-C_{20})$hydrocarbyl.

2. A compound according to claim 1 of formula II:

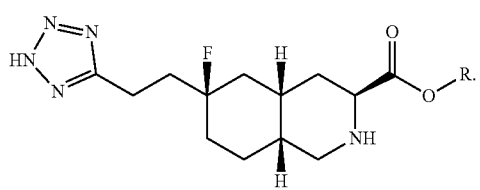

3. A compound according to claim 2 wherein R is selected from H and aliphatic $(C_1-C_{20})$hydrocarbyl optionally substituted with one or two phenyl groups with the proviso that R contains twenty carbons or less.

4. A compound according to claim 2 wherein R is H or $C_nH_m$, and wherein:
n is 1 and m is 3;
n is 2 and m is 5;
n is 3 and m is 3, 5, or 7;
n is 4 and m is 5, 7, or 9;
n is 5 and m is 7, 9, or 11;
n is 6 and m is 5, 7, 9, 11, or 13;
n is 7 and m is 7, 9, 11, 13, or 15;
n is 8 and m is 5, 7, 9, 11, 13, 15, or 17;

n is 9 and m is 7, 9, 11, 13, 15, 17, or 19;
n is 10 and m is 7, 9, 11, 13, 15, 17, 19, or 21;
n is 11 and m is 9, 11, 13, 15, 17, 19, 21, or 23;
n is 12 and m is 7, 9, 11, 13, 15, 17, 19, 21, 23, or 25;
n is 13 and m is 9, 11, 13, 15, 17, 19, 21, 23, 25, or 27;
n is 14 and m is 9, 11, 13, 15, 17, 19, 21, 23, 25, 27, or 29;
n is 15 and m is 11, 13, 15, 17, 19, 21, 23, 25, 27, 29, or 31;
n is 16 and m is 9, 11, 13, 15, 17, 19, 21, 23, 25, 27, 29, 31, or 33;
n is 17 and m is 11, 15, 17, 19, 21, 23, 25, 27, 29, 31, 33, or 35;
n is 18 and m is 11, 13, 15, 17, 19, 21, 23, 25, 27, 29, 31, 33, 35, or 37;
n is 19 and m is 13, 15, 17, 19, 21, 23, 25, 27, 29, 31, 33, 35, 37, or 39; or
n is 20 and m is 11, 13, 15, 17, 19, 21, 23, 25, 27, 29, 31, 33, 35, 37, 39, or 41.

5. A compound according to claim 3 wherein R is chosen from: H, methyl, ethyl, n-propyl, isopropyl, cyclopropyl, n-butyl, 1-methylpropyl, 1-methyl-2-ethylbutyl, 2-ethylbutyl, 2-methylpropyl, tert-butyl, 2-methylcyclopropyl, 1-methylcyclopropyl, cyclobutyl, cyclopropylmethyl (i.e.,

), n-pentyl, 1-methylbutyl, 2-methylbutyl, 3-methylbutyl, 1-ethylpropyl, 1,2-dimethylpropyl, 1,1-dimethylpropyl, 2,2-dimethylpropyl, cyclobutylmethyl (i.e.,

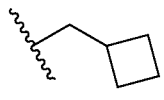 [SMILES: *CC1CCC1]

), 2-(cyclopropyl)ethyl (i.e.,

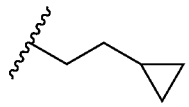 [SMILES: *CCC1CC1]

), cyclopentyl, n-hexyl, 1-methylpentyl, 2-methylpentyl, 3-methylpentyl, 4-methylpentyl, 1,1-dimethylbutyl, 1,2-dimethylbutyl, 1,3-dimethylbutyl, 2,3-dimethylbutyl, 2,2-dimethylbutyl, 3,3-dimethylbutyl, 1,1,2-trimethylpropyl, 1,2,2-trimethylpropyl, 3-(cyclopropyl)propyl (i.e.,

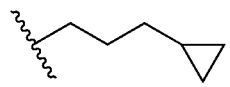

), 2-(cyclobutyl)ethyl (i.e.,

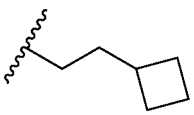 [SMILES: *CCC1CCC1]

), cyclopentylmethyl (i.e.,

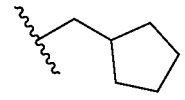 [SMILES: *CC1CCCC1]

), cyclohexyl, cyclohexylmethyl, 2-cyclohexylethyl, dicyclohexylmethyl, n-octyl, benzyl, diphenylmethyl, decyl, dodecyl, tetradecyl, hexadecyl, hexadec-9-enyl, octadecyl, octadec-9-enyl, octadec-9,12-dienyl, 2-propylpentyl, 2-butylhexyl, 2-pentylheptyl, 2-hexyloctyl.

6. A compound according to claim 5 wherein R is chosen from: H, methyl, ethyl, n-propyl, isopropyl, n-butyl, tert-butyl, 2-methylbutyl, and 2-ethylbutyl.

7. A compound according to claim 2, with a structure selected from:

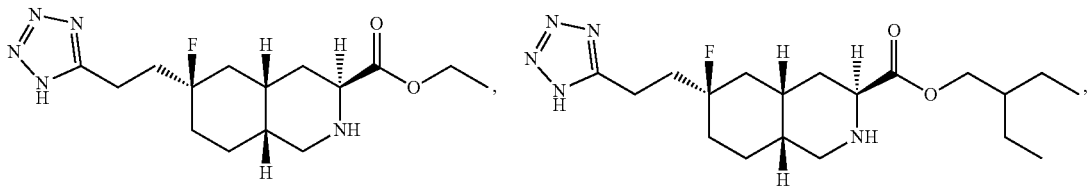

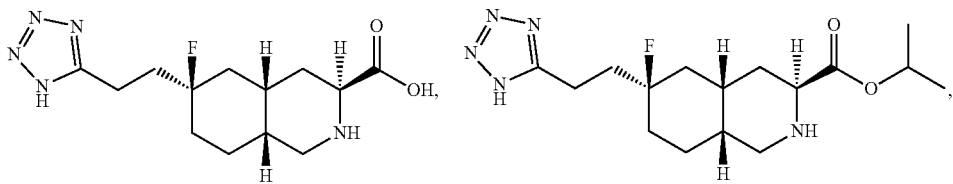

77
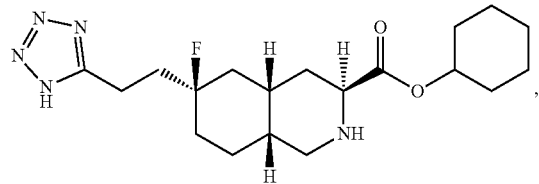
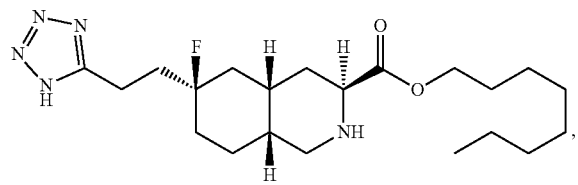
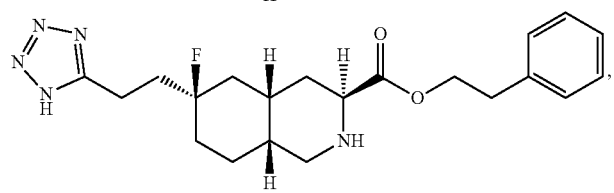
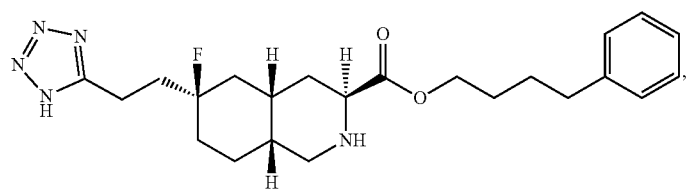
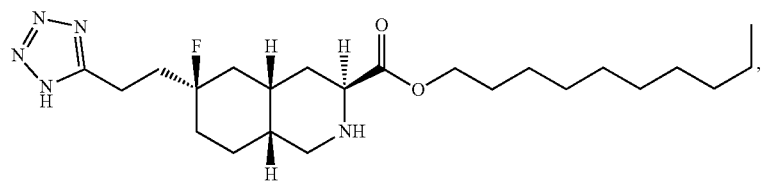
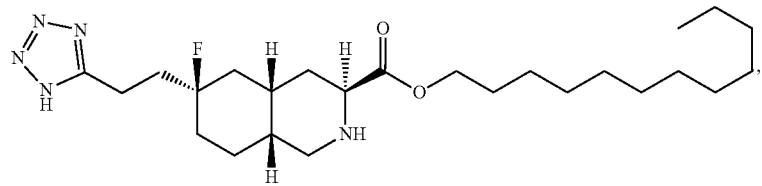
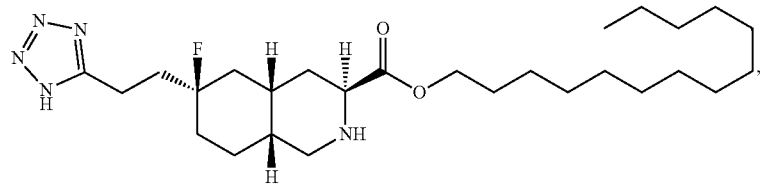
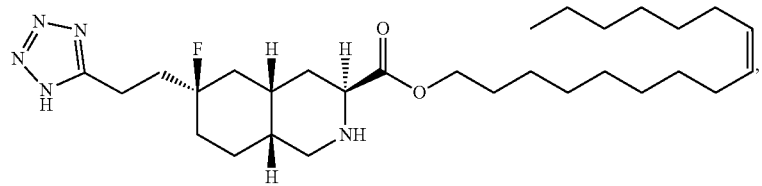
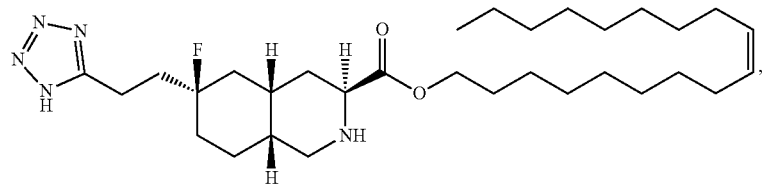
78
-continued
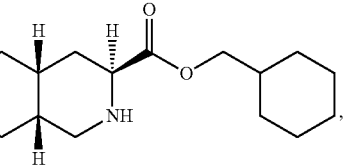
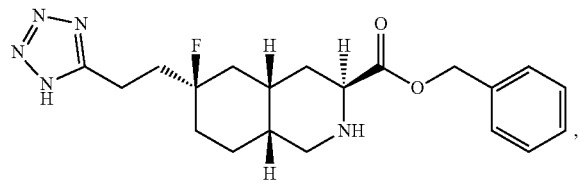

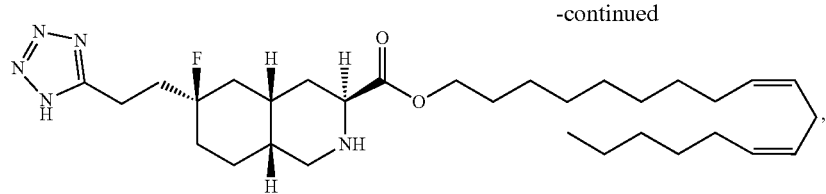
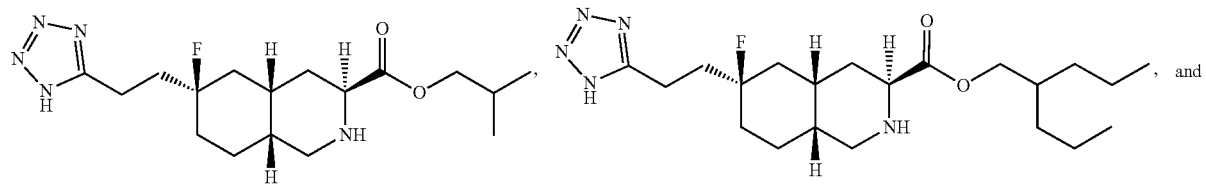
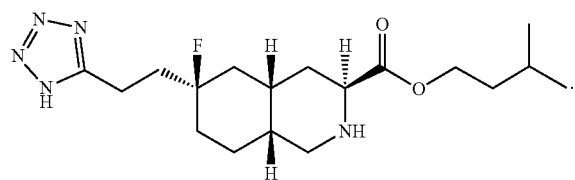
8. A compound according to claim 7, with a structure selected from:
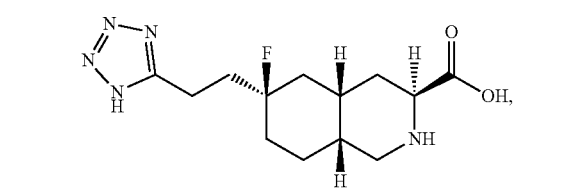 [SMILES: O=C(O)[C@@H]1C[C@H]2C[C@@](F)(CCc3nnn[nH]3)CC[C@H]2CN1]
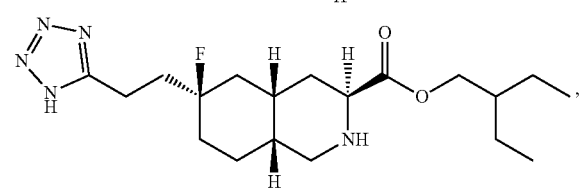
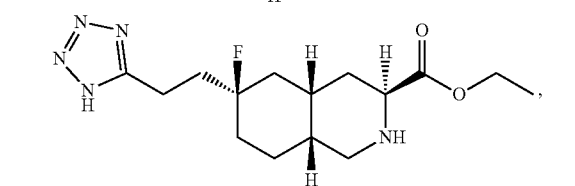
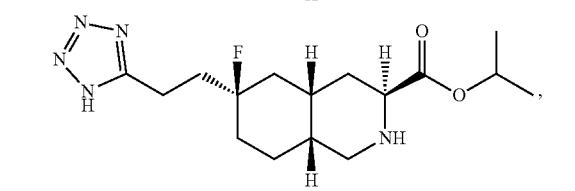
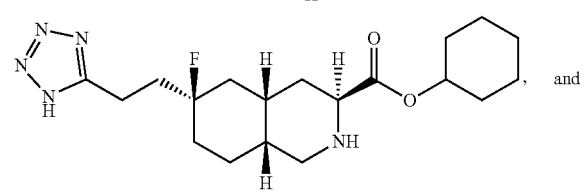
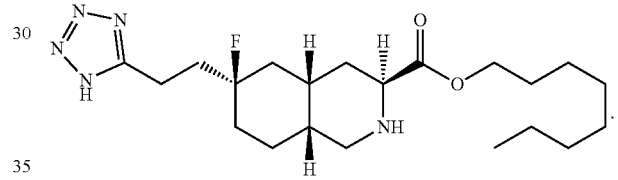
9. A compound according to claim 8, with a structure selected from
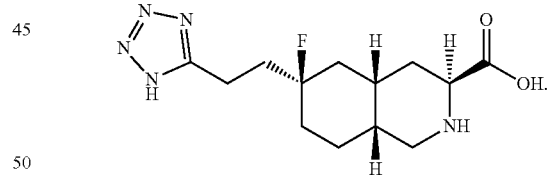
10. A compound according to claim 8, with a structure selected from
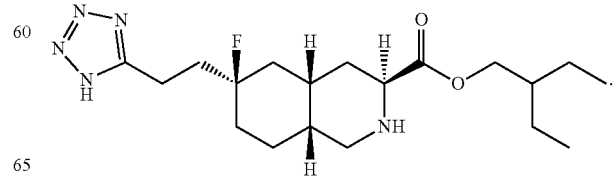

11. A compound according to claim 8, with a structure selected from

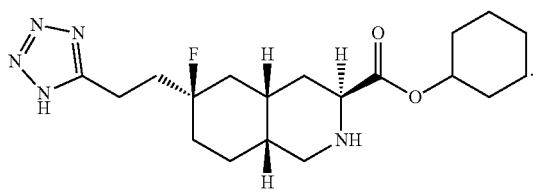 [SMILES: O=C(OC1CCCCC1)[C@@H]1C[C@H]2C[C@@](F)(CCc3nnn[nH]3)CC[C@H]2CN1]

12. A compound according to claim 8, with a structure selected from

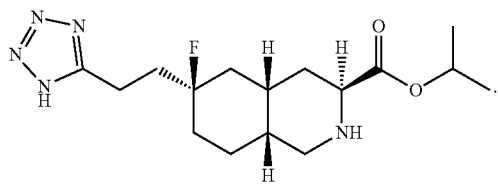 [SMILES: CC(C)OC(=O)[C@@H]1C[C@H]2C[C@@](F)(CCc3nnn[nH]3)CC[C@H]2CN1]

13. A pharmaceutical composition comprising a pharmaceutically acceptable carrier and a compound according to claim 1, or a pharmaceutically acceptable salt thereof.

14. A method of treating a seizure disorder, comprising administering to a subject a therapeutically or prophylactically effective amount of the compound of claim 1.

15. The method according to claim 14, wherein the seizure disorder is epilepsy.

16. The method according to claim 14, wherein the seizure disorder is status epilepticus.

17. The method according to claim 14, wherein the seizure disorder comprises partial-onset seizures or primary generalized tonic-clonic seizures, or any combination thereof.

18. The method according to claim 14, wherein the seizure disorder results from a heritable genetic seizure disorder.

19. The method according to claim 14, wherein the seizure disorder results from a brain tumor, a concussive brain injury, or a penetrating brain injury.

20. A method of treating pain, comprising administering to a subject a therapeutically or prophylactically effective amount of the compound of claim 1.

* * * * *

UNITED STATES PATENT AND TRADEMARK OFFICE
CERTIFICATE OF CORRECTION

PATENT NO. : 11,685,726 B2
APPLICATION NO. : 18/147856
DATED : June 27, 2023
INVENTOR(S) : Pearson et al.

Page 1 of 1

It is certified that error appears in the above-identified patent and that said Letters Patent is hereby corrected as shown below:

In the Specification

Column 58, Line 42: Delete "10 PM," and insert -- 10 µM --

Column 59, Line 30: Delete

"
| Compound No. | Electrophysiological assays for antagonist activity. % inhibition +/- SEM of s-AMPA or NMDA induced currents in neurons (whole cell patch-clamp recordings in rat brain cortex slices) | | |
|---|---|---|---|
| | s-AMPA (Tested at 1 pM) | s-AMPA (Tested at 10 pM) | NMDA (Tested at 30 pM) |
| 1 | 55.6 ± 5.8 (n = 3) | >90 (n = 1) | 61.0 ± 6.3 (n = 3) |
| 2 | 21.4 ± 2.1 (n = 3) | NT | NT |

NT = not tested. SEM = Standard Error of the mean. n = number of experiments" and insert

| Compound No. | Electrophysiological assays for antagonist activity. % inhibition +/- SEM of s-AMPA or NMDA induced currents in neurons (whole cell patch-clamp recordings in rat brain cortex slices) | | |
|---|---|---|---|
| | s-AMPA (Tested at 1 µM) | s-AMPA (Tested at 10 µM) | NMDA (Tested at 30 µM) |
| 1 | 55.6 ± 5.8 (n = 3) | >90 (n = 1) | 61.0 ± 6.3 (n = 3) |
| 2 | 21.4 ± 2.1 (n = 3) | NT | NT |

NT = not tested. SEM = Standard Error of the mean. n = number of experiments --

Signed and Sealed this
Fifth Day of September, 2023

Katherine Kelly Vidal
*Director of the United States Patent and Trademark Office*